US009480729B2

(12) United States Patent
Brumm

(10) Patent No.: US 9,480,729 B2
(45) Date of Patent: Nov. 1, 2016

(54) ENZYMES FOR INHIBITING GROWTH OF BIOFILMS AND DEGRADING SAME

(71) Applicant: C5-6 Technologies, Inc., Middleton, WI (US)

(72) Inventor: Phillip J. Brumm, Fitchburg, WI (US)

(73) Assignee: C5-6 Technologies, Inc., Middleton, WI (US)

( * ) Notice: Subject to any disclaimer, the term of this patent is extended or adjusted under 35 U.S.C. 154(b) by 2 days.

(21) Appl. No.: 14/076,701

(22) Filed: Nov. 11, 2013

(65) Prior Publication Data

US 2014/0134149 A1    May 15, 2014

Related U.S. Application Data

(60) Provisional application No. 61/725,257, filed on Nov. 12, 2012.

(51) Int. Cl.
*A61K 38/47* (2006.01)
*A01N 43/40* (2006.01)
*A61K 31/7036* (2006.01)
*A61K 9/00* (2006.01)

(52) U.S. Cl.
CPC ............... *A61K 38/47* (2013.01); *A01N 43/40* (2013.01); *A61K 31/7036* (2013.01); *C12Y 302/01001* (2013.01); *C12Y 302/01004* (2013.01); *C12Y 302/01025* (2013.01); *C12Y 302/01051* (2013.01); *C12Y 302/01091* (2013.01); *A61K 9/0075* (2013.01)

(58) Field of Classification Search
None
See application file for complete search history.

(56) References Cited

U.S. PATENT DOCUMENTS

| 6,830,745 B1 | 12/2004 | Budny et al. |
| 2002/0022005 A1 | 2/2002 | Budny et al. |
| 2002/0037260 A1 | 3/2002 | Budny et al. |

FOREIGN PATENT DOCUMENTS

| EP | 2018857 A1 | 1/2009 |
| WO | WO 00/17331 | 3/2000 |
| WO | WO 01/93875 A1 | 12/2001 |
| WO | WO 2010/115021 A2 | 10/2010 |
| WO | WO 2010/141135 A2 | 12/2010 |

OTHER PUBLICATIONS

Toku-E, Inc (2010) Tobramycin—Product Data Sheet.*
USPTO in house annotation of Fig. 8 herein Sep. 10, 2015.*
Supreme Court Decision No. 12-398 Association for *Molecular Pathology et al v. Myriad Genetics, Inc., et al* (2013).*

Lamed et al, Major characteristics of the cellulolytic system of Clostridium thermocellum coincide with those of the purified cellulosome. Enzyme and microbial technology, vol. 7, Issue 1, Jan. 1985, pp. 37-41.*
Hon-nami et al, Separation and characterization of the complexes constituting the cellulolytic enzyme system of Clostridium thermocellum. Arch Microbiol (1986) 145:13-19.*
Izano et al, Poly-N-acetylglucosamine mediates biofilm formation and antibiotic resistance in Actinobacillus pleuropneumoniae. Microbial Pathogenesis 43 (2007) 1-9.*
Mecikoglu et al, The Effect of Proteolytic Enzyme Serratiopeptidase in the Treatment of Experimental Implant-Related Infection. J. Bone Joint Surg. Am. 88:1208-1214, 2006.*
Anderson GG et al. (2008) In vitro analysis of tobramycin-treated *Pseudomonas aeruginosa* biofilms on cystic fibrosis-derived airway epithelial cells. *Infection and Immunity* 76:1423-1433.
Auler ME et al., (2010) Biofilm formation on intrauterine devices in patients with recurrent vulvovaginal candidiasis. Med Mycol. 48(1):211-6.
Bjarnsholt T et al., (2009) *Pseudomonas aeruginosa* biofilms in the respiratory tract of cystic fibrosis patients. *Pediatric Pulmonology* 44:547-558.
Colvin KM, et al., (Aug. 2012) The Pel and Psl polysaccharides provide *Pseudomonas aeruginosa* structural redundancy within the biofilm matrix. *Environ Microbiol* 14(8):1913-28.
Davis Sc et al., (2008) Microscopic and physiologic evidence for biofilm-associated wound colonization in vivo. Wound Repair Regen. 16(1):23-9.
Digiandomenico A et. al., (Jul. 2012) Identification of broadly protective human antibodies to *Pseudomonas aeruginosa* exopolysaccharide Psl by phenotypic screening. *J Exp Med* 209(7):1273-1287.
Donlan RM et al., (2002) Biofilms: survival mechanisms of clinically relevant microorganisms. Clin Microbiol Rev.15(2):167-93.
Elder, Mark et al., (1995) Biofilm-Related Infection in Ophthalmology. Eye 9, 102-109.
Fanning et al., (2012) Fungal Biofilms. *PLoS Pathogens* vol. 8, Issue 4.
Hall-Stoodley L et al., (2004) P. Bacterial biofilms: from thenatural environment to infectious diseases. *Nat Rev Microbiol.* 2(2):95-108.
Imamura Y et al., (2008) Fusarium and Candida albicans biofilms on soft contact lenses: model development, influence of lens type, and susceptibility to lens care solutions. *Antimicrob Agents Chemother.* 52(1):171-82.
Johansen C et al., (1997) Enzymatic removal and disinfection of bacterial biofilms. Appl Environ Microbiol. 63(9):3724-8.

(Continued)

*Primary Examiner* — Sheridan Swope
(74) *Attorney, Agent, or Firm* — Daniel A. Blasiole; Joseph T. Leone

(57) ABSTRACT

Enzymes for inhibiting growth of biofilms and degrading biofilms. The enzymes comprise glycosyl hydrolases capable of degrading biofilms. The enzymes are formulated in compositions with and without antimicrobial agents. The enzymes with and without the antimicrobial agents are delivered to biofilms to degrade the biofilms and treat infections of microorganisms associated with the biofilms, delivered to surfaces to inhibit growth of biofilms thereon, and administered to animals to inhibit growth of biofilms therein.

4 Claims, 9 Drawing Sheets

(56) References Cited

OTHER PUBLICATIONS

Kaplan Jb., (2009) Therapeutic potential of biofilm-dispersing enzymes. *Int J Artif Organs*. 32(9):545-54.
Klaire Labs, InterFase: Specialized Enzymes Disrupt Biofilm Matrix that Embeds Potential Gastrointestinal Pathogens.
Lear, G et al.; (2012). *Microbial Biofilms: Current Research and Applications*. Caister Academic Press.
Lewis K (2001). Riddle of biofilm resistance. *Antimicrob Agents Chemother*. 45(4):999-1007.
Moreau-Marquis S et al., (2008) The DeltaF508-CFTR mutation results in increased biofilm formation by *Pseudomonas aeruginosa* by increasing iron availability. *Am J Physiol Lung Cell Mol Physiol* 295(1):L25-37.
Moreau-Marquis S et al., (2008) *Pseudomonas aeruginosa* biofilm formation in the cystic fibrosis airway. *Pulm Pharmacol Ther* 21(4):595-9.
Nelson N (1944) A Photometric Adaptation of the Somogyi Method for the Determination of Glucose. *J Biol Chem* 153:375-380.
Parsek MR et al., (2003) Bacterial biofilms: an emerging link to disease pathogenesis. *Annu Rev Microbiol*. 57:677-701.
Research on microbial biofilms (PA-03-047). NIH, National Heart, Lung, and Blood Institute. Dec. 20, 2002.
Rogers. 2008 *Molecular Oral Microbiology*. Caister Academic Press. pp. 65-108.

\* cited by examiner

SEQUENCE LISTING

```
<160> NUMBER OF SEQ ID NOS: 24

<210> SEQ ID NO 1
<211> LENGTH: 1773
<212> TYPE: DNA
<213> ORGANISM: Clostridium thermocellum

<400> SEQUENCE: 1
atggggaaaa tttttggcag gacactgagt ctgctggtaa catttgcaat ggtgtttcc        60 gttcttttag tcatgcccgt ttcaacttat gctgcatatt cccttcctgt ggacgttgaa       120
gcagaagatt gcactcttgg caacggtgcc gttgttacca ccaatgtata cggaactcaa       180
tatcccggat attccggcga cggattcgta tgggtggcca actcgggaac gataacattg       240
gaagtcacca ttcctgaaaa cggtatgtat gagctttcca caagatgctg gatgtatctt       300
ggcaaagaag atgagaccag aatgcaggtt ataagcatca acggaaaatc acacagcaac       360
tattttattc caaacaaagg ccaatggatt gattacagtt tcggattctt ctatcttgag       420
gccggtaaag caactattga gataggttcc tccggaagct ggggctttat actgtacgac       480
aaaatatact ttgaccatgc tgacatgccc gatcatataa ttgacccgac tccgtgtgat       540
ccaaatgcaa ctcctgaaac aagagctctt atgaaatacc ttaccagcgt gtacggaaaa       600
tatgttattt ccggccagca ggagatttac ggaaacggaa acgacggcaa ttatgaactt       660
gaattcgatt atatttatga gaagacaggc aaatatcctg caatcagagg ctttgatttc       720
atgaactaca atcctctgta cggatgggaa gacggtacaa cggcacgtat aatcgactgg       780
gtaaaaaatc gcggcggtat tgcaacagca tgctggcata taaatattcc cagggatttt       840
```

```
gcaagttata aactcggtga gccggtggat tggacaaact gtacatacaa accgacaagc    900
agctttaata ccgcaaactg ccttgatgaa acaacaaaag aacatgctta cctgatgatg    960
gcaattgaag accttgcaga gcagctttta attcttcagg agcaaaacat tcctatactt   1020
ttccgtccgt tccatgaagc tgaaggctac aacaacaccg acggctccgg cgcatggttc   1080
tggtggggtt ctgcaggtgc tgaagtttac aaggaactct ggaaacttct ttataaaact   1140
cttaccgaaa atacggcat tcataatttg atatgggaag taaaccttta tacatatgcc   1200
aattcttatg aatggtatcc cggcgatgag tatgtggaca ttatcggata cgacaaatat   1260
gaaggttcac ccaatacctg ggcacaagc gccgcatcat cattattcct tacacttgta   1320
aattacacaa acgacacaaa gatggttgca ttgactgaaa atgacgttat tcccgatatt   1380
caaaatatag ttaatgagga agcctggtgg ctgtatttct gcccatggta cggtgatttc   1440
cttatgagtc ccagatacaa cgaccccgta cttttgaaca ctatctacaa cagtgaatat   1500
gtaatcacct tggatgaact tccggaaaac ctttatgaat atgatggtga ataccggat   1560
atcaactacg gcgatttgaa caatgacgga aatataaact caaccgatta tatgatactg   1620
aagaaatata ttttaaaagt tcttgaaaga atgaatgtcc ctgaaaaagc agcagattta   1680
aacggtgacg gttcaatcaa ttcaaccgat ttgacaatat taaaaagatt tataatgaaa   1740
gcaattacaa aatttcccgt tacacaaaag taa                                1773
```

<210> SEQ ID NO 2
<211> LENGTH: 590
<212> TYPE: PRT
<213> ORGANISM: Clostridium thermocellum

<400> SEQUENCE: 2

```
Met Gly Lys Ile Phe Gly Arg Thr Leu Ser Leu Leu Val Thr Phe Ala
1               5                   10                  15

Met Val Phe Ser Val Leu Leu Val Met Pro Val Ser Thr Tyr Ala Ala
                20                  25                  30

Tyr Ser Leu Pro Val Asp Val Glu Ala Glu Asp Cys Thr Leu Gly Asn
            35                  40                  45

Gly Ala Val Val Thr Thr Asn Val Tyr Gly Thr Gln Tyr Pro Gly Tyr
        50                  55                  60

Ser Gly Asp Gly Phe Val Trp Val Ala Asn Ser Gly Thr Ile Thr Leu
65                  70                  75                  80

Glu Val Thr Ile Pro Glu Asn Gly Met Tyr Glu Leu Ser Thr Arg Cys
                85                  90                  95

Trp Met Tyr Leu Gly Lys Glu Asp Glu Thr Arg Met Gln Val Ile Ser
                100                 105                 110

Ile Asn Gly Lys Ser His Ser Asn Tyr Phe Ile Pro Asn Lys Gly Gln
            115                 120                 125

Trp Ile Asp Tyr Ser Phe Gly Phe Phe Tyr Leu Glu Ala Gly Lys Ala
        130                 135                 140

Thr Ile Glu Ile Gly Ser Ser Gly Ser Trp Gly Phe Ile Leu Tyr Asp
145                 150                 155                 160

Lys Ile Tyr Phe Asp His Ala Asp Met Pro Asp His Ile Ile Asp Pro
                165                 170                 175

Thr Pro Cys Asp Pro Asn Ala Thr Pro Glu Thr Arg Ala Leu Met Lys
            180                 185                 190

Tyr Leu Thr Ser Val Tyr Gly Lys Tyr Val Ile Ser Gly Gln Gln Glu
        195                 200                 205
```

```
Ile Tyr Gly Asn Gly Asn Asp Gly Asn Tyr Glu Leu Glu Phe Asp Tyr
        210                 215                 220

Ile Tyr Glu Lys Thr Gly Lys Tyr Pro Ala Ile Arg Gly Phe Asp Phe
225                 230                 235                 240

Met Asn Tyr Asn Pro Leu Tyr Gly Trp Glu Asp Gly Thr Thr Ala Arg
                245                 250                 255

Ile Ile Asp Trp Val Lys Asn Arg Gly Gly Ile Ala Thr Ala Cys Trp
                260                 265                 270

His Ile Asn Ile Pro Arg Asp Phe Ala Ser Tyr Lys Leu Gly Glu Pro
                275                 280                 285

Val Asp Trp Thr Asn Cys Thr Tyr Lys Pro Thr Ser Ser Phe Asn Thr
290                 295                 300

Ala Asn Cys Leu Asp Glu Thr Thr Lys Glu His Ala Tyr Leu Met Met
305                 310                 315                 320

Ala Ile Glu Asp Leu Ala Glu Gln Leu Leu Ile Leu Gln Glu Gln Asn
                325                 330                 335

Ile Pro Ile Leu Phe Arg Pro Phe His Glu Ala Glu Gly Tyr Asn Asn
                340                 345                 350

Thr Asp Gly Ser Gly Ala Trp Phe Trp Trp Gly Ser Ala Gly Ala Glu
                355                 360                 365

Val Tyr Lys Glu Leu Trp Lys Leu Leu Tyr Lys Thr Leu Thr Glu Lys
370                 375                 380

Tyr Gly Ile His Asn Leu Ile Trp Glu Val Asn Leu Tyr Thr Tyr Ala
385                 390                 395                 400

Asn Ser Tyr Glu Trp Tyr Pro Gly Asp Glu Tyr Val Asp Ile Ile Gly
                405                 410                 415

Tyr Asp Lys Tyr Glu Gly Ser Pro Asn Thr Trp Gly Thr Ser Ala Ala
                420                 425                 430

Ser Ser Leu Phe Leu Thr Leu Val Asn Tyr Thr Asn Asp Thr Lys Met
                435                 440                 445

Val Ala Leu Thr Glu Asn Asp Val Ile Pro Asp Ile Gln Asn Ile Val
        450                 455                 460

Asn Glu Glu Ala Trp Trp Leu Tyr Phe Cys Pro Trp Tyr Gly Asp Phe
465                 470                 475                 480

Leu Met Ser Pro Arg Tyr Asn Asp Pro Val Leu Leu Asn Thr Ile Tyr
                485                 490                 495

Asn Ser Glu Tyr Val Ile Thr Leu Asp Glu Leu Pro Glu Asn Leu Tyr
                500                 505                 510

Glu Tyr Asp Gly Glu Ile Pro Asp Ile Asn Tyr Gly Asp Leu Asn Asn
        515                 520                 525

Asp Gly Asn Ile Asn Ser Thr Asp Tyr Met Ile Leu Lys Lys Tyr Ile
        530                 535                 540

Leu Lys Val Leu Glu Arg Met Asn Val Pro Glu Lys Ala Ala Asp Leu
545                 550                 555                 560

Asn Gly Asp Gly Ser Ile Asn Ser Thr Asp Leu Thr Ile Leu Lys Arg
                565                 570                 575

Phe Ile Met Lys Ala Ile Thr Lys Phe Pro Val Thr Gln Lys
                580                 585                 590

<210> SEQ ID NO 3
<211> LENGTH: 559
<212> TYPE: PRT
<213> ORGANISM: Clostridium thermocellum

<400> SEQUENCE: 3
```

-continued

```
Ala Tyr Ser Leu Pro Val Asp Val Glu Ala Glu Asp Cys Thr Leu Gly
1               5                   10                  15

Asn Gly Ala Val Val Thr Thr Asn Val Tyr Gly Thr Gln Tyr Pro Gly
            20                  25                  30

Tyr Ser Gly Asp Gly Phe Val Trp Val Ala Asn Ser Gly Thr Ile Thr
        35                  40                  45

Leu Glu Val Thr Ile Pro Glu Asn Gly Met Tyr Glu Leu Ser Thr Arg
50                  55                  60

Cys Trp Met Tyr Leu Gly Lys Glu Asp Glu Thr Arg Met Gln Val Ile
65              70                  75                  80

Ser Ile Asn Gly Lys Ser His Ser Asn Tyr Phe Ile Pro Asn Lys Gly
                85                  90                  95

Gln Trp Ile Asp Tyr Ser Phe Gly Phe Phe Tyr Leu Glu Ala Gly Lys
            100                 105                 110

Ala Thr Ile Glu Ile Gly Ser Ser Gly Ser Trp Gly Phe Ile Leu Tyr
        115                 120                 125

Asp Lys Ile Tyr Phe Asp His Ala Asp Met Pro Asp His Ile Ile Asp
    130                 135                 140

Pro Thr Pro Cys Asp Pro Asn Ala Thr Pro Glu Thr Arg Ala Leu Met
145                 150                 155                 160

Lys Tyr Leu Thr Ser Val Tyr Gly Lys Tyr Val Ile Ser Gly Gln Gln
                165                 170                 175

Glu Ile Tyr Gly Asn Gly Asn Asp Gly Asn Tyr Glu Leu Glu Phe Asp
            180                 185                 190

Tyr Ile Tyr Glu Lys Thr Gly Lys Tyr Pro Ala Ile Arg Gly Phe Asp
        195                 200                 205

Phe Met Asn Tyr Asn Pro Leu Tyr Gly Trp Glu Asp Gly Thr Thr Ala
    210                 215                 220

Arg Ile Ile Asp Trp Val Lys Asn Arg Gly Gly Ile Ala Thr Ala Cys
225                 230                 235                 240

Trp His Ile Asn Ile Pro Arg Asp Phe Ala Ser Tyr Lys Leu Gly Glu
                245                 250                 255

Pro Val Asp Trp Thr Asn Cys Thr Tyr Lys Pro Thr Ser Ser Phe Asn
            260                 265                 270

Thr Ala Asn Cys Leu Asp Glu Thr Thr Lys Glu His Ala Tyr Leu Met
        275                 280                 285

Met Ala Ile Glu Asp Leu Ala Glu Gln Leu Leu Ile Leu Gln Glu Gln
    290                 295                 300

Asn Ile Pro Ile Leu Phe Arg Pro Phe His Glu Ala Glu Gly Tyr Asn
305                 310                 315                 320

Asn Thr Asp Gly Ser Gly Ala Trp Phe Trp Trp Gly Ser Ala Gly Ala
                325                 330                 335

Glu Val Tyr Lys Glu Leu Trp Lys Leu Leu Tyr Lys Thr Leu Thr Glu
            340                 345                 350

Lys Tyr Gly Ile His Asn Leu Ile Trp Glu Val Asn Leu Tyr Thr Tyr
        355                 360                 365

Ala Asn Ser Tyr Glu Trp Tyr Pro Gly Asp Glu Tyr Val Asp Ile Ile
    370                 375                 380

Gly Tyr Asp Lys Tyr Glu Gly Ser Pro Asn Thr Trp Gly Thr Ser Ala
385                 390                 395                 400

Ala Ser Ser Leu Phe Leu Thr Leu Val Asn Tyr Thr Asn Asp Thr Lys
                405                 410                 415
```

```
Met Val Ala Leu Thr Glu Asn Asp Val Ile Pro Asp Ile Gln Asn Ile
            420                 425                 430

Val Asn Glu Glu Ala Trp Trp Leu Tyr Phe Cys Pro Trp Tyr Gly Asp
                435                 440                 445

Phe Leu Met Ser Pro Arg Tyr Asn Asp Pro Val Leu Leu Asn Thr Ile
        450                 455                 460

Tyr Asn Ser Glu Tyr Val Ile Thr Leu Asp Glu Leu Pro Glu Asn Leu
465                 470                 475                 480

Tyr Glu Tyr Asp Gly Glu Ile Pro Asp Ile Asn Tyr Gly Asp Leu Asn
                485                 490                 495

Asn Asp Gly Asn Ile Asn Ser Thr Asp Tyr Met Ile Leu Lys Lys Tyr
            500                 505                 510

Ile Leu Lys Val Leu Glu Arg Met Asn Val Pro Glu Lys Ala Ala Asp
        515                 520                 525

Leu Asn Gly Asp Gly Ser Ile Asn Ser Thr Asp Leu Thr Ile Leu Lys
        530                 535                 540

Arg Phe Ile Met Lys Ala Ile Thr Lys Phe Pro Val Thr Gln Lys
545                 550                 555

<210> SEQ ID NO 4
<211> LENGTH: 1983
<212> TYPE: DNA
<213> ORGANISM: Clostridium thermocellum

<400> SEQUENCE: 4
atgggtcaaa aacattttaa aagaagtctg ttgtctgtat taacaatttc agccctgatt    60
atctcctgcc ttttcagttt tattttcgtt aacgcagatg acacttctga agaacccgct   120
ttggaaggcc tgtctataca ctatatggac ggcacactgg acgtaaaata tcagagcatg   180
cgtccttaca taattattca taacaacagc ggcatggatg tggacatggc cgaccttagg   240
gtaaggtatt actacgaaaa agagggtgtt accgaagaag tccttacatg cttttataca   300
gcaataggtg cggacaaaat atttgccgaa tttcatcccg agctgggata cgctgaaatc   360
ggctttacca gtgatgccgg aattataaaa agcggtggca acagcgggca gctgcagctg   420
gtactgaaaa aaatatcgaa cggttactac gaccaaagca atgattattc ttatgaccca   480
agttacactg attatgcaga atatgataaa ataacactct attacaaagg taaactggta   540
tggggaaaag aaggacctcc tccgccaccg gaaccgacac ctccgccaaa caacgacgac   600
tggcttcatg tggagggaaa tctaatcaag gatgcccagg gaaataccgt ttatcttaca   660
ggaatcaact ggtttggatt tgaaactgac ggagcaaacg ttttttacgg ccttaacaaa   720
tgcaaccttg aggattctct tgatttaatg gcaaaattag ttttaatat tctcagaatc   780 cccatcagtc tgaaattat tctgcaatgg aaaaacggcg aacgtgtaga aacttccttt   840
gtaaacacct atgaaaaccc gcgtcttgac ggcctcagca gtcttgaaat actggactat   900
acaataaatc acatgaagaa aaacggtatg aagccatgc ttgacatgca cagttcaacc   960
aaggactcat accaggaaaa cctctggtat aacaaggata taaccatgga agaatttatc  1020
gaagcctgga atggattgt cgaaagatac aaagacgatg atacggtcat tgcagtggat  1080
ctcaaaaatg aacctcatgg aaagtactcc ggtccgaata tcgccaaatg ggatgattcg  1140
gatgatccaa caactggaa aagggcggcg gaaatcattg ccgaagaaat tcttgcaatc  1200
aatccaaatc ttttaatcgt cgtagagggt gttgaggcat acccgatgga agggtatgat  1260
tacaccaact gcggtgagtt taccacatac tgtaactggt ggggcggaaa tttaagagga  1320
```

-continued

```
gttgccgacc atcctgttgt catatccgct ccggacaagc tcgtatattc cgtacatgat   1380
tacggaccgg acatctatat gcagccgtgg tttaaaaaag atttcgacat taacacccctt  1440 tatgaggaat gctggtaccc aaactggtac tacattgtcg agcaaaatat tgcgcctatg   1500
ttaatcggcg aatggggagg caagcttatc aatgaaaaca accggaagtg gcttgaatgt   1560
ttggctacct ttatttcaga aaagaaactg catcatacct tctgggcttt taatcccaac   1620
tcagccgaca ccggcggtct aatgcttgag gattggaaaa ccgttgatga ggaaaaatat   1680
gcaataattg agcccacatt gtggaagaaa ggtctggatc atgtaatacc gctgggagga   1740
attacggagg atacctttaa atatggtgac gttaacggtg attttgccgt aaactccaac   1800
gaccttacat tgataaaacg ctacgtcctt aaaaatattg acgaattccc ctcttctcat   1860
ggattgaaag ctgccgacgt ggacggagat gaaaaaataa cctccagtga tgctgctctt   1920
gtaaaaaggt acgttctaag agccataaca tcattcccgg tggaagaaaa ccaaaatgaa   1980
taa                                                                 1983
```

<210> SEQ ID NO 5
<211> LENGTH: 660
<212> TYPE: PRT
<213> ORGANISM: Clostridium thermocellum

<400> SEQUENCE: 5

```
Met Gly Gln Lys His Phe Lys Arg Ser Leu Leu Ser Val Leu Thr Ile
1               5                   10                  15

Ser Ala Leu Ile Ile Ser Cys Leu Phe Ser Phe Ile Phe Val Asn Ala
            20                  25                  30

Asp Asp Thr Ser Glu Glu Pro Ala Leu Glu Gly Leu Ser Ile His Tyr
        35                  40                  45

Met Asp Gly Thr Leu Asp Val Lys Tyr Gln Ser Met Arg Pro Tyr Ile
    50                  55                  60

Ile Ile His Asn Asn Ser Gly Met Asp Val Asp Met Ala Asp Leu Arg
65                  70                  75                  80

Val Arg Tyr Tyr Glu Lys Glu Gly Val Thr Glu Glu Val Leu Thr
                85                  90                  95

Cys Phe Tyr Thr Ala Ile Gly Ala Asp Lys Ile Phe Ala Glu Phe His
                100                 105                 110

Pro Glu Leu Gly Tyr Ala Glu Ile Gly Phe Thr Ser Asp Ala Gly Ile
            115                 120                 125

Ile Lys Ser Gly Gly Asn Ser Gly Gln Leu Gln Leu Val Leu Lys Lys
        130                 135                 140

Ile Ser Asn Gly Tyr Tyr Asp Gln Ser Asn Asp Tyr Ser Tyr Asp Pro
145                 150                 155                 160

Ser Tyr Thr Asp Tyr Ala Glu Tyr Asp Lys Ile Thr Leu Tyr Tyr Lys
                165                 170                 175

Gly Lys Leu Val Trp Gly Lys Glu Gly Pro Pro Pro Glu Pro
                180                 185                 190

Thr Pro Pro Pro Asn Asn Asp Asp Trp Leu His Val Glu Gly Asn Leu
            195                 200                 205

Ile Lys Asp Ala Gln Gly Asn Thr Val Tyr Leu Thr Gly Ile Asn Trp
        210                 215                 220

Phe Gly Phe Glu Thr Asp Gly Ala Asn Gly Phe Tyr Gly Leu Asn Lys
225                 230                 235                 240

Cys Asn Leu Glu Asp Ser Leu Asp Leu Met Ala Lys Leu Gly Phe Asn
                245                 250                 255
```

```
Ile Leu Arg Ile Pro Ile Ser Ala Glu Ile Leu Gln Trp Lys Asn
            260                 265                 270

Gly Glu Arg Val Glu Thr Ser Phe Val Asn Thr Tyr Glu Asn Pro Arg
        275                 280                 285

Leu Asp Gly Leu Ser Ser Leu Glu Ile Leu Asp Tyr Thr Ile Asn His
    290                 295                 300

Met Lys Lys Asn Gly Met Lys Ala Met Leu Asp Met His Ser Ser Thr
305                 310                 315                 320

Lys Asp Ser Tyr Gln Glu Asn Leu Trp Tyr Asn Lys Asp Ile Thr Met
            325                 330                 335

Glu Glu Phe Ile Glu Ala Trp Lys Trp Ile Val Glu Arg Tyr Lys Asp
            340                 345                 350

Asp Asp Thr Val Ile Ala Val Asp Leu Lys Asn Glu Pro His Gly Lys
            355                 360                 365

Tyr Ser Gly Pro Asn Ile Ala Lys Trp Asp Asp Ser Asp Pro Asn
370                 375                 380

Asn Trp Lys Arg Ala Ala Glu Ile Ile Ala Glu Ile Leu Ala Ile
385                 390                 395                 400

Asn Pro Asn Leu Leu Ile Val Val Glu Gly Val Glu Ala Tyr Pro Met
                405                 410                 415

Glu Gly Tyr Asp Tyr Thr Asn Cys Gly Glu Phe Thr Thr Tyr Cys Asn
            420                 425                 430

Trp Trp Gly Gly Asn Leu Arg Gly Val Ala Asp His Pro Val Val Ile
            435                 440                 445

Ser Ala Pro Asp Lys Leu Val Tyr Ser Val His Asp Tyr Gly Pro Asp
    450                 455                 460

Ile Tyr Met Gln Pro Trp Phe Lys Lys Asp Phe Asp Ile Asn Thr Leu
465                 470                 475                 480

Tyr Glu Glu Cys Trp Tyr Pro Asn Trp Tyr Tyr Ile Val Gln Asn
            485                 490                 495

Ile Ala Pro Met Leu Ile Gly Glu Trp Gly Gly Lys Leu Ile Asn Glu
            500                 505                 510

Asn Asn Arg Lys Trp Leu Glu Cys Leu Ala Thr Phe Ile Ser Glu Lys
            515                 520                 525

Lys Leu His His Thr Phe Trp Ala Phe Asn Pro Asn Ser Ala Asp Thr
    530                 535                 540

Gly Gly Leu Met Leu Glu Asp Trp Lys Thr Val Asp Glu Glu Lys Tyr
545                 550                 555                 560

Ala Ile Ile Glu Pro Thr Leu Trp Lys Lys Gly Leu Asp His Val Ile
                565                 570                 575

Pro Leu Gly Gly Ile Thr Glu Asp Thr Phe Lys Tyr Gly Asp Val Asn
            580                 585                 590

Gly Asp Phe Ala Val Asn Ser Asn Asp Leu Thr Leu Ile Lys Arg Tyr
            595                 600                 605

Val Leu Lys Asn Ile Asp Glu Phe Pro Ser Ser His Gly Leu Lys Ala
    610                 615                 620

Ala Asp Val Asp Gly Asp Glu Lys Ile Thr Ser Ser Asp Ala Ala Leu
625                 630                 635                 640

Val Lys Arg Tyr Val Leu Arg Ala Ile Thr Ser Phe Pro Val Glu Glu
            645                 650                 655

Asn Gln Asn Glu
            660
```

<210> SEQ ID NO 6
<211> LENGTH: 628
<212> TYPE: PRT
<213> ORGANISM: Clostridium thermocellum

<400> SEQUENCE: 6

```
Asp Asp Thr Ser Glu Pro Ala Leu Glu Gly Leu Ser Ile His Tyr
1               5                  10                  15

Met Asp Gly Thr Leu Asp Val Lys Tyr Gln Ser Met Arg Pro Tyr Ile
                20                  25                  30

Ile Ile His Asn Asn Ser Gly Met Asp Val Asp Met Ala Asp Leu Arg
            35                  40                  45

Val Arg Tyr Tyr Tyr Glu Lys Glu Gly Val Thr Glu Glu Val Leu Thr
        50                  55                  60

Cys Phe Tyr Thr Ala Ile Gly Ala Asp Lys Ile Phe Ala Glu Phe His
65                  70                  75                  80

Pro Glu Leu Gly Tyr Ala Glu Ile Gly Phe Thr Ser Asp Ala Gly Ile
                85                  90                  95

Ile Lys Ser Gly Gly Asn Ser Gly Gln Leu Gln Leu Val Leu Lys Lys
            100                 105                 110

Ile Ser Asn Gly Tyr Tyr Asp Gln Ser Asn Asp Tyr Ser Tyr Asp Pro
        115                 120                 125

Ser Tyr Thr Asp Tyr Ala Glu Tyr Asp Lys Ile Thr Leu Tyr Tyr Lys
    130                 135                 140

Gly Lys Leu Val Trp Gly Lys Glu Gly Pro Pro Pro Pro Glu Pro
145                 150                 155                 160

Thr Pro Pro Pro Asn Asn Asp Asp Trp Leu His Val Glu Gly Asn Leu
                165                 170                 175

Ile Lys Asp Ala Gln Gly Asn Thr Val Tyr Leu Thr Gly Ile Asn Trp
            180                 185                 190

Phe Gly Phe Glu Thr Asp Gly Ala Asn Gly Phe Tyr Gly Leu Asn Lys
        195                 200                 205

Cys Asn Leu Glu Asp Ser Leu Asp Leu Met Ala Lys Leu Gly Phe Asn
    210                 215                 220

Ile Leu Arg Ile Pro Ile Ser Ala Glu Ile Ile Leu Gln Trp Lys Asn
225                 230                 235                 240

Gly Glu Arg Val Glu Thr Ser Phe Val Asn Thr Tyr Glu Asn Pro Arg
                245                 250                 255

Leu Asp Gly Leu Ser Ser Leu Glu Ile Leu Asp Tyr Thr Ile Asn His
            260                 265                 270

Met Lys Lys Asn Gly Met Lys Ala Met Leu Asp Met His Ser Ser Thr
        275                 280                 285

Lys Asp Ser Tyr Gln Glu Asn Leu Trp Tyr Asn Lys Asp Ile Thr Met
    290                 295                 300

Glu Glu Phe Ile Glu Ala Trp Lys Trp Ile Val Glu Arg Tyr Lys Asp
305                 310                 315                 320

Asp Asp Thr Val Ile Ala Val Asp Leu Lys Asn Glu Pro His Gly Lys
                325                 330                 335

Tyr Ser Gly Pro Asn Ile Ala Lys Trp Asp Asp Ser Asp Pro Asn
            340                 345                 350

Asn Trp Lys Arg Ala Ala Glu Ile Ile Ala Glu Ile Leu Ala Ile
        355                 360                 365

Asn Pro Asn Leu Leu Ile Val Val Glu Gly Val Glu Ala Tyr Pro Met
    370                 375                 380
```

Glu Gly Tyr Asp Tyr Thr Asn Cys Gly Glu Phe Thr Thr Tyr Cys Asn
385                 390                 395                 400

Trp Trp Gly Gly Asn Leu Arg Gly Val Ala Asp His Pro Val Val Ile
            405                 410                 415

Ser Ala Pro Asp Lys Leu Val Tyr Ser Val His Asp Tyr Gly Pro Asp
        420                 425                 430

Ile Tyr Met Gln Pro Trp Phe Lys Lys Asp Phe Asp Ile Asn Thr Leu
    435                 440                 445

Tyr Glu Glu Cys Trp Tyr Pro Asn Trp Tyr Tyr Ile Val Glu Gln Asn
450                 455                 460

Ile Ala Pro Met Leu Ile Gly Glu Trp Gly Gly Lys Leu Ile Asn Glu
465                 470                 475                 480

Asn Asn Arg Lys Trp Leu Glu Cys Leu Ala Thr Phe Ile Ser Glu Lys
            485                 490                 495

Lys Leu His His Thr Phe Trp Ala Phe Asn Pro Asn Ser Ala Asp Thr
        500                 505                 510

Gly Gly Leu Met Leu Glu Asp Trp Lys Thr Val Asp Glu Glu Lys Tyr
    515                 520                 525

Ala Ile Ile Glu Pro Thr Leu Trp Lys Lys Gly Leu Asp His Val Ile
530                 535                 540

Pro Leu Gly Gly Ile Thr Glu Asp Thr Phe Lys Tyr Gly Asp Val Asn
545                 550                 555                 560

Gly Asp Phe Ala Val Asn Ser Asn Asp Leu Thr Leu Ile Lys Arg Tyr
            565                 570                 575

Val Leu Lys Asn Ile Asp Glu Phe Pro Ser Ser His Gly Leu Lys Ala
        580                 585                 590

Ala Asp Val Asp Gly Asp Glu Lys Ile Thr Ser Ser Asp Ala Ala Leu
    595                 600                 605

Val Lys Arg Tyr Val Leu Arg Ala Ile Thr Ser Phe Pro Val Glu Glu
610                 615                 620

Asn Gln Asn Glu
625

<210> SEQ ID NO 7
<211> LENGTH: 2688
<212> TYPE: DNA
<213> ORGANISM: Clostridium thermocellum

<400> SEQUENCE: 7
atgaatttca gaagaatgtt gtgcgcagcc atagtgttga caattgtact gtccattatg      60
ctgccgtcaa ctgttttgc tttggaagac aagtctccaa agttgccgga ttataaaaac      120 gacctttgt atgaaagaac attcgacgaa ggtctttgct ttccgtggca tacttgcgaa      180
gacagtggag gaaatgtga tttcgctgtt gttgatgttc aggagagcc tgggaacaaa      240 gctttccgct tgacagtaat tgacaaagga caaacaagt ggagtgtcca gatgagacac      300
agaggtatta ccctcgagca aggacataca tacacggtaa ggtttacgat tggtctgac      360 aaatcctgta ggttttatgc taaaattggt cagatgggtg aaccctatac tgaatattgg      420
aacaataact ggaatccatt caaccttaca ccaggacaga gcttacagt tgaacagaat      480 tttacaatga actatcctac tgatgacaca tgcgagttca cattccattt gggtggagaa      540
cttgctgcag gtacacctta ctatgtttac cttgatgatg tatctctcta cgatcctagg      600
tttgtaaagc ctgttgaata tgtacttccg cagccggatg tacgtgttaa ccaggtagga      660

```
tacttaccgt tgcaaagaa gtatgctact gttgtatctt cttcaaccag cccgcttaag      720
tggcagcttc tcaattcggc aaatcaggtt gttttggaag gtaatacaat accaaaagga     780
cttgacaaag attcacagga ttatgtacat tggatagatt tctccaactt taagactgaa    840
ggaaaaggtt attacttcaa gcttccgact gtaaacagcg atacaaatta cagccatcct    900
ttcgatatca gtgctgatat ttactccaag atgaaatttg atgcattggc attcttctat    960
cacaagagaa gcggtattcc tattgaaatg ccgtatgcag aggagaaaca gtggaccaga    1020
cctgcaggac atattggtgt tgctccgaac aaaggagaca caaatgttcc tacatggcct    1080
caggatgatg aatatgcagg aagacctcaa aaatattata caaagatgt aaccggtgga    1140 tggtatgatg ccggtgacca cggtaaatat gttgtaaacg gcggtatagc tgtttggaca    1200
ttgatgaaca tgtatgaaag ggcaaaaatc agaggcatag ctaatcaagg tgcttataaa    1260
gacggtggaa tgaacatacc ggagagaaat aacggttatc cggacattct tgatgaagca    1320
agatgggaaa ttgagttctt taagaaaatg caggtaactg aaaaagagga tccttccata    1380
gccggaatgg tacaccacaa aattcacgac ttcagatgga ctgctttggg tatgttgcct    1440
cacgaagatc cccagccacg ttacttaagg ccggtaagta cggctgcgac tttgaacttt    1500
gcggcaactt tggcacaaag tgcacgtctt tggaaagatt atgatccgac ttttgctgct    1560
gactgtttgg aaaaggctga aatagcatgg caggcggcat taaagcatcc tgatatttat    1620
gctgagtata ctcccggtag cggtggtccc ggaggcggac catacaatga cgactatgtc    1680
ggagacgaat tctactgggc agcctgcgaa ctttatgtaa caacaggaaa agacgaatat    1740
aagaattacc tgatgaattc acctcactat cttgaaatgc ctgcaaagat gggtgaaaac    1800
ggtggagcaa acggagaaga caacggattg tggggatgct tcacctgggg aactactcaa    1860
ggattgggaa ctattactct tgcattagtt gaaaacggat tgccgtctgc agacattcaa    1920
aaggcaagaa acaatatagc taaagctgca gacaaatggc ttgagaatat tgaagagcaa    1980
ggttacagac tgccgatcaa acaggcggag gatgagagag gcggttatcc atggggttca    2040
aactccttca ttttgaacca gatgatagtt atgggatacg catatgactt tacaggcaac    2100
agcaagtatc ttgacggaat gcaggatggt atgagctacc tgttgggaag aaacggactg    2160
gatcagtcct atgtaacagg gtatggtgag cgtccacttc agaatcctca tgacagattc    2220
tggacgccac agacaagtaa gaaattccct gctccacctc cgggtataat tgccggtggt    2280
ccgaactccc gtttcgaaga cccgacaata actgcagcag ttaagaagga tacaccgccg    2340
cagaagtgct acattgacca tacagactca tggtcaacca acgagataac tattaactgg    2400
aatgctccgt tgcatgggt tacagcttat ctcgatgaaa ttgacttaat aacaccgcca    2460
ggaggagtag acccagaaga accggaggtt atttatggtg actgcaatgg cgacggaaaa    2520
gttaattcaa ctgacgctgt ggcattgaag agatatatct tgagatcagg tataagcatc    2580
aacactgata tgctgatgt aaatgctgat ggcagagtta actctacaga cttggcaata    2640
ttgaagagat atattcttaa agagatagat gtattgccac ataaataa                 2688
```

<210> SEQ ID NO 8
<211> LENGTH: 895
<212> TYPE: PRT
<213> ORGANISM: Clostridium thermocellum

<400> SEQUENCE: 8

```
Met Asn Phe Arg Arg Met Leu Cys Ala Ala Ile Val Leu Thr Ile Val
1               5                   10                  15
```

-continued

```
Leu Ser Ile Met Leu Pro Ser Thr Val Phe Ala Leu Glu Asp Lys Ser
             20                  25                  30

Pro Lys Leu Pro Asp Tyr Lys Asn Asp Leu Leu Tyr Glu Arg Thr Phe
         35                  40                  45

Asp Glu Gly Leu Cys Phe Pro Trp His Thr Cys Glu Asp Ser Gly Gly
     50                  55                  60

Lys Cys Asp Phe Ala Val Val Asp Val Pro Gly Pro Gly Asn Lys
65                  70                  75                  80

Ala Phe Arg Leu Thr Val Ile Asp Lys Gly Gln Asn Lys Trp Ser Val
                 85                  90                  95

Gln Met Arg His Arg Gly Ile Thr Leu Glu Gln Gly His Thr Tyr Thr
            100                 105                 110

Val Arg Phe Thr Ile Trp Ser Asp Lys Ser Cys Arg Val Tyr Ala Lys
        115                 120                 125

Ile Gly Gln Met Gly Glu Pro Tyr Thr Glu Tyr Trp Asn Asn Asn Trp
    130                 135                 140

Asn Pro Phe Asn Leu Thr Pro Gly Gln Lys Leu Thr Val Glu Gln Asn
145                 150                 155                 160

Phe Thr Met Asn Tyr Pro Thr Asp Asp Thr Cys Glu Phe Thr Phe His
                165                 170                 175

Leu Gly Gly Glu Leu Ala Ala Gly Thr Pro Tyr Tyr Val Tyr Leu Asp
            180                 185                 190

Asp Val Ser Leu Tyr Asp Pro Arg Phe Val Lys Pro Val Glu Tyr Val
        195                 200                 205

Leu Pro Gln Pro Asp Val Arg Val Asn Gln Val Gly Tyr Leu Pro Phe
    210                 215                 220

Ala Lys Lys Tyr Ala Thr Val Val Ser Ser Thr Ser Pro Leu Lys
225                 230                 235                 240

Trp Gln Leu Leu Asn Ser Ala Asn Gln Val Val Leu Glu Gly Asn Thr
                245                 250                 255

Ile Pro Lys Gly Leu Asp Lys Asp Ser Gln Asp Tyr Val His Trp Ile
            260                 265                 270

Asp Phe Ser Asn Phe Lys Thr Glu Gly Lys Gly Tyr Tyr Phe Lys Leu
        275                 280                 285

Pro Thr Val Asn Ser Asp Thr Asn Tyr Ser His Pro Phe Asp Ile Ser
    290                 295                 300

Ala Asp Ile Tyr Ser Lys Met Lys Phe Asp Ala Leu Ala Phe Phe Tyr
305                 310                 315                 320

His Lys Arg Ser Gly Ile Pro Ile Glu Met Pro Tyr Ala Gly Gly Glu
                325                 330                 335

Gln Trp Thr Arg Pro Ala Gly His Ile Gly Val Ala Pro Asn Lys Gly
            340                 345                 350

Asp Thr Asn Val Pro Thr Trp Pro Gln Asp Glu Tyr Ala Gly Arg
        355                 360                 365

Pro Gln Lys Tyr Tyr Thr Lys Asp Val Thr Gly Gly Tyr Asp Ala
    370                 375                 380

Gly Asp His Gly Lys Tyr Val Val Asn Gly Ile Ala Val Trp Thr
385                 390                 395                 400

Leu Met Asn Met Tyr Glu Arg Ala Lys Ile Arg Gly Ile Ala Asn Gln
                405                 410                 415

Gly Ala Tyr Lys Asp Gly Gly Met Asn Ile Pro Glu Arg Asn Asn Gly
            420                 425                 430

Tyr Pro Asp Ile Leu Asp Glu Ala Arg Trp Glu Ile Glu Phe Phe Lys
```

435                 440                 445
Lys Met Gln Val Thr Glu Lys Glu Asp Pro Ser Ile Ala Gly Met Val
                450                 455                 460

His His Lys Ile His Asp Phe Arg Trp Thr Ala Leu Gly Met Leu Pro
465                 470                 475                 480

His Glu Asp Pro Gln Pro Arg Tyr Leu Arg Pro Val Ser Thr Ala Ala
                    485                 490                 495

Thr Leu Asn Phe Ala Ala Thr Leu Ala Gln Ser Ala Arg Leu Trp Lys
                500                 505                 510

Asp Tyr Asp Pro Thr Phe Ala Ala Asp Cys Leu Glu Lys Ala Glu Ile
                515                 520                 525

Ala Trp Gln Ala Ala Leu Lys His Pro Asp Ile Tyr Ala Glu Tyr Thr
            530                 535                 540

Pro Gly Ser Gly Gly Pro Gly Gly Pro Tyr Asn Asp Asp Tyr Val
545                 550                 555                 560

Gly Asp Glu Phe Tyr Trp Ala Ala Cys Glu Leu Tyr Val Thr Thr Gly
                565                 570                 575

Lys Asp Glu Tyr Lys Asn Tyr Leu Met Asn Ser Pro His Tyr Leu Glu
                580                 585                 590

Met Pro Ala Lys Met Gly Glu Asn Gly Ala Asn Gly Glu Asp Asn
            595                 600                 605

Gly Leu Trp Gly Cys Phe Thr Trp Gly Thr Thr Gln Gly Leu Gly Thr
            610                 615                 620

Ile Thr Leu Ala Leu Val Glu Asn Gly Leu Pro Ser Ala Asp Ile Gln
625                 630                 635                 640

Lys Ala Arg Asn Asn Ile Ala Lys Ala Ala Asp Lys Trp Leu Glu Asn
                645                 650                 655

Ile Glu Glu Gln Gly Tyr Arg Leu Pro Ile Lys Gln Ala Glu Asp Glu
                660                 665                 670

Arg Gly Gly Tyr Pro Trp Gly Ser Asn Ser Phe Ile Leu Asn Gln Met
            675                 680                 685

Ile Val Met Gly Tyr Ala Tyr Asp Phe Thr Gly Asn Ser Lys Tyr Leu
            690                 695                 700

Asp Gly Met Gln Asp Gly Met Ser Tyr Leu Leu Gly Arg Asn Gly Leu
705                 710                 715                 720

Asp Gln Ser Tyr Val Thr Gly Tyr Gly Glu Arg Pro Leu Gln Asn Pro
                725                 730                 735

His Asp Arg Phe Trp Thr Pro Gln Thr Ser Lys Lys Phe Pro Ala Pro
                740                 745                 750

Pro Pro Gly Ile Ile Ala Gly Gly Pro Asn Ser Arg Phe Glu Asp Pro
            755                 760                 765

Thr Ile Thr Ala Ala Val Lys Lys Asp Thr Pro Pro Gln Lys Cys Tyr
            770                 775                 780

Ile Asp His Thr Asp Ser Trp Ser Thr Asn Glu Ile Thr Ile Asn Trp
785                 790                 795                 800

Asn Ala Pro Phe Ala Trp Val Thr Ala Tyr Leu Asp Glu Ile Asp Leu
                805                 810                 815

Ile Thr Pro Pro Gly Gly Val Asp Pro Glu Pro Glu Val Ile Tyr
                820                 825                 830

Gly Asp Cys Asn Gly Asp Gly Lys Val Asn Ser Thr Asp Ala Val Ala
            835                 840                 845

Leu Lys Arg Tyr Ile Leu Arg Ser Gly Ile Ser Ile Asn Thr Asp Asn
850                 855                 860

```
Ala Asp Val Asn Ala Asp Gly Arg Val Asn Ser Thr Asp Leu Ala Ile
865                 870                 875                 880

Leu Lys Arg Tyr Ile Leu Lys Glu Ile Asp Val Leu Pro His Lys
            885                 890                 895

<210> SEQ ID NO 9
<211> LENGTH: 868
<212> TYPE: PRT
<213> ORGANISM: Clostridium thermocellum

<400> SEQUENCE: 9

Leu Glu Asp Lys Ser Pro Lys Leu Pro Asp Tyr Lys Asn Asp Leu Leu
1               5                   10                  15

Tyr Glu Arg Thr Phe Asp Glu Gly Leu Cys Phe Pro Trp His Thr Cys
            20                  25                  30

Glu Asp Ser Gly Gly Lys Cys Asp Phe Ala Val Val Asp Val Pro Gly
        35                  40                  45

Glu Pro Gly Asn Lys Ala Phe Arg Leu Thr Val Ile Asp Lys Gly Gln
    50                  55                  60

Asn Lys Trp Ser Val Gln Met Arg His Arg Gly Ile Thr Leu Glu Gln
65                  70                  75                  80

Gly His Thr Tyr Thr Val Arg Phe Thr Ile Trp Ser Asp Lys Ser Cys
                85                  90                  95

Arg Val Tyr Ala Lys Ile Gly Gln Met Gly Glu Pro Tyr Thr Glu Tyr
            100                 105                 110

Trp Asn Asn Asn Trp Asn Pro Phe Asn Leu Thr Pro Gly Gln Lys Leu
        115                 120                 125

Thr Val Glu Gln Asn Phe Thr Met Asn Tyr Pro Thr Asp Asp Thr Cys
    130                 135                 140

Glu Phe Thr Phe His Leu Gly Gly Glu Leu Ala Ala Gly Thr Pro Tyr
145                 150                 155                 160

Tyr Val Tyr Leu Asp Asp Val Ser Leu Tyr Asp Pro Arg Phe Val Lys
                165                 170                 175

Pro Val Glu Tyr Val Leu Pro Gln Pro Asp Val Arg Val Asn Gln Val
            180                 185                 190

Gly Tyr Leu Pro Phe Ala Lys Lys Tyr Ala Thr Val Val Ser Ser Ser
        195                 200                 205

Thr Ser Pro Leu Lys Trp Gln Leu Leu Asn Ser Ala Asn Gln Val Val
    210                 215                 220

Leu Glu Gly Asn Thr Ile Pro Lys Gly Leu Asp Lys Asp Ser Gln Asp
225                 230                 235                 240

Tyr Val His Trp Ile Asp Phe Ser Asn Phe Lys Thr Glu Gly Lys Gly
                245                 250                 255

Tyr Tyr Phe Lys Leu Pro Thr Val Asn Ser Asp Thr Asn Tyr Ser His
            260                 265                 270

Pro Phe Asp Ile Ser Ala Asp Ile Tyr Ser Lys Met Lys Phe Asp Ala
        275                 280                 285

Leu Ala Phe Phe Tyr His Lys Arg Ser Gly Ile Pro Ile Glu Met Pro
    290                 295                 300

Tyr Ala Gly Gly Glu Gln Trp Thr Arg Pro Ala Gly His Ile Gly Val
305                 310                 315                 320

Ala Pro Asn Lys Gly Asp Thr Asn Val Pro Thr Trp Pro Gln Asp Asp
                325                 330                 335

Glu Tyr Ala Gly Arg Pro Gln Lys Tyr Tyr Thr Lys Asp Val Thr Gly
```

-continued

```
            340                 345                 350
Gly Trp Tyr Asp Ala Gly Asp His Gly Lys Tyr Val Asn Gly Gly
        355                 360                 365

Ile Ala Val Trp Thr Leu Met Asn Met Tyr Glu Arg Ala Lys Ile Arg
    370                 375                 380

Gly Ile Ala Asn Gln Gly Ala Tyr Lys Asp Gly Gly Met Asn Ile Pro
385                 390                 395                 400

Glu Arg Asn Asn Gly Tyr Pro Asp Ile Leu Asp Glu Ala Arg Trp Glu
                405                 410                 415

Ile Glu Phe Phe Lys Lys Met Gln Val Thr Glu Lys Glu Asp Pro Ser
            420                 425                 430

Ile Ala Gly Met Val His His Lys Ile His Asp Phe Arg Trp Thr Ala
        435                 440                 445

Leu Gly Met Leu Pro His Glu Asp Pro Gln Pro Arg Tyr Leu Arg Pro
    450                 455                 460

Val Ser Thr Ala Ala Thr Leu Asn Phe Ala Ala Thr Leu Ala Gln Ser
465                 470                 475                 480

Ala Arg Leu Trp Lys Asp Tyr Asp Pro Thr Phe Ala Ala Asp Cys Leu
                485                 490                 495

Glu Lys Ala Glu Ile Ala Trp Gln Ala Ala Leu Lys His Pro Asp Ile
            500                 505                 510

Tyr Ala Glu Tyr Thr Pro Gly Ser Gly Gly Pro Gly Gly Pro Tyr
        515                 520                 525

Asn Asp Asp Tyr Val Gly Asp Glu Phe Tyr Trp Ala Ala Cys Glu Leu
    530                 535                 540

Tyr Val Thr Thr Gly Lys Asp Glu Tyr Lys Asn Tyr Leu Met Asn Ser
545                 550                 555                 560

Pro His Tyr Leu Glu Met Pro Ala Lys Met Gly Glu Asn Gly Gly Ala
                565                 570                 575

Asn Gly Glu Asp Asn Gly Leu Trp Gly Cys Phe Thr Trp Gly Thr Thr
            580                 585                 590

Gln Gly Leu Gly Thr Ile Thr Leu Ala Leu Val Glu Asn Gly Leu Pro
        595                 600                 605

Ser Ala Asp Ile Gln Lys Ala Arg Asn Asn Ile Ala Lys Ala Ala Asp
    610                 615                 620

Lys Trp Leu Glu Asn Ile Glu Glu Gln Gly Tyr Arg Leu Pro Ile Lys
625                 630                 635                 640

Gln Ala Glu Asp Glu Arg Gly Gly Tyr Pro Trp Gly Ser Asn Ser Phe
                645                 650                 655

Ile Leu Asn Gln Met Ile Val Met Gly Tyr Ala Tyr Asp Phe Thr Gly
            660                 665                 670

Asn Ser Lys Tyr Leu Asp Gly Met Gln Asp Gly Met Ser Tyr Leu Leu
        675                 680                 685

Gly Arg Asn Gly Leu Asp Gln Ser Tyr Val Thr Gly Tyr Gly Glu Arg
    690                 695                 700

Pro Leu Gln Asn Pro His Asp Arg Phe Trp Thr Pro Gln Thr Ser Lys
705                 710                 715                 720

Lys Phe Pro Ala Pro Pro Gly Ile Ile Ala Gly Gly Pro Asn Ser
                725                 730                 735

Arg Phe Glu Asp Pro Thr Ile Thr Ala Ala Val Lys Lys Asp Thr Pro
            740                 745                 750

Pro Gln Lys Cys Tyr Ile Asp His Thr Asp Ser Trp Ser Thr Asn Glu
        755                 760                 765
```

```
Ile Thr Ile Asn Trp Asn Ala Pro Phe Ala Trp Val Thr Ala Tyr Leu
    770                 775                 780
Asp Glu Ile Asp Leu Ile Thr Pro Pro Gly Gly Val Asp Pro Glu Glu
785                 790                 795                 800
Pro Glu Val Ile Tyr Gly Asp Cys Asn Gly Asp Gly Lys Val Asn Ser
                805                 810                 815
Thr Asp Ala Val Ala Leu Lys Arg Tyr Ile Leu Arg Ser Gly Ile Ser
                820                 825                 830
Ile Asn Thr Asp Asn Ala Asp Val Asn Ala Asp Gly Arg Val Asn Ser
            835                 840                 845
Thr Asp Leu Ala Ile Leu Lys Arg Tyr Ile Leu Lys Glu Ile Asp Val
    850                 855                 860
Leu Pro His Lys
865

<210> SEQ ID NO 10
<211> LENGTH: 2703
<212> TYPE: DNA
<213> ORGANISM: Clostridium thermocellum

<400> SEQUENCE: 10
```

| | |
|---|---:|
| atgaaaaaaa ggcttttagt ttcttttttg gtgttaagca taattgtagg attactttct | 60 |
| tttcagtcgc ttggtaatta acacagtggt ttaaaaatcg gtgcttgggt gggaacccag | 120 |
| ccgtcagaat cagcaattaa gagttttcag gaacttcagg gtagaaagct tgatattgtc | 180 |
| caccagttta ttaactggtc aactgatttt tcctgggtaa gaccttatgc cgacgctgtt | 240 |
| tataataacg gctcaatatt aatgattacc tgggaacctt gggaatacaa cactgtagat | 300 |
| atcaaaaacg gtaaagcgga tgcttacata accagaatgg cgcaagatat gaaagcctat | 360 |
| ggcaaggaaa tttggttaag acctcttcat gaagccaacg gagactggta ccatgggcc | 420 |
| ataggatatt cttcaagagt aaacacaaac gaaacttaca tagccgcttt cagacatatt | 480 |
| gtcgatattt tccgtgccaa cggagccacc aacgtcaaat gggtgtttaa tgtaaactgc | 540 |
| gacaatgtag gtaacggcac aagttatctg ggtcattatc ccggagataa ttatgtagac | 600 |
| tacacctcaa ttgacggata caactggggt accactcaaa gctggggaag ccaatggcaa | 660 |
| agctttgatc aggttttctc cagagcctac caagctttgg catcaataaa caaacccatc | 720 |
| attatagcag agtttgcatc agctgaaata ggcggaaaca aggcaagatg gattacagaa | 780 |
| gcatataact ctataagaac atcctacaac aaggtaattg ctgcagtatg gtttcacgag | 840 |
| aacaaagaaa ccgactggag aatcaactca gtcctgaagc ccttgcagc atacagggag | 900 |
| gcaataggag ccggttcatc aaatcctacc cctactccaa cttggacctc tactccacca | 960 |
| tcaagctcac caaaggctgt cgaccccttt gaaatggtta gaaaaatggg tatgggaaca | 1020 |
| aacctcggaa acactctcga agctccctat gaaggctcct ggtccaagtc tgccatggaa | 1080 |
| tattattttg atgattttaa agctgcagga tataaaaacg taagaatccc tgtaagatgg | 1140 |
| gacaaccata caatgaggac ataccccgtat accattgaca aagccttttt ggacagggtt | 1200 |
| gagcaagtgg ttgactggtc actttcaaga ggttttgtta caattataaa ttctcaccat | 1260 |
| gatgactgga tcaaggaaga ctataacgga acatagaac ggtttgaaaa gatatgggaa | 1320 |
| cagattgcgg aaaggtttaa aaacaaatcc gaaaatcttc tgtttgaaat catgaatgag | 1380 |
| cctttcggta acattacaga cgaacaaata gacgacatga acagcagaat attaaaaata | 1440 |
| atcagaaaga ccaatccaac ccgtattgtt ataataggcg gaggttattg gaacagttat | 1500 |

```
aatacgcttg taaacattaa aattcctgat gacccatact taatcggaac tttccattac    1560
tatgacccat atgaatttac tcacaagtgg agaggtactc ggggtactca ggaagacatg    1620
gatactgtag taagagtatt tgattttgtt aagagttggt ctgacagaaa caatatcccg    1680
gtatattttg gagaatttgc cgtaatggct tatgccgaca gaacttcccg tgtaaaatgg    1740 tatgattta  taagtgatgc ggccctggag cgcggttttg catgttccgt atgggataac    1800 ggcgttttg  gttcattgga taatgacatg gctatttaca acagagatac ccgtacccttt    1860 gacactgaaa tcctcaatgc actatttaat cccggaacat atccgtctta ttctccgaaa    1920
ccttcaccaa ctccaagacc gaccaaaccg cccgtaacac cggctgtcgg tgaaaaaatg    1980
ctggatgatt tgagggtgt  gttaaattgg ggttcatact ccggtgaagg tgcaaaagtt    2040
tcaacaaaaa ttgtgtccgg aaaaacagga acggcatgg  aagtcagcta caccgggaca    2100
acggacggct actggggaac agtatacagt ttaccggacg gcgattggtc aaaatggctt    2160
aaaatctctt tgacattaa  gtccgttgac ggttctgcca atgaaatcag atttatgatt    2220
gctgaaaaaa gcataaacgg tgtgggagac ggagaacact gggtttactc aataactccc    2280
gacagttcgt ggaaaactat agaaataccg ttctccagct ttagaagaag acttgattat    2340
cagccgcctg gacaggatat gagcggtact ttggatcttg acaatataga ttcaattcac    2400
ttcatgtatg ccaacaacaa gtcgggaaaa tttgtcgtag acaatatcaa gctgattggt    2460
gctacttccg atccgactcc ttcaataaaa cacggagatt tgaacttcga taatgcagtg    2520
aattctacag acttgttaat gcttaaaagg tatatcctca aatctttgga actcggtaca    2580
tctgagcagg aggaaaaatt caaaaaagcg gcagatttaa acagggacaa caaggtcgac    2640
tccactgact tgacaatttt gaaaagatac ttgctgaaag ccatcagtga aatacccata    2700
taa                                                                  2703
```

<210> SEQ ID NO 11
<211> LENGTH: 900
<212> TYPE: PRT
<213> ORGANISM: Clostridium thermocellum

<400> SEQUENCE: 11

```
Met Lys Lys Arg Leu Leu Val Ser Phe Leu Val Leu Ser Ile Ile Val
1               5                   10                  15

Gly Leu Leu Ser Phe Gln Ser Leu Gly Asn Tyr Asn Ser Gly Leu Lys
                20                  25                  30

Ile Gly Ala Trp Val Gly Thr Gln Pro Ser Glu Ser Ala Ile Lys Ser
            35                  40                  45

Phe Gln Glu Leu Gln Gly Arg Lys Leu Asp Ile Val His Gln Phe Ile
        50                  55                  60

Asn Trp Ser Thr Asp Phe Ser Trp Val Arg Pro Tyr Ala Asp Ala Val
65                  70                  75                  80

Tyr Asn Asn Gly Ser Ile Leu Met Ile Thr Trp Glu Pro Trp Glu Tyr
                85                  90                  95

Asn Thr Val Asp Ile Lys Asn Gly Lys Ala Asp Ala Tyr Ile Thr Arg
                100                 105                 110

Met Ala Gln Asp Met Lys Ala Tyr Gly Lys Glu Ile Trp Leu Arg Pro
            115                 120                 125

Leu His Glu Ala Asn Gly Asp Trp Tyr Pro Trp Ala Ile Gly Tyr Ser
        130                 135                 140

Ser Arg Val Asn Thr Asn Glu Thr Tyr Ile Ala Ala Phe Arg His Ile
```

-continued

```
            145                 150                 155                 160
Val Asp Ile Phe Arg Ala Asn Gly Ala Thr Asn Val Lys Trp Val Phe
                    165                 170                 175
Asn Val Asn Cys Asp Asn Val Gly Asn Gly Thr Ser Tyr Leu Gly His
                180                 185                 190
Tyr Pro Gly Asp Asn Tyr Val Asp Tyr Thr Ser Ile Asp Gly Tyr Asn
            195                 200                 205
Trp Gly Thr Thr Gln Ser Trp Gly Ser Gln Trp Gln Ser Phe Asp Gln
        210                 215                 220
Val Phe Ser Arg Ala Tyr Gln Ala Leu Ala Ser Ile Asn Lys Pro Ile
225                 230                 235                 240
Ile Ile Ala Glu Phe Ala Ser Ala Glu Ile Gly Gly Asn Lys Ala Arg
                245                 250                 255
Trp Ile Thr Glu Ala Tyr Asn Ser Ile Arg Thr Ser Tyr Asn Lys Val
                260                 265                 270
Ile Ala Ala Val Trp Phe His Glu Asn Lys Glu Thr Asp Trp Arg Ile
            275                 280                 285
Asn Ser Ser Pro Glu Ala Leu Ala Ala Tyr Arg Glu Ala Ile Gly Ala
        290                 295                 300
Gly Ser Ser Asn Pro Thr Pro Thr Pro Thr Trp Thr Ser Thr Pro Pro
305                 310                 315                 320
Ser Ser Ser Pro Lys Ala Val Asp Pro Phe Glu Met Val Arg Lys Met
                325                 330                 335
Gly Met Gly Thr Asn Leu Gly Asn Thr Leu Glu Ala Pro Tyr Glu Gly
                340                 345                 350
Ser Trp Ser Lys Ser Ala Met Glu Tyr Tyr Phe Asp Phe Lys Ala
        355                 360                 365
Ala Gly Tyr Lys Asn Val Arg Ile Pro Val Arg Trp Asp Asn His Thr
        370                 375                 380
Met Arg Thr Tyr Pro Tyr Thr Ile Asp Lys Ala Phe Leu Asp Arg Val
385                 390                 395                 400
Glu Gln Val Val Asp Trp Ser Leu Ser Arg Gly Phe Val Thr Ile Ile
                405                 410                 415
Asn Ser His His Asp Asp Trp Ile Lys Glu Asp Tyr Asn Gly Asn Ile
                420                 425                 430
Glu Arg Phe Glu Lys Ile Trp Glu Gln Ile Ala Glu Arg Phe Lys Asn
            435                 440                 445
Lys Ser Glu Asn Leu Leu Phe Glu Ile Met Asn Glu Pro Phe Gly Asn
        450                 455                 460
Ile Thr Asp Glu Gln Ile Asp Asp Met Asn Ser Arg Ile Leu Lys Ile
465                 470                 475                 480
Ile Arg Lys Thr Asn Pro Thr Arg Ile Val Ile Gly Gly Tyr
                485                 490                 495
Trp Asn Ser Tyr Asn Thr Leu Val Asn Ile Lys Ile Pro Asp Asp Pro
                500                 505                 510
Tyr Leu Ile Gly Thr Phe His Tyr Tyr Asp Pro Tyr Glu Phe Thr His
            515                 520                 525
Lys Trp Arg Gly Thr Trp Gly Thr Gln Glu Asp Met Asp Thr Val Val
        530                 535                 540
Arg Val Phe Asp Phe Val Lys Ser Trp Ser Asp Arg Asn Asn Ile Pro
545                 550                 555                 560
Val Tyr Phe Gly Glu Phe Ala Val Met Ala Tyr Ala Asp Arg Thr Ser
                565                 570                 575
```

Arg Val Lys Trp Tyr Asp Phe Ile Ser Asp Ala Ala Leu Glu Arg Gly
            580                 585                 590

Phe Ala Cys Ser Val Trp Asp Asn Gly Val Phe Gly Ser Leu Asp Asn
        595                 600                 605

Asp Met Ala Ile Tyr Asn Arg Asp Thr Arg Thr Phe Asp Thr Glu Ile
610                 615                 620

Leu Asn Ala Leu Phe Asn Pro Gly Thr Tyr Pro Ser Tyr Ser Pro Lys
625                 630                 635                 640

Pro Ser Pro Thr Pro Arg Pro Thr Lys Pro Val Thr Pro Ala Val
            645                 650                 655

Gly Glu Lys Met Leu Asp Asp Phe Glu Gly Val Leu Asn Trp Gly Ser
            660                 665                 670

Tyr Ser Gly Glu Gly Ala Lys Val Ser Thr Lys Ile Val Ser Gly Lys
            675                 680                 685

Thr Gly Asn Gly Met Glu Val Ser Tyr Thr Gly Thr Thr Asp Gly Tyr
            690                 695                 700

Trp Gly Thr Val Tyr Ser Leu Pro Asp Gly Asp Trp Ser Lys Trp Leu
705                 710                 715                 720

Lys Ile Ser Phe Asp Ile Lys Ser Val Asp Gly Ser Ala Asn Glu Ile
                725                 730                 735

Arg Phe Met Ile Ala Glu Lys Ser Ile Asn Gly Val Gly Asp Gly Glu
            740                 745                 750

His Trp Val Tyr Ser Ile Thr Pro Asp Ser Ser Trp Lys Thr Ile Glu
            755                 760                 765

Ile Pro Phe Ser Ser Phe Arg Arg Leu Asp Tyr Gln Pro Pro Gly
            770                 775                 780

Gln Asp Met Ser Gly Thr Leu Asp Leu Asp Asn Ile Asp Ser Ile His
785                 790                 795                 800

Phe Met Tyr Ala Asn Asn Lys Ser Gly Lys Phe Val Val Asp Asn Ile
                805                 810                 815

Lys Leu Ile Gly Ala Thr Ser Asp Pro Thr Pro Ser Ile Lys His Gly
            820                 825                 830

Asp Leu Asn Phe Asp Asn Ala Val Asn Ser Thr Asp Leu Leu Met Leu
            835                 840                 845

Lys Arg Tyr Ile Leu Lys Ser Leu Glu Leu Gly Thr Ser Glu Gln Glu
850                 855                 860

Glu Lys Phe Lys Lys Ala Ala Asp Leu Asn Arg Asp Asn Lys Val Asp
865                 870                 875                 880

Ser Thr Asp Leu Thr Ile Leu Lys Arg Tyr Leu Leu Lys Ala Ile Ser
            885                 890                 895

Glu Ile Pro Ile
            900

<210> SEQ ID NO 12
<211> LENGTH: 855
<212> TYPE: PRT
<213> ORGANISM: Clostridium thermocellum

<400> SEQUENCE: 12

Ile Lys Ser Phe Gln Glu Leu Gln Gly Arg Lys Leu Asp Ile Val His
1               5                   10                  15

Gln Phe Ile Asn Trp Ser Thr Asp Phe Ser Trp Val Arg Pro Tyr Ala
                20                  25                  30

Asp Ala Val Tyr Asn Asn Gly Ser Ile Leu Met Ile Thr Trp Glu Pro

```
                35                  40                  45
Trp Glu Tyr Asn Thr Val Asp Ile Lys Asn Gly Lys Ala Asp Ala Tyr
 50                  55                  60
Ile Thr Arg Met Ala Gln Asp Met Lys Ala Tyr Gly Lys Glu Ile Trp
 65                  70                  75                  80
Leu Arg Pro Leu His Glu Ala Asn Gly Asp Trp Tyr Pro Trp Ala Ile
                 85                  90                  95
Gly Tyr Ser Ser Arg Val Asn Thr Asn Glu Thr Tyr Ile Ala Ala Phe
                100                 105                 110
Arg His Ile Val Asp Ile Phe Arg Ala Asn Gly Ala Thr Asn Val Lys
                115                 120                 125
Trp Val Phe Asn Val Asn Cys Asp Asn Val Gly Asn Gly Thr Ser Tyr
                130                 135                 140
Leu Gly His Tyr Pro Gly Asp Asn Tyr Val Asp Tyr Thr Ser Ile Asp
145                 150                 155                 160
Gly Tyr Asn Trp Gly Thr Thr Gln Ser Trp Gly Ser Gln Trp Gln Ser
                165                 170                 175
Phe Asp Gln Val Phe Ser Arg Ala Tyr Gln Ala Leu Ala Ser Ile Asn
                180                 185                 190
Lys Pro Ile Ile Ile Ala Glu Phe Ala Ser Ala Glu Ile Gly Gly Asn
                195                 200                 205
Lys Ala Arg Trp Ile Thr Glu Ala Tyr Asn Ser Ile Arg Thr Ser Tyr
210                 215                 220
Asn Lys Val Ile Ala Ala Val Trp Phe His Glu Asn Lys Glu Thr Asp
225                 230                 235                 240
Trp Arg Ile Asn Ser Ser Pro Glu Ala Leu Ala Ala Tyr Arg Glu Ala
                245                 250                 255
Ile Gly Ala Gly Ser Ser Asn Pro Thr Pro Thr Pro Thr Trp Thr Ser
                260                 265                 270
Thr Pro Pro Ser Ser Ser Pro Lys Ala Val Asp Pro Phe Glu Met Val
                275                 280                 285
Arg Lys Met Gly Met Gly Thr Asn Leu Gly Asn Thr Leu Glu Ala Pro
290                 295                 300
Tyr Glu Gly Ser Trp Ser Lys Ser Ala Met Glu Tyr Tyr Phe Asp Asp
305                 310                 315                 320
Phe Lys Ala Ala Gly Tyr Lys Asn Val Arg Ile Pro Val Arg Trp Asp
                325                 330                 335
Asn His Thr Met Arg Thr Tyr Pro Tyr Thr Ile Asp Lys Ala Phe Leu
                340                 345                 350
Asp Arg Val Glu Gln Val Val Asp Trp Ser Leu Ser Arg Gly Phe Val
                355                 360                 365
Thr Ile Ile Asn Ser His His Asp Asp Trp Ile Lys Glu Asp Tyr Asn
                370                 375                 380
Gly Asn Ile Glu Arg Phe Glu Lys Ile Trp Glu Gln Ile Ala Glu Arg
385                 390                 395                 400
Phe Lys Asn Lys Ser Glu Asn Leu Leu Phe Glu Ile Met Asn Glu Pro
                405                 410                 415
Phe Gly Asn Ile Thr Asp Glu Gln Ile Asp Asp Met Asn Ser Arg Ile
                420                 425                 430
Leu Lys Ile Ile Arg Lys Thr Asn Pro Thr Arg Ile Val Ile Ile Gly
                435                 440                 445
Gly Gly Tyr Trp Asn Ser Tyr Asn Thr Leu Val Asn Ile Lys Ile Pro
450                 455                 460
```

```
Asp Asp Pro Tyr Leu Ile Gly Thr Phe His Tyr Asp Pro Tyr Glu
465                 470                 475                 480

Phe Thr His Lys Trp Arg Gly Thr Trp Gly Thr Gln Glu Asp Met Asp
                485                 490                 495

Thr Val Val Arg Val Phe Asp Phe Val Lys Ser Trp Ser Asp Arg Asn
            500                 505                 510

Asn Ile Pro Val Tyr Phe Gly Glu Phe Ala Val Met Ala Tyr Ala Asp
        515                 520                 525

Arg Thr Ser Arg Val Lys Trp Tyr Asp Phe Ile Ser Asp Ala Ala Leu
    530                 535                 540

Glu Arg Gly Phe Ala Cys Ser Val Trp Asp Asn Gly Val Phe Gly Ser
545                 550                 555                 560

Leu Asp Asn Asp Met Ala Ile Tyr Asn Arg Asp Thr Arg Thr Phe Asp
                565                 570                 575

Thr Glu Ile Leu Asn Ala Leu Phe Asn Pro Gly Thr Tyr Pro Ser Tyr
            580                 585                 590

Ser Pro Lys Pro Ser Pro Thr Pro Arg Pro Thr Lys Pro Pro Val Thr
        595                 600                 605

Pro Ala Val Gly Glu Lys Met Leu Asp Asp Phe Glu Gly Val Leu Asn
    610                 615                 620

Trp Gly Ser Tyr Ser Gly Glu Gly Ala Lys Val Ser Thr Lys Ile Val
625                 630                 635                 640

Ser Gly Lys Thr Gly Asn Gly Met Glu Val Ser Tyr Thr Gly Thr Thr
                645                 650                 655

Asp Gly Tyr Trp Gly Thr Val Tyr Ser Leu Pro Asp Gly Asp Trp Ser
            660                 665                 670

Lys Trp Leu Lys Ile Ser Phe Asp Ile Lys Ser Val Asp Gly Ser Ala
        675                 680                 685

Asn Glu Ile Arg Phe Met Ile Ala Gly Lys Ser Ile Asn Gly Val Gly
    690                 695                 700

Asp Gly Glu His Trp Val Tyr Ser Ile Thr Pro Asp Ser Ser Trp Lys
705                 710                 715                 720

Thr Ile Glu Ile Pro Phe Ser Ser Phe Arg Arg Leu Asp Tyr Gln
                725                 730                 735

Pro Pro Gly Gln Asp Met Ser Gly Thr Leu Asp Leu Asp Asn Ile Asp
            740                 745                 750

Ser Ile His Phe Met Tyr Ala Asn Asn Lys Ser Gly Lys Phe Val Val
        755                 760                 765

Asp Asn Ile Lys Leu Ile Gly Ala Thr Ser Asp Pro Thr Pro Ser Ile
    770                 775                 780

Lys His Gly Asp Leu Asn Phe Asp Asn Ala Val Asn Ser Thr Asp Leu
785                 790                 795                 800

Leu Met Leu Lys Arg Tyr Ile Leu Lys Ser Leu Glu Leu Gly Thr Ser
                805                 810                 815

Glu Gln Glu Glu Lys Phe Lys Lys Ala Ala Asp Leu Asn Arg Asp Asn
            820                 825                 830

Lys Val Asp Ser Thr Asp Leu Thr Ile Leu Lys Arg Tyr Leu Leu Lys
        835                 840                 845

Ala Ile Ser Glu Ile Pro Ile
850                 855

<210> SEQ ID NO 13
<211> LENGTH: 3129
```

```
<212> TYPE: DNA
<213> ORGANISM: Dictoglomus turgidum

<400> SEQUENCE: 13
```

| | | | | | |
|---|---|---|---|---|---|
| atgaagagaa | ttttagcttt | ttctctactc | tttattataa | tttccctaat | ctccttaagc | 60 |
| ttttcccaag | acattccttt | aaatatctat | gatccaaagg | tacaaaaagt | agaaagacca | 120 |
| ttatacttag | ccattatatg | gcataaccac | cagcctttat | attatgatcc | agatcaaaat | 180 |
| ataaatatcc | ttccttgggt | aaggatgcat | gcaataaaag | attactatga | catggcatac | 240 |
| atattaaaaa | actatcccca | aataaaagct | aattttaaca | tggttccatc | tctcttatat | 300 |
| caattagaac | tttataccaa | gaagggcata | aaggataaat | atctaattct | cacagaaaaa | 360 |
| cctgcagatc | aacttaccat | tgaagataaa | gaatttatat | taagaagatt | ctttgacgtt | 420 |
| aattgggata | gaataatcaa | aaaattccca | agatattggg | aacttttgaa | taaaagaggc | 480 |
| caatctgttg | acgatgtggt | aatagcaaaa | gcaattcaga | aatttacaac | tcaagatttt | 540 |
| agagatctac | aagtatggtt | caatttagca | tggtttgatc | ctgattttca | aaagtatgac | 600 |
| aaagatctat | caagacttat | agaaaaaggt | aaaaacttta | ctgaagaaga | taaaaaagtg | 660 |
| gtaataaaca | acaatatga | aattatgtct | aagattattc | ctctttatgc | ggaactacaa | 720 |
| aaaaccaaac | aaatagaagt | aactactact | ccattttcc | atccaataat | gccattatta | 780 |
| gtggacataa | aatctgccaa | aattgcagta | caagacatag | ctctacctaa | tgccacaata | 840 |
| aactacagtg | atgatacatc | agctcaactt | tcaatggctg | ttaactacta | taaaaaattt | 900 |
| ttcaaagata | caccaaaggg | tctttggcct | tccgaaggat | ccgtaagcca | agacattatt | 960 |
| cccatcgtag | gaaattcagg | cttttatgg | atggcaagtg | atgaggatgt | gctttcaaaa | 1020 |
| tctctaaaca | ctcctatcct | cagagactca | agaggaaatg | taacgaatcc | tgatgtactt | 1080 |
| tatcaacctt | acatagtgga | agaacaaggt | aaaaaggttt | atgtggtgtt | tagagacaaa | 1140 |
| aatctttcag | ataaaattgg | ttttgtctat | agtggaatga | aggagaaaa | tgcagcaaaa | 1200 |
| gactttgtaa | accgcttaga | gaatatctat | gagagagtaa | aggatgacaa | aaagtcatat | 1260 |
| ctcgtaacag | taatacttga | cggtgaaaac | tgttgggaat | attatgaaaa | cgatggaaag | 1320 |
| gaattttttaa | acactcttta | taaattactc | acagacagtc | cttatattga | aacagtaagg | 1380 |
| ctaacagact | acttaaataa | attccctccc | actaagaaga | tagaaaggct | ccattcagga | 1440 |
| tcttggatag | atggcacttt | cttaacttgg | gtaggagaac | aagaagaaaa | caagcatgg | 1500 |
| gaaatcttag | ataaagcaag | gacagagtta | atatatgaaa | cagtgaaaca | gaagaaaact | 1560 |
| atatctcccg | tattaaatcc | agatctctta | agaaacaata | tcgaaaaagc | atggtttgaa | 1620 |
| ctatatgcag | cagaaggtag | tgactggttc | tggtggtatg | gagatgatca | agactccaca | 1680 |
| aatgaccttg | cctttgatga | actctttagg | aaacatctta | taaatgtcta | caattaatt | 1740 |
| ggtaaagaag | ttcctcaaga | attgttcctt | cctatagtaa | aaataggtga | agaaaaacca | 1800 |
| gtacaaagct | tacaagcaaa | attcacacct | aagattgatg | gactgattaa | tcccgaagac | 1860 |
| gaatggaaga | acgctgcaat | ctaccttgct | aaaaaaggaa | caggactttc | cacaaagcca | 1920 |
| agtgattta | ttgaaaaagt | atacttaggt | cttgacaatg | ataatgtata | ctttcttata | 1980 |
| gagtcaaaaa | caaatctcaa | agactattta | ggaaagcctt | attttcttagc | agtgtacttt | 2040 |
| tctaatccaa | accaaaagga | atataatttg | tatccaagaa | agggaagtca | gactctcggg | 2100 |
| tatggaatag | cttacgaact | tctaattgat | ttttcaaaga | tcagctccct | tggagaagta | 2160 |
| gatgccatat | taaatcaagc | tactggtaat | aattcctgga | gacaacaatc | tacactaaaa | 2220 |

```
gcaggagtat cggagaaata catagaagta ggcgtacctt tcaaggaaat taaagtacaa    2280
ggaagagaac aaatagcaat gaatgtgata tttgggaaag aagaaccgat agatgtggta    2340
ccttactatg ttcctattta cttaactgtt cctgagaaga agttagaaat aacatacttc    2400
tctattgatg atccaactgg ggatgactat ggatggggca agttgtata tccaacagct     2460
ccagtattta aacccggtgt tttcgacata atccatgtag aaatgggtaa aagcaaagat    2520
gatattgtat tcaaaattaa gattagagga gatttagaaa atccatgggg ttcgcccaca    2580
ggagtctcag ttcaaaccat agacatatat attaatgatg aaaagagag cacctattac     2640
tatcaagcct tacctggaag acaagctaat attcctgagg gttggaacaa agcaatttgg    2700
gctgaaggat ggatacaaga attaataatt cctacattag atgagaaagg aaaagtacaa    2760
ctaaaagaga taaaaggagt agtacaatta agcaccgatc ctacagaaag aactataata    2820
atctcagtac ctgaaaaata cttaggtcct gtaacacctg actggaaaat cctcgtgata    2880
ttatgtggac aagaaggata cccaagacct ggaagctgga gagtaagaga agtagaagaa    2940
gaagctaaac aatggagatt tggcggtggg gacgacttct acggcgatcc taatatcata    3000
gatatgattg ttccccctgg aatgaaacaa gaggatatac tgtctaaatg ggtaagtagt    3060
gaagatgagg aagaaaatgt ttatgtgaaa ttacccttga tccccttag ggttttaatg      3120
tctcaataa                                                          3129
```

<210> SEQ ID NO 14
<211> LENGTH: 1042
<212> TYPE: PRT
<213> ORGANISM: Dictyoglomus turgidum

<400> SEQUENCE: 14

Met Lys Arg Ile Leu Ala Phe Ser Leu Leu Phe Ile Ile Ile Ser Leu
1               5                   10                  15

Ile Ser Leu Ser Phe Ser Gln Asp Ile Pro Leu Asn Ile Tyr Asp Pro
            20                  25                  30

Lys Val Gln Lys Val Glu Arg Pro Leu Tyr Leu Ala Ile Ile Trp His
        35                  40                  45

Asn His Gln Pro Leu Tyr Tyr Asp Pro Asp Gln Asn Ile Asn Ile Leu
    50                  55                  60

Pro Trp Val Arg Met His Ala Ile Lys Asp Tyr Tyr Asp Met Ala Tyr
65                  70                  75                  80

Ile Leu Lys Asn Tyr Pro Gln Ile Lys Ala Asn Phe Asn Met Val Pro
                85                  90                  95

Ser Leu Leu Tyr Gln Leu Glu Leu Tyr Thr Lys Lys Gly Ile Lys Asp
            100                 105                 110

Lys Tyr Leu Ile Leu Thr Glu Lys Pro Ala Asp Gln Leu Thr Ile Glu
        115                 120                 125

Asp Lys Glu Phe Ile Leu Arg Arg Phe Phe Asp Val Asn Trp Asp Arg
    130                 135                 140

Ile Ile Lys Lys Phe Pro Arg Tyr Trp Glu Leu Leu Asn Lys Arg Gly
145                 150                 155                 160

Gln Ser Val Asp Asp Val Val Ile Ala Lys Ala Ile Gln Lys Phe Thr
                165                 170                 175

Thr Gln Asp Phe Arg Asp Leu Gln Val Trp Phe Asn Leu Ala Trp Phe
            180                 185                 190

Asp Pro Asp Phe Gln Lys Tyr Asp Lys Asp Leu Ser Arg Leu Ile Glu
        195                 200                 205

```
Lys Gly Lys Asn Phe Thr Glu Glu Asp Lys Lys Val Ile Asn Lys
    210                 215                 220
Gln Tyr Glu Ile Met Ser Lys Ile Ile Pro Leu Tyr Ala Glu Leu Gln
225                 230                 235                 240
Lys Thr Lys Gln Ile Glu Val Thr Thr Thr Pro Phe Phe His Pro Ile
                    245                 250                 255
Met Pro Leu Leu Val Asp Ile Lys Ser Ala Lys Ile Ala Val Gln Asp
            260                 265                 270
Ile Ala Leu Pro Asn Ala Thr Ile Asn Tyr Ser Asp Asp Thr Ser Ala
                275                 280                 285
Gln Leu Ser Met Ala Val Asn Tyr Tyr Lys Lys Phe Phe Lys Asp Thr
    290                 295                 300
Pro Lys Gly Leu Trp Pro Ser Glu Gly Ser Val Ser Gln Asp Ile Ile
305                 310                 315                 320
Pro Ile Val Gly Asn Ser Gly Phe Leu Trp Met Ala Ser Asp Glu Asp
                    325                 330                 335
Val Leu Ser Lys Ser Leu Asn Thr Pro Ile Leu Arg Asp Ser Arg Gly
            340                 345                 350
Asn Val Thr Asn Pro Asp Val Leu Tyr Gln Pro Tyr Ile Val Glu Glu
                355                 360                 365
Gln Gly Lys Lys Val Tyr Val Phe Arg Asp Lys Asn Leu Ser Asp
    370                 375                 380
Lys Ile Gly Phe Val Tyr Ser Gly Met Lys Gly Glu Asn Ala Ala Lys
385                 390                 395                 400
Asp Phe Val Asn Arg Leu Glu Asn Ile Tyr Glu Arg Val Lys Asp Asp
                    405                 410                 415
Lys Lys Ser Tyr Leu Val Thr Val Ile Leu Asp Gly Glu Asn Cys Trp
            420                 425                 430
Glu Tyr Tyr Glu Asn Asp Gly Lys Glu Phe Leu Asn Thr Leu Tyr Lys
                435                 440                 445
Leu Leu Thr Asp Ser Pro Tyr Ile Glu Thr Val Arg Leu Thr Asp Tyr
    450                 455                 460
Leu Asn Lys Phe Pro Pro Thr Lys Lys Ile Glu Arg Leu His Ser Gly
465                 470                 475                 480
Ser Trp Ile Asp Gly Thr Phe Leu Thr Trp Val Gly Glu Gln Glu Glu
                    485                 490                 495
Asn Lys Ala Trp Glu Ile Leu Asp Lys Ala Arg Thr Glu Leu Ile Tyr
            500                 505                 510
Glu Thr Val Lys Gln Lys Thr Ile Ser Pro Val Leu Asn Pro Asp
                515                 520                 525
Leu Leu Arg Asn Asn Ile Glu Lys Ala Trp Phe Glu Leu Tyr Ala Ala
    530                 535                 540
Glu Gly Ser Asp Trp Phe Trp Trp Tyr Gly Asp Asp Gln Asp Ser Thr
545                 550                 555                 560
Asn Asp Leu Ala Phe Asp Glu Leu Phe Arg Lys His Leu Ile Asn Val
                    565                 570                 575
Tyr Lys Leu Ile Gly Lys Glu Val Pro Gln Glu Leu Phe Leu Pro Ile
            580                 585                 590
Val Lys Ile Gly Glu Glu Lys Pro Val Gln Ser Leu Gln Ala Lys Phe
                595                 600                 605
Thr Pro Lys Ile Asp Gly Leu Ile Asn Pro Glu Asp Glu Trp Lys Asn
    610                 615                 620
Ala Ala Ile Tyr Leu Ala Lys Lys Gly Thr Gly Leu Ser Thr Lys Pro
```

-continued

Ser Asp Phe Ile Glu Lys Val Tyr Leu Gly Leu Asp Asn Asp Asn Val
625                 630                 635                 640

Tyr Phe Leu Ile Glu Ser Lys Thr Asn Leu Lys Asp Tyr Leu Gly Lys
        645                 650                 655

Pro Tyr Phe Leu Ala Val Tyr Phe Ser Asn Pro Asn Gln Lys Glu Tyr
                660                 665                 670

Asn Leu Tyr Pro Arg Lys Gly Ser Gln Thr Leu Gly Tyr Gly Ile Ala
        675                 680                 685

Tyr Glu Leu Leu Ile Asp Phe Ser Lys Ile Ser Ser Leu Gly Glu Val
690                 695                 700

Asp Ala Ile Leu Asn Gln Ala Thr Gly Asn Asn Ser Trp Arg Gln Gln
705                 710                 715                 720

Ser Thr Leu Lys Ala Gly Val Ser Glu Lys Tyr Ile Glu Val Gly Val
        725                 730                 735

Pro Phe Lys Glu Ile Lys Val Gln Gly Arg Glu Gln Ile Ala Met Asn
                740                 745                 750

Val Ile Phe Gly Lys Glu Glu Pro Ile Asp Val Val Pro Tyr Tyr Val
        755                 760                 765

Pro Ile Tyr Leu Thr Val Pro Glu Lys Lys Leu Glu Ile Thr Tyr Phe
770                 775                 780

Ser Ile Asp Asp Pro Thr Gly Asp Tyr Gly Trp Gly Lys Val Val
785                 790                 795                 800

Tyr Pro Thr Ala Pro Val Phe Lys Pro Gly Val Phe Asp Ile Ile His
        805                 810                 815

Val Glu Met Gly Lys Ser Lys Asp Asp Ile Val Phe Lys Ile Lys Ile
                820                 825                 830

Arg Gly Asp Leu Glu Asn Pro Trp Gly Ser Pro Thr Gly Val Ser Val
        835                 840                 845

Gln Thr Ile Asp Ile Tyr Ile Asn Asp Gly Lys Glu Ser Thr Tyr Tyr
850                 855                 860

Tyr Gln Ala Leu Pro Gly Arg Gln Ala Asn Ile Pro Glu Gly Trp Asn
865                 870                 875                 880

Lys Ala Ile Trp Ala Glu Gly Trp Ile Gln Glu Leu Ile Ile Pro Thr
        885                 890                 895

Leu Asp Glu Lys Gly Lys Val Gln Leu Lys Glu Ile Lys Gly Val Val
                900                 905                 910

Gln Leu Ser Thr Asp Pro Thr Glu Arg Thr Ile Ile Ser Val Pro
        915                 920                 925

Glu Lys Tyr Leu Gly Pro Val Thr Pro Asp Trp Lys Ile Leu Val Ile
930                 935                 940

Leu Cys Gly Gln Glu Gly Tyr Pro Arg Pro Gly Ser Trp Arg Val Arg
945                 950                 955                 960

Glu Val Glu Glu Glu Ala Lys Gln Trp Arg Phe Gly Gly Gly Asp Asp
        965                 970                 975

Phe Tyr Gly Asp Pro Asn Ile Ile Asp Met Ile Val Pro Pro Gly Met
                980                 985                 990

Lys Gln Glu Asp Ile Leu Ser Lys Trp Val Ser Ser Glu Asp Glu
        995                 1000                1005

Glu Glu Asn Val Tyr Val Glu Leu Pro Leu Ile Pro Leu Arg Val
1010                1015                1020

Leu Met Ser Gln
        1025                1030                1035

1040

<210> SEQ ID NO 15
<211> LENGTH: 1019
<212> TYPE: PRT
<213> ORGANISM: Dictyoglomus turgidum

<400> SEQUENCE: 15

```
Asp Ile Pro Leu Asn Ile Tyr Asp Pro Lys Val Gln Lys Val Glu Arg
1               5                   10                  15

Pro Leu Tyr Leu Ala Ile Ile Trp His Asn His Gln Pro Leu Tyr Tyr
            20                  25                  30

Asp Pro Asp Gln Asn Ile Asn Ile Leu Pro Trp Val Arg Met His Ala
        35                  40                  45

Ile Lys Asp Tyr Tyr Asp Met Ala Tyr Ile Leu Lys Asn Tyr Pro Gln
    50                  55                  60

Ile Lys Ala Asn Phe Asn Met Val Pro Ser Leu Leu Tyr Gln Leu Glu
65                  70                  75                  80

Leu Tyr Thr Lys Lys Gly Ile Lys Asp Lys Tyr Leu Ile Leu Thr Glu
                85                  90                  95

Lys Pro Ala Asp Gln Leu Thr Ile Glu Asp Lys Glu Phe Ile Leu Arg
            100                 105                 110

Arg Phe Phe Asp Val Asn Trp Asp Arg Ile Ile Lys Lys Phe Pro Arg
        115                 120                 125

Tyr Trp Glu Leu Leu Asn Lys Arg Gly Gln Ser Val Asp Asp Val Val
    130                 135                 140

Ile Ala Lys Ala Ile Gln Lys Phe Thr Thr Gln Asp Phe Arg Asp Leu
145                 150                 155                 160

Gln Val Trp Phe Asn Leu Ala Trp Phe Asp Pro Asp Phe Gln Lys Tyr
                165                 170                 175

Asp Lys Asp Leu Ser Arg Leu Ile Glu Lys Gly Lys Asn Phe Thr Glu
            180                 185                 190

Glu Asp Lys Lys Val Val Ile Asn Lys Gln Tyr Glu Ile Met Ser Lys
        195                 200                 205

Ile Ile Pro Leu Tyr Ala Glu Leu Gln Lys Thr Lys Gln Ile Glu Val
    210                 215                 220

Thr Thr Thr Pro Phe Phe His Pro Ile Met Pro Leu Leu Val Asp Ile
225                 230                 235                 240

Lys Ser Ala Lys Ile Ala Val Gln Asp Ile Ala Leu Pro Asn Ala Thr
                245                 250                 255

Ile Asn Tyr Ser Asp Asp Thr Ser Ala Gln Leu Ser Met Ala Val Asn
            260                 265                 270

Tyr Tyr Lys Lys Phe Phe Lys Asp Thr Pro Lys Gly Leu Trp Pro Ser
        275                 280                 285

Glu Gly Ser Val Ser Gln Asp Ile Ile Pro Ile Val Gly Asn Ser Gly
    290                 295                 300

Phe Leu Trp Met Ala Ser Asp Glu Asp Val Leu Ser Lys Ser Leu Asn
305                 310                 315                 320

Thr Pro Ile Leu Arg Asp Ser Arg Gly Asn Val Thr Asn Pro Asp Val
                325                 330                 335

Leu Tyr Gln Pro Tyr Ile Val Glu Gln Gly Lys Lys Val Tyr Val
            340                 345                 350

Val Phe Arg Asp Lys Asn Leu Ser Asp Lys Ile Gly Phe Val Tyr Ser
        355                 360                 365

Gly Met Lys Gly Glu Asn Ala Ala Lys Asp Phe Val Asn Arg Leu Glu
```

-continued

```
            370                 375                 380
Asn Ile Tyr Glu Arg Val Lys Asp Asp Lys Ser Tyr Leu Val Thr
385                 390                 395                 400

Val Ile Leu Asp Gly Glu Asn Cys Trp Glu Tyr Tyr Glu Asn Asp Gly
                405                 410                 415

Lys Glu Phe Leu Asn Thr Leu Tyr Lys Leu Leu Thr Asp Ser Pro Tyr
            420                 425                 430

Ile Glu Thr Val Arg Leu Thr Asp Tyr Leu Asn Lys Phe Pro Pro Thr
            435                 440                 445

Lys Lys Ile Glu Arg Leu His Ser Gly Ser Trp Ile Asp Gly Thr Phe
        450                 455                 460

Leu Thr Trp Val Gly Glu Gln Glu Glu Asn Lys Ala Trp Glu Ile Leu
465                 470                 475                 480

Asp Lys Ala Arg Thr Glu Leu Ile Tyr Glu Thr Val Lys Gln Lys Lys
                485                 490                 495

Thr Ile Ser Pro Val Leu Asn Pro Asp Leu Leu Arg Asn Asn Ile Glu
            500                 505                 510

Lys Ala Trp Phe Glu Leu Tyr Ala Ala Glu Gly Ser Asp Trp Phe Trp
        515                 520                 525

Trp Tyr Gly Asp Asp Gln Asp Ser Thr Asn Asp Leu Ala Phe Asp Glu
        530                 535                 540

Leu Phe Arg Lys His Leu Ile Asn Val Tyr Lys Leu Ile Gly Lys Glu
545                 550                 555                 560

Val Pro Gln Glu Leu Phe Leu Pro Ile Val Lys Ile Gly Glu Glu Lys
                565                 570                 575

Pro Val Gln Ser Leu Gln Ala Lys Phe Thr Pro Lys Ile Asp Gly Leu
            580                 585                 590

Ile Asn Pro Glu Asp Glu Trp Lys Asn Ala Ala Ile Tyr Leu Ala Lys
            595                 600                 605

Lys Gly Thr Gly Leu Ser Thr Lys Pro Ser Asp Phe Ile Glu Lys Val
        610                 615                 620

Tyr Leu Gly Leu Asp Asn Asp Asn Val Tyr Phe Leu Ile Glu Ser Lys
625                 630                 635                 640

Thr Asn Leu Lys Asp Tyr Leu Gly Lys Pro Tyr Phe Leu Ala Val Tyr
                645                 650                 655

Phe Ser Asn Pro Asn Gln Lys Glu Tyr Asn Leu Tyr Pro Arg Lys Gly
            660                 665                 670

Ser Gln Thr Leu Gly Tyr Gly Ile Ala Tyr Glu Leu Leu Ile Asp Phe
        675                 680                 685

Ser Lys Ile Ser Ser Leu Gly Glu Val Asp Ala Ile Leu Asn Gln Ala
        690                 695                 700

Thr Gly Asn Asn Ser Trp Arg Gln Gln Ser Thr Leu Lys Ala Gly Val
705                 710                 715                 720

Ser Glu Lys Tyr Ile Glu Val Gly Val Pro Phe Lys Glu Ile Lys Val
                725                 730                 735

Gln Gly Arg Glu Gln Ile Ala Met Asn Val Ile Phe Gly Lys Glu Glu
            740                 745                 750

Pro Ile Asp Val Val Pro Tyr Tyr Val Pro Ile Tyr Leu Thr Val Pro
            755                 760                 765

Glu Lys Lys Leu Glu Ile Thr Tyr Phe Ser Ile Asp Asp Pro Thr Gly
        770                 775                 780

Asp Asp Tyr Gly Trp Gly Lys Val Val Tyr Pro Thr Ala Pro Val Phe
785                 790                 795                 800
```

```
Lys Pro Gly Val Phe Asp Ile Ile His Val Glu Met Gly Lys Ser Lys
                805                 810                 815

Asp Asp Ile Val Phe Lys Ile Lys Ile Arg Gly Asp Leu Glu Asn Pro
            820                 825                 830

Trp Gly Ser Pro Thr Gly Val Ser Val Gln Thr Ile Asp Ile Tyr Ile
        835                 840                 845

Asn Asp Gly Lys Glu Ser Thr Tyr Tyr Tyr Gln Ala Leu Pro Gly Arg
    850                 855                 860

Gln Ala Asn Ile Pro Glu Gly Trp Asn Lys Ala Ile Trp Ala Glu Gly
865                 870                 875                 880

Trp Ile Gln Glu Leu Ile Ile Pro Thr Leu Asp Glu Lys Gly Lys Val
                885                 890                 895

Gln Leu Lys Glu Ile Lys Gly Val Val Gln Leu Ser Thr Asp Pro Thr
            900                 905                 910

Glu Arg Thr Ile Ile Ile Ser Val Pro Glu Lys Tyr Leu Gly Pro Val
        915                 920                 925

Thr Pro Asp Trp Lys Ile Leu Val Ile Leu Cys Gly Gln Glu Gly Tyr
    930                 935                 940

Pro Arg Pro Gly Ser Trp Arg Val Arg Glu Val Glu Glu Ala Lys
945                 950                 955                 960

Gln Trp Arg Phe Gly Gly Gly Asp Asp Phe Tyr Gly Asp Pro Asn Ile
                965                 970                 975

Ile Asp Met Ile Val Pro Pro Gly Met Lys Gln Glu Asp Ile Leu Ser
            980                 985                 990

Lys Trp Val Ser Ser Glu Asp Glu  Glu Glu Asn Val Tyr  Val Glu Leu
        995                 1000                1005

Pro Leu  Ile Pro Leu Arg Val  Leu Met Ser Gln
    1010                1015

<210> SEQ ID NO 16
<211> LENGTH: 1000
<212> TYPE: DNA
<213> ORGANISM: Bacillus stearothermophilus

<400> SEQUENCE: 16
gatcatcccc cgctcccttc tcctttgttt ggccaacttc cttctctcct ttcctttta       60 tattctttgt gcaatcgttt gcacaaaacg gttgatgcaa acgatttcat caatctttat    120
cttatacgaa taaacagaat atttcaacta tattttccac ttgttgaaaa acgaatcgtg    180
tcaaactcaa aattgtttaa attcgatatt gaaaacgatt acaaataaaa attataatag    240
acgtaaacgt tcgagggttt gctccctttt tactcttttt atccaatcgt ttccccttaat   300 tttttggaag ccaaaccgtc gaatgtaaca tttgattaag ggggaagggc attgtgctaa    360
cgtttcaccg catcattcga aaaggatgga tgttcctgct cgcgttttg ctcactgcct     420 cgctgttctg cccaacagga cagcacgcca aggctgccgc accgtttaac ggcaccatga    480
tgcagtattt tgaatggtac ttgccggatg atggcacgtt atggaccaaa gtggccaatg    540
aagccaacaa cttatccagc cttggcatca ccgctctttg gctgccgccc gcttacaaag    600
gaacaagccg cagcgacgta gggtacggag tatacgactt gtatgacctc ggcgaattca    660
atcaaaaagg gaccgtccgc acaaaatatg gaacaaaagc tcaatatctt caagccattc    720
aagccgccca cgccgctgga atgcaagtgt acgccgatgt cgtgttcgac cataaaggcg    780
gcgctgacgg cacggaatgg gtggacgccg tcgaagtcaa tccgtccgac cgcaaccaag    840
```

```
aaatctcggg cacctatcaa atccaagcat ggacgaaatt tgattttccc gggcggggca      900
acacctactc cagctttaag tggcgctggt accattttga cggcgttgat tgggacgaaa      960
gccgaaaatt aagccgcatt tacaaattcc gcggcatcgg                            1000
```

<210> SEQ ID NO 17
<211> LENGTH: 549
<212> TYPE: PRT
<213> ORGANISM: Bacillus stearothermophilus

<400> SEQUENCE: 17

```
Met Leu Thr Phe His Arg Ile Ile Arg Lys Gly Trp Met Phe Leu Leu
1               5                   10                  15

Ala Phe Leu Leu Thr Ala Leu Leu Phe Cys Pro Thr Gly Gln Pro Ala
            20                  25                  30

Lys Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
50                  55                  60

Asn Asn Leu Ser Ser Leu Gly Ile Thr Ala Leu Trp Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Ala Val Arg Thr Lys Tyr
            100                 105                 110

Gly Thr Lys Ala Gln Tyr Leu Gln Ala Ile Gln Ala Ala His Ala Ala
        115                 120                 125

Gly Met Gln Val Tyr Ala Asp Val Val Phe Asp His Lys Gly Gly Ala
130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Arg Gly Ile Gly Lys Ala Trp Asp Trp Glu Val Asp
210                 215                 220

Thr Glu Asn Gly Asn Tyr Asp Tyr Leu Met Tyr Ala Asp Leu Asp Met
225                 230                 235                 240

Asp His Pro Glu Val Val Thr Glu Leu Lys Ser Trp Gly Lys Trp Tyr
                245                 250                 255

Val Asn Thr Thr Asn Ile Asp Gly Phe Arg Leu Asp Ala Val Lys His
            260                 265                 270

Ile Lys Phe Ser Phe Phe Pro Asp Trp Leu Ser Asp Val Arg Ser Gln
        275                 280                 285

Thr Gly Lys Pro Leu Phe Thr Val Gly Glu Tyr Trp Ser Tyr Asp Ile
290                 295                 300

Asn Lys Leu His Asn Tyr Ile Met Lys Thr Asn Gly Thr Met Ser Leu
305                 310                 315                 320

Phe Asp Ala Pro Leu His Asn Lys Phe Tyr Thr Ala Ser Lys Ser Gly
                325                 330                 335

Gly Thr Phe Asp Met Arg Thr Leu Met Thr Asn Thr Leu Met Lys Asp
            340                 345                 350
```

```
Gln Pro Thr Leu Ala Val Thr Phe Val Asp Asn His Asp Thr Glu Pro
            355                 360                 365

Gly Gln Ala Leu Gln Ser Trp Val Asp Pro Trp Phe Lys Pro Leu Ala
370                 375                 380

Tyr Ala Phe Ile Leu Thr Arg Gln Glu Gly Tyr Pro Cys Val Phe Tyr
385                 390                 395                 400

Gly Asp Tyr Tyr Gly Ile Pro Gln Tyr Asn Ile Pro Ser Leu Lys Ser
                405                 410                 415

Lys Ile Asp Pro Leu Leu Ile Ala Arg Arg Asp Tyr Ala Tyr Gly Thr
            420                 425                 430

Gln His Asp Tyr Leu Asp His Ser Asp Ile Ile Gly Trp Thr Arg Glu
        435                 440                 445

Gly Val Thr Glu Lys Pro Gly Ser Gly Leu Ala Ala Leu Ile Thr Asp
450                 455                 460

Gly Pro Gly Gly Ser Lys Trp Met Tyr Val Gly Lys Gln His Ala Gly
465                 470                 475                 480

Lys Val Phe Tyr Asp Leu Thr Gly Asn Arg Ser Asp Thr Val Thr Ile
                485                 490                 495

Asn Ser Asp Gly Trp Gly Glu Phe Lys Val Asn Gly Ser Val Ser
            500                 505                 510

Val Trp Val Pro Arg Lys Thr Thr Val Ser Thr Ile Ala Trp Ser Ile
        515                 520                 525

Thr Thr Arg Pro Trp Thr Asp Glu Phe Val Arg Trp Thr Glu Pro Arg
530                 535                 540

Leu Val Ala Trp Pro
545

<210> SEQ ID NO 18
<211> LENGTH: 515
<212> TYPE: PRT
<213> ORGANISM: Bacillus stearothermophilus

<400> SEQUENCE: 18

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
```

```
                        165                 170                 175
Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Ser Trp Gly Lys Trp Tyr Val Asn
        210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp Pro
        515

<210> SEQ ID NO 19
<211> LENGTH: 1830
<212> TYPE: DNA
<213> ORGANISM: Gibberella zeae

<400> SEQUENCE: 19
atgatcaccc tgcccccaaa ggccactgcc cttgtggcac tcgcctgcgc tttgttcccc      60
gctgccacaa ctgccaaagc cgacggccca tacgaagcaa catgggaatc tacagacaaa     120
```

```
cacaacgccg caccagaatg gtaccgcgat gcaaaattcg gcgtttactg gcactgggga      180
gctttcacca ccgctcagta cgccagtgaa tggtatcctc gcaacatgta tgagcccgac      240
tccgaccagc gcaagcacca cacagaaacc tatgggccgc ctgaagaatg gggttatgag      300
aactttatca aaggtgccaa ggataaaaag gcaactttg tgcagttcaa acctgtcctc       360
aagtccaaag gtggtgaatt cgatcccgag gccattatca agatcgtcaa aggttctggt      420
gctcggtttg ctggacctgt ggctgaacat catgatggct ctccatgtg ggatagcaaa       480 gtcaatgagt ggaacccagt caactatggc cccaagctag acttggtcaa gctctgggct      540
gatcttgttc gtgagaatga tatgaaactt gttattgcta tgcatcaggc gtacaactac      600
aatggcttct ttcaatgggc gccaaagaca acgacacga gcctgcagaa gctactcggt       660
caacttcctc gcgatgagga agaccaactc tggttcgaca agcatcgcga gatgttggac      720
cacgttcagc ccgacatcat ctggaatgat ttctctctcg acagtccagg cgaatgcgga      780
agtttcgaag gtccttgtgc agtagacgag cagaaacgtc tcgagtttct tgcttactac      840
ttcaaccgag gcgaggagtg gggtaaagaa gttgtcacca cctacaagca ccacgaccat      900
ggcttccgca acacatcagc cgtggacgac tgggagcgtg gtggaccatc caaccttgtt      960
cgtccctatt ggcagaccga cgacgccatc agtgcttcaa gctggagcta cacagttggt     1020
atcaagtact acagctccaa agccatggtc cactctctgc ttgatcgcgt gagcaagaat     1080
ggtaacatgc tgctcaacat ttcacccatg gccaatggag tgctgcctga ggagcagatc     1140
aaggttttga cgacattgg tgacttcctc agccgttacg gcgaggctgt ttatgatact      1200
cgcgcttggg atatctatgg tgagggaccg aaccaggtcg aagtggatc tttcacagcg      1260 ccgttgcaag gaaacagcag cgatattcgc tttacgcgca acaaggaaga tgatgttctc     1320
tatgtcactg ttcttggttg gcctgaggac aaccttgttt cggtcaagaa ccttggatca     1380
aatgctttgg ttgatctcga atcgctcaag tctgttgagt tactcggcga caaggctggc     1440
gattatgtca aggtttctga atgggaacag tctaaggacg ccctggacat tactcttcct     1500
tcgcagcccg ctgagtctct cgcttatgtt ctcaagctta cctttgatgg tggaattcct     1560
gtgcctcagc ctgagcgtgg tgcagctgtc ttctccaagg cggatgctac tggaaagggc     1620
gttgcccttg cgttgggtac ttttgataca gttttcttga ctgaagctgg gctcaagcct     1680
gaggaaatcc gctccattcg agtgtcggat ggcacgaagg ctactctatt tagtggattc     1740
aggttcacgg gagagagcaa ggagctcagc gctggtgaac acgaggttga agatggctct     1800
gtgggctcta ttgtggtctc caagatttaa                                      1830
```

<210> SEQ ID NO 20
<211> LENGTH: 609
<212> TYPE: PRT
<213> ORGANISM: Gibberella zeae

<400> SEQUENCE: 20

Met Ile Thr Leu Pro Pro Lys Ala Thr Ala Leu Val Ala Leu Ala Cys
1               5                   10                  15

Ala Leu Phe Pro Ala Ala Thr Thr Ala Lys Ala Asp Gly Pro Tyr Glu
            20                  25                  30

Ala Thr Trp Glu Ser Thr Asp Lys His Asn Ala Ala Pro Glu Trp Tyr
        35                  40                  45

Arg Asp Ala Lys Phe Gly Val Tyr Trp His Trp Gly Ala Phe Thr Thr
    50                  55                  60

-continued

```
Ala Gln Tyr Ala Ser Glu Trp Tyr Pro Arg Asn Met Tyr Glu Pro Asp
 65                  70                  75                  80

Ser Asp Gln Arg Lys His His Thr Glu Thr Tyr Gly Pro Pro Glu Glu
                 85                  90                  95

Trp Gly Tyr Glu Asn Phe Ile Lys Gly Ala Lys Asp Lys Lys Gly Asn
            100                 105                 110

Phe Val Gln Phe Lys Pro Val Leu Lys Ser Lys Gly Gly Glu Phe Asp
        115                 120                 125

Pro Glu Ala Ile Ile Lys Ile Val Lys Gly Ser Gly Ala Arg Phe Ala
    130                 135                 140

Gly Pro Val Ala Glu His His Asp Gly Phe Ser Met Trp Asp Ser Lys
145                 150                 155                 160

Val Asn Glu Trp Asn Pro Val Asn Tyr Gly Pro Lys Leu Asp Leu Val
                165                 170                 175

Lys Leu Trp Ala Asp Leu Val Arg Glu Asn Asp Met Lys Leu Val Ile
            180                 185                 190

Ala Met His Gln Ala Tyr Asn Tyr Asn Gly Phe Phe Gln Trp Ala Pro
        195                 200                 205

Lys Thr Asn Asp Thr Ser Leu Gln Lys Leu Leu Gly Gln Leu Pro Arg
    210                 215                 220

Asp Glu Glu Asp Gln Leu Trp Phe Asp Lys His Arg Glu Met Leu Asp
225                 230                 235                 240

His Val Gln Pro Asp Ile Ile Trp Asn Asp Phe Ser Leu Asp Ser Pro
                245                 250                 255

Gly Glu Cys Gly Ser Phe Glu Gly Pro Cys Ala Val Asp Glu Gln Lys
            260                 265                 270

Arg Leu Glu Phe Leu Ala Tyr Tyr Phe Asn Arg Gly Glu Glu Trp Gly
        275                 280                 285

Lys Glu Val Val Thr Thr Tyr Lys His His Asp His Gly Phe Arg Asn
    290                 295                 300

Thr Ser Ala Val Asp Asp Trp Glu Arg Gly Gly Pro Ser Asn Leu Val
305                 310                 315                 320

Arg Pro Tyr Trp Gln Thr Asp Asp Ala Ile Ser Ala Ser Ser Trp Ser
                325                 330                 335

Tyr Thr Val Gly Ile Lys Tyr Tyr Ser Ser Lys Ala Met Val His Ser
            340                 345                 350

Leu Leu Asp Arg Val Ser Lys Asn Gly Asn Met Leu Leu Asn Ile Ser
        355                 360                 365

Pro Met Ala Asn Gly Val Leu Pro Glu Glu Gln Ile Lys Val Leu Asn
    370                 375                 380

Asp Ile Gly Asp Phe Leu Ser Arg Tyr Gly Glu Ala Val Tyr Asp Thr
385                 390                 395                 400

Arg Ala Trp Asp Ile Tyr Gly Glu Gly Pro Asn Gln Val Glu Gly Gly
                405                 410                 415

Ser Phe Thr Ala Pro Leu Gln Gly Asn Ser Ser Asp Ile Arg Phe Thr
            420                 425                 430

Arg Asn Lys Glu Asp Asp Val Leu Tyr Val Thr Val Leu Gly Trp Pro
        435                 440                 445

Glu Asp Asn Leu Val Ser Lys Asn Leu Gly Ser Asn Ala Leu Val
    450                 455                 460

Asp Leu Glu Ser Leu Lys Ser Val Glu Leu Leu Gly Asp Lys Ala Gly
465                 470                 475                 480

Asp Tyr Val Lys Val Ser Glu Trp Glu Gln Ser Lys Asp Ala Leu Asp
```

```
                    485                 490                 495
Ile Thr Leu Pro Ser Gln Pro Ala Glu Ser Leu Ala Tyr Val Leu Lys
                500                 505                 510
Leu Thr Phe Asp Gly Gly Ile Pro Val Pro Gln Pro Glu Arg Gly Ala
                515                 520                 525
Ala Val Phe Ser Lys Ala Asp Ala Thr Gly Lys Gly Val Ala Leu Ala
                530                 535                 540
Leu Gly Thr Phe Asp Thr Val Phe Leu Thr Glu Ala Gly Leu Lys Pro
545                 550                 555                 560
Glu Glu Ile Arg Ser Ile Arg Val Ser Asp Gly Thr Lys Ala Thr Leu
                565                 570                 575
Phe Ser Gly Phe Arg Phe Thr Gly Glu Ser Lys Glu Leu Ser Ala Gly
                580                 585                 590
Glu His Glu Val Glu Asp Gly Ser Val Gly Ser Ile Val Val Ser Lys
                595                 600                 605
Ile

<210> SEQ ID NO 21
<211> LENGTH: 584
<212> TYPE: PRT
<213> ORGANISM: Gibberella zeae

<400> SEQUENCE: 21

Lys Ala Asp Gly Pro Tyr Glu Ala Thr Trp Glu Ser Thr Asp Lys His
1               5                   10                  15
Asn Ala Ala Pro Glu Trp Tyr Arg Asp Ala Lys Phe Gly Val Tyr Trp
                20                  25                  30
His Trp Gly Ala Phe Thr Thr Ala Gln Tyr Ala Ser Glu Trp Tyr Pro
            35                  40                  45
Arg Asn Met Tyr Glu Pro Asp Ser Asp Gln Arg Lys His His Thr Glu
        50                  55                  60
Thr Tyr Gly Pro Pro Glu Glu Trp Gly Tyr Glu Asn Phe Ile Lys Gly
65                  70                  75                  80
Ala Lys Asp Lys Lys Gly Asn Phe Val Gln Phe Lys Pro Val Leu Lys
                85                  90                  95
Ser Lys Gly Gly Glu Phe Asp Pro Glu Ala Ile Ile Lys Ile Val Lys
                100                 105                 110
Gly Ser Gly Ala Arg Phe Ala Gly Pro Val Ala Glu His His Asp Gly
            115                 120                 125
Phe Ser Met Trp Asp Ser Lys Val Asn Glu Trp Asn Pro Val Asn Tyr
        130                 135                 140
Gly Pro Lys Leu Asp Leu Val Lys Leu Trp Ala Asp Leu Val Arg Glu
145                 150                 155                 160
Asn Asp Met Lys Leu Val Ile Ala Met His Gln Ala Tyr Asn Tyr Asn
                165                 170                 175
Gly Phe Phe Gln Trp Ala Pro Lys Thr Asn Asp Thr Ser Leu Gln Lys
                180                 185                 190
Leu Leu Gly Gln Leu Pro Arg Asp Glu Glu Asp Gln Leu Trp Phe Asp
            195                 200                 205
Lys His Arg Glu Met Leu Asp His Val Gln Pro Asp Ile Ile Trp Asn
        210                 215                 220
Asp Phe Ser Leu Asp Ser Pro Gly Glu Cys Gly Ser Phe Glu Gly Pro
225                 230                 235                 240
Cys Ala Val Asp Glu Gln Lys Arg Leu Glu Phe Leu Ala Tyr Tyr Phe
```

245                 250                 255
Asn Arg Gly Glu Glu Trp Gly Lys Glu Val Thr Thr Tyr Lys His
            260                 265                 270
His Asp His Gly Phe Arg Asn Thr Ser Ala Val Asp Asp Trp Glu Arg
        275                 280                 285
Gly Gly Pro Ser Asn Leu Val Arg Pro Tyr Trp Gln Thr Asp Asp Ala
        290                 295                 300
Ile Ser Ala Ser Ser Trp Ser Tyr Thr Val Gly Ile Lys Tyr Tyr Ser
305                 310                 315                 320
Ser Lys Ala Met Val His Ser Leu Leu Asp Arg Val Ser Lys Asn Gly
                325                 330                 335
Asn Met Leu Leu Asn Ile Ser Pro Met Ala Asn Gly Val Leu Pro Glu
            340                 345                 350
Glu Gln Ile Lys Val Leu Asn Asp Ile Gly Asp Phe Leu Ser Arg Tyr
        355                 360                 365
Gly Glu Ala Val Tyr Asp Thr Arg Ala Trp Asp Ile Tyr Gly Glu Gly
        370                 375                 380
Pro Asn Gln Val Glu Gly Gly Ser Phe Thr Ala Pro Leu Gln Gly Asn
385                 390                 395                 400
Ser Ser Asp Ile Arg Phe Thr Arg Asn Lys Glu Asp Val Leu Tyr
                405                 410                 415
Val Thr Val Leu Gly Trp Pro Glu Asp Asn Leu Val Ser Val Lys Asn
            420                 425                 430
Leu Gly Ser Asn Ala Leu Val Asp Leu Glu Ser Leu Lys Ser Val Glu
        435                 440                 445
Leu Leu Gly Asp Lys Ala Gly Asp Tyr Val Lys Val Ser Glu Trp Glu
        450                 455                 460
Gln Ser Lys Asp Ala Leu Asp Ile Thr Leu Pro Ser Gln Pro Ala Glu
465                 470                 475                 480
Ser Leu Ala Tyr Val Leu Lys Leu Thr Phe Asp Gly Gly Ile Pro Val
                485                 490                 495
Pro Gln Pro Glu Arg Gly Ala Ala Val Phe Ser Lys Ala Asp Ala Thr
            500                 505                 510
Gly Lys Gly Val Ala Leu Ala Leu Gly Thr Phe Asp Thr Val Phe Leu
        515                 520                 525
Thr Glu Ala Gly Leu Lys Pro Glu Glu Ile Arg Ser Ile Arg Val Ser
        530                 535                 540
Asp Gly Thr Lys Ala Thr Leu Phe Ser Gly Phe Arg Phe Thr Gly Glu
545                 550                 555                 560
Ser Lys Glu Leu Ser Ala Gly Glu His Glu Val Glu Asp Gly Ser Val
                565                 570                 575
Gly Ser Ile Val Val Ser Lys Ile
            580

<210> SEQ ID NO 22
<211> LENGTH: 3900
<212> TYPE: DNA
<213> ORGANISM: Alicyclobacillus acidocaldarius

<400> SEQUENCE: 22
gtgaagtgga cgggtgccgc gagccttgcg acgaccatcg tcatgtctgc agcgcttccg      60
ttcgcggcgt ttgaaaacac ccgttccgtc ggcacggaac gcgttctggc ggcgaccgcg     120
gcggatagta ctaacgcctc gccccccgacc ggggcgtccg caggcggtgg cacagcagga     180

```
gagacctact cgaatgccgt gcagattgtg agcggcaatg gctttcgcgc tggaaacggg    240
gccacggtcg tcctcgctgt gaatggactg aacttgaacc cctcgagttt caaggttgtg    300
gtatcgaata gcctcaacgg cgtgatcgac gtcacaagtg attccgtgct aacggggccg    360
aattcgattg ccttgcacct tcctgccggg gatgacgggc ttggcgccgg tacgtacacg    420
gtcaccgtcg aaagtggagg tgattcggtc tcgacgcctt caggacaggg acttcaggtc    480
atgccttata cgacggccga caccattcag tgggatggaa tctacacatc cgatggcgcg    540
atgtacgtgt cagatccgaa tccctcccct ggacaagagg tgacgatcag ccttcgagcg    600
tacagcggga acctgacgaa ggtgatcctg aattgctggg acaccgcaca aacaagggt     660 ttccaggtcg agatgtctcc aggcagaacg tttggaccgt atcagctctg gtctgccacg    720
atccccgctt caaacggcgg aacgatctat tatcgctttg acatatacga tggcaccagt    780
tttgcgtgtc tctcaggtga cggactgcac acgtctgacg acatcaacaa caatttcccg    840
ttgcccgtgg ggacggtcac gcttttcgaca cttcaggcga atcccggtga tacggtgacg    900
gtctccgacc ctgtaggtga cttcgccgga agccaggatc aacccaatca cacggtgata    960
cggtttgtca actcgtcggg cgaaacgggc gccacagtca atgggacgaa cgcgagctgg   1020
aacagcgtgc agttcacagt cccacagagc cttccaaacg gcttgtatcg cgtcgagatc   1080
gacacggtcg ccaaggacgc ggatggggtg tcaatgtcg aattggacag gagtgcggag    1140
cttattgtag ggcctctgcc cgcgtggatg caagcgtatg cacatgattc gtttcaggcg   1200
ttctaccgat cgcctttcgg agccgtgtcc acaggaaccc ccatcacgct tcgcctgcgg   1260
gctccgctca gcgtgaagag tgcgacgctt cgcctctggg gggcagcgga tcagtcaggc   1320
gagatcgacc tgccgatgca gaagctccaa atgtcgggag acgagttggc gcaacaaacc   1380
ggcgtgcagg acatcaacga ctacacgtgg tggacggtga ccatccctgc ggcggatgtg   1440
accacacccg ggacgatgtg gtatcagttc gtgacggaga cggacactgg ccaggtggtc   1500
tactacgatg acaatggagc tcagcttgaa gggcctggcc aggttgggtt gtcttccgac   1560
ggaccgagct accagatcag cgtatacgaa cggggatttc agacgccaga ttggctgaag   1620
cacgccgtga tctacgaaat catgccggat cggttctaca atggcaatat cgccacggag   1680
gagaatccga atacgcaaaa ggggatttat gtaggggccg atggaacgga gtcattaggc   1740
cccatccagt tccacgagaa ctgggactcg ccgccctatg atccgaatat tcctccgtta   1800
tctgatccca aaattgccag tctgcgaggc aatggccaat ggaacattga cttttcgga    1860 ggtgatttgc agggcatcga ggataagctg gactacctga agagccttgg agtcaatacg   1920
ctgtatctga tgcccgtctt tgaggcggaa tccaatcaca aatatgacac agccgactat   1980
ttcaagattg accctggatt tggaacgcag caggactggc tgaatctcgt acaggctgcg   2040
cacgcgaagg ggttccatat cattctcgac ggggtgttcg aagataccgg aagtgacagc   2100
gtatatttca acaagttcgg gaacttccac tccaacggtg cgtggcaggc gtacctgaag   2160
aaccagccgt cgctgtcgcc ctactactcg tggtacgtgt ggacagggaa cacctcaaac   2220
ccatacgatt cgtggtttca gatcgacacg ctgccactta cggacacgtc gaaccccgcc   2280
tatcagcgat tcgtgtatgg gagcgacaac tcagtcgcgc gtgtgtggat ccgggaaggt   2340
gcggacggat ggcgcttgga ctcggccgac aacgggaatt tcaacacggc atggtgggt    2400 ggctttcggc aggccgtgaa atcgatcgat cccaacgcag cgatcatcgg cgagatctgg   2460
gacaatgcga cgaatgacaa tggaacggat tggttgacgg gatcgacctt cgacagtgta   2520
atgaactacc agttccggaa cgccgtgatc gacttcttcc gcggcacgta caacgacgga   2580
```

```
aacgtgcagc accacgccgt cgacgctgcg ggattcaacc aggaactgat gcgcctgtac   2640
agtgaatatc ctctgcagtc gttctactcg atgatgaacc ttgtcgattc gcaagacacc   2700
atgcggatcc tgaccatctt ggagaacgcg ccgcagccag gcgatctatc cgcgctccag   2760
caggatgagt acaggccgtc tcctgcggct gaacagttgg ggatcgagag gctgaagctt   2820
gtatcggact ttcaattcag cttcccgggc gatccgacca tcttctacgg cgacgaggca   2880
gggctcactg gttattcgga tcccctcaat cgtcggacct atccgtggga caaccagaat   2940
ctcgatctcc tgaaccacta ccgcaagctc ggggccattc gaaacgccaa tcctgtgctt   3000
cagacggggg atttcacgcc gttgtacgca cagggcatgg tgtacgcatt tgcaaggacc   3060
attcggaatg ggcgagatgt cttcggtgtg ccagcggagg atgccacggc cattgtggcg   3120
atcaacaatc agaaccaagc tatcaccgtg accattccga cggatgggac ggttgcggac   3180
gggtccacga tgctcgatga actgaacaac cagtggtaca aggtgcagaa tggtggcatt   3240
acactcacgc tgcaatcgta tcaaggtgcc attttggtga cgccgagcga cgcgccgatg   3300
gcttatctgc aagaggagga ttctcagaac gagattgcgt ggacgcctgt gcaaggtgcc   3360
atcggttatc gcgtctggag acagaatccg aatggacaat gggtgccctt tggacctgtg   3420
cttcctgcca cggacttgag tgtcacggtg gaacgcgatg catatgcgca aacgtttgct   3480
gtacaagcgc tgttttcggc gtctgatcac gcccagtctc cggtgtcggc acctaagacg   3540
gtatcgcttc ccgtcgatgt gcccgcggta cgcctgagtc agccgatcgt tagtggtcgt   3600
gtggttggag atcgtgcgat ggtctcgatc acgccggttt caggcgcgac gcagtatgtg   3660
atctaccaga gacagggcga cggatcgtat gctccggtcg cgacggtctc cacaagtggc   3720
gattccgcag ctataggga agttcctgcg caaggtccgg ccaactcgcc tcacgcgacg   3780
attcgcgtga cagtgcccgt acctgcaggt ttctcgtcgg tgacctaccg cgtggctgcg   3840
caaaacgaag atgggcaagc tgtgaccaat ccattgaccc tatcgctctc gaaaagtga    3900
```

<210> SEQ ID NO 23
<211> LENGTH: 1299
<212> TYPE: PRT
<213> ORGANISM: Alicyclobacillus acidocaldarius

<400> SEQUENCE: 23

Met Lys Trp Thr Gly Ala Ala Ser Leu Ala Thr Thr Ile Val Met Ser
1               5                   10                  15

Ala Ala Leu Pro Phe Ala Ala Phe Glu Asn Thr Arg Ser Val Gly Thr
            20                  25                  30

Glu Arg Val Leu Ala Ala Thr Ala Ala Asp Ser Thr Asn Ala Ser Pro
        35                  40                  45

Pro Thr Gly Ala Ser Ala Gly Gly Gly Thr Ala Gly Glu Thr Tyr Ser
    50                  55                  60

Asn Ala Val Gln Ile Val Ser Gly Asn Gly Phe Arg Ala Gly Asn Gly
65                  70                  75                  80

Ala Thr Val Val Leu Ala Val Asn Gly Leu Asn Leu Asn Pro Ser Ser
                85                  90                  95

Phe Lys Val Val Ser Asn Ser Leu Asn Gly Val Ile Asp Val Thr
            100                 105                 110

Ser Asp Ser Val Leu Thr Gly Pro Asn Ser Ile Ala Leu His Leu Pro
        115                 120                 125

Ala Gly Asp Asp Gly Leu Gly Ala Gly Thr Tyr Thr Val Thr Val Glu
    130                 135                 140

Ser Gly Gly Asp Ser Val Ser Thr Pro Ser Gly Gln Gly Leu Gln Val
145                 150                 155                 160

Met Pro Tyr Thr Thr Ala Asp Thr Ile Gln Trp Asp Gly Ile Tyr Thr
                165                 170                 175

Ser Asp Gly Ala Met Tyr Val Ser Asp Pro Asn Pro Ser Pro Gly Gln
            180                 185                 190

Glu Val Thr Ile Ser Leu Arg Ala Tyr Ser Gly Asn Leu Thr Lys Val
        195                 200                 205

Ile Leu Asn Cys Trp Asp Thr Ala Gln Asn Lys Gly Phe Gln Val Glu
    210                 215                 220

Met Ser Pro Gly Arg Thr Phe Gly Pro Tyr Gln Leu Trp Ser Ala Thr
225                 230                 235                 240

Ile Pro Ala Ser Asn Gly Gly Thr Ile Tyr Tyr Arg Phe Asp Ile Tyr
                245                 250                 255

Asp Gly Thr Ser Phe Ala Cys Leu Ser Gly Asp Gly Leu His Thr Ser
            260                 265                 270

Asp Asp Ile Asn Asn Asn Phe Pro Leu Pro Val Gly Thr Val Thr Leu
        275                 280                 285

Ser Thr Leu Gln Ala Asn Pro Gly Asp Thr Val Thr Val Ser Asp Pro
    290                 295                 300

Val Gly Asp Phe Ala Gly Ser Gln Asp Gln Pro Asn His Thr Val Ile
305                 310                 315                 320

Arg Phe Val Asn Ser Ser Gly Glu Thr Ala Ala Thr Val Asn Gly Thr
                325                 330                 335

Asn Ala Ser Trp Asn Ser Val Gln Phe Thr Val Pro Gln Ser Leu Pro
            340                 345                 350

Asn Gly Leu Tyr Arg Val Glu Ile Asp Thr Val Ala Lys Asp Ala Asp
        355                 360                 365

Gly Val Val Asn Val Glu Leu Asp Arg Ser Ala Glu Leu Ile Val Gly
    370                 375                 380

Pro Leu Pro Ala Trp Met Gln Ala Tyr Ala His Asp Ser Phe Gln Ala
385                 390                 395                 400

Phe Tyr Arg Ser Pro Phe Gly Ala Val Ser Thr Gly Thr Pro Ile Thr
                405                 410                 415

Leu Arg Leu Arg Ala Pro Leu Ser Val Lys Ser Ala Thr Leu Arg Leu
            420                 425                 430

Trp Gly Ala Ala Asp Gln Ser Gly Glu Ile Asp Leu Pro Met Gln Lys
        435                 440                 445

Leu Gln Met Ser Gly Asp Glu Leu Ala Gln Gln Thr Gly Val Gln Asp
    450                 455                 460

Ile Asn Asp Tyr Thr Trp Trp Thr Val Thr Ile Pro Ala Ala Asp Val
465                 470                 475                 480

Thr Thr Pro Gly Thr Met Trp Tyr Gln Phe Val Thr Glu Thr Asp Thr
                485                 490                 495

Gly Gln Val Val Tyr Tyr Asp Asp Asn Gly Ala Gln Leu Glu Gly Pro
            500                 505                 510

Gly Gln Val Gly Leu Ser Ser Asp Gly Pro Ser Tyr Gln Ile Ser Val
        515                 520                 525

Tyr Glu Arg Gly Phe Gln Thr Pro Asp Trp Leu Lys His Ala Val Ile
    530                 535                 540

Tyr Glu Ile Met Pro Asp Arg Phe Tyr Asn Gly Asn Ile Ala Thr Glu
545                 550                 555                 560

```
Glu Asn Pro Asn Thr Gln Lys Gly Ile Tyr Val Gly Ala Asp Gly Thr
            565                 570                 575
Glu Ser Leu Gly Pro Ile Gln Phe His Glu Asn Trp Asp Ser Pro Pro
        580                 585                 590
Tyr Asp Pro Asn Ile Pro Pro Leu Ser Asp Pro Lys Ile Ala Ser Leu
    595                 600                 605
Arg Gly Asn Gly Gln Trp Asn Ile Asp Phe Phe Gly Gly Asp Leu Gln
610                 615                 620
Gly Ile Glu Asp Lys Leu Asp Tyr Leu Lys Ser Leu Gly Val Asn Thr
625                 630                 635                 640
Leu Tyr Leu Met Pro Val Phe Glu Ala Glu Ser Asn His Lys Tyr Asp
            645                 650                 655
Thr Ala Asp Tyr Phe Lys Ile Asp Pro Gly Phe Gly Thr Gln Gln Asp
        660                 665                 670
Trp Leu Asn Leu Val Gln Ala Ala His Ala Lys Gly Phe His Ile Ile
    675                 680                 685
Leu Asp Gly Val Phe Glu Asp Thr Gly Ser Asp Ser Val Tyr Phe Asn
690                 695                 700
Lys Phe Gly Asn Phe His Ser Asn Gly Ala Trp Gln Ala Tyr Leu Lys
705                 710                 715                 720
Asn Gln Pro Ser Leu Ser Pro Tyr Tyr Ser Trp Tyr Val Trp Thr Gly
            725                 730                 735
Asn Thr Ser Asn Pro Tyr Asp Ser Trp Phe Gln Ile Asp Thr Leu Pro
        740                 745                 750
Leu Thr Asp Thr Ser Asn Pro Ala Tyr Gln Arg Phe Val Tyr Gly Ser
    755                 760                 765
Asp Asn Ser Val Ala Arg Val Trp Ile Arg Glu Gly Ala Asp Gly Trp
770                 775                 780
Arg Leu Asp Ser Ala Asp Asn Gly Asn Phe Asn Thr Ala Trp Trp Gly
785                 790                 795                 800
Gly Phe Arg Gln Ala Val Lys Ser Ile Asp Pro Asn Ala Ala Ile Ile
            805                 810                 815
Gly Glu Ile Trp Asp Asn Ala Thr Asn Asp Asn Gly Thr Asp Trp Leu
        820                 825                 830
Thr Gly Ser Thr Phe Asp Ser Val Met Asn Tyr Gln Phe Arg Asn Ala
    835                 840                 845
Val Ile Asp Phe Phe Arg Gly Thr Tyr Asn Asp Gly Asn Val Gln His
850                 855                 860
His Ala Val Asp Ala Ala Gly Phe Asn Gln Glu Leu Met Arg Leu Tyr
865                 870                 875                 880
Ser Glu Tyr Pro Leu Gln Ser Phe Tyr Ser Met Met Asn Leu Val Asp
            885                 890                 895
Ser Gln Asp Thr Met Arg Ile Leu Thr Ile Leu Glu Asn Ala Pro Gln
        900                 905                 910
Pro Gly Asp Leu Ser Ala Leu Gln Gln Asp Glu Tyr Arg Pro Ser Pro
    915                 920                 925
Ala Ala Glu Gln Leu Gly Ile Glu Arg Leu Lys Leu Val Ser Asp Phe
930                 935                 940
Gln Phe Ser Phe Pro Gly Asp Pro Thr Ile Phe Tyr Gly Asp Glu Ala
945                 950                 955                 960
Gly Leu Thr Gly Tyr Ser Asp Pro Leu Asn Arg Arg Thr Tyr Pro Trp
            965                 970                 975
Asp Asn Gln Asn Leu Asp Leu Leu Asn His Tyr Arg Lys Leu Gly Ala
```

Ile Arg Asn Ala Asn Pro Val Leu Gln Thr Gly Asp Phe Thr Pro Leu
    980                 985                 990

Tyr Ala Gln Gly Met Val Tyr Ala Phe Ala Arg Thr Ile Arg Asn
    995                 1000                1005

Gly Arg Asp Val Phe Gly Val Pro Ala Glu Asp Ala Thr Ala Ile
    1010                1015                1020

Val Ala Ile Asn Asn Gln Asn Gln Ala Ile Thr Val Thr Ile Pro
    1025                1030                1035

Thr Asp Gly Thr Val Ala Asp Gly Ser Thr Met Leu Asp Glu Leu
    1040                1045                1050

Asn Asn Gln Trp Tyr Lys Val Gln Asn Gly Gly Ile Thr Leu Thr
    1055                1060                1065

Leu Gln Ser Tyr Gln Gly Ala Ile Leu Val Thr Pro Ser Asp Ala
    1070                1075                1080

Pro Met Ala Tyr Leu Gln Glu Glu Asp Ser Gln Asn Glu Ile Ala
    1085                1090                1095

Trp Thr Pro Val Gln Gly Ala Ile Gly Tyr Arg Val Trp Arg Gln
    1100                1105                1110

Asn Pro Asn Gly Gln Trp Val Pro Phe Gly Pro Val Leu Pro Ala
    1115                1120                1125

Thr Asp Leu Ser Val Thr Val Glu Arg Asp Ala Tyr Ala Gln Thr
    1130                1135                1140

Phe Ala Val Gln Ala Leu Phe Ser Ala Ser Asp His Ala Gln Ser
    1145                1150                1155

Pro Val Ser Ala Pro Lys Thr Val Ser Leu Pro Val Asp Val Pro
    1160                1165                1170

Ala Val Arg Leu Ser Gln Pro Ile Val Ser Gly Arg Val Val Gly
    1175                1180                1185

Asp Arg Ala Met Val Ser Ile Thr Pro Val Ser Gly Ala Thr Gln
    1190                1195                1200

Tyr Val Ile Tyr Gln Arg Gln Gly Asp Gly Ser Tyr Ala Pro Val
    1205                1210                1215

Ala Thr Val Ser Thr Ser Gly Asp Ser Ala Ala Ile Gly Glu Val
    1220                1225                1230

Pro Ala Gln Gly Pro Ala Asn Ser Pro His Ala Thr Ile Arg Val
    1235                1240                1245

Thr Val Pro Val Pro Ala Gly Phe Ser Ser Val Thr Tyr Arg Val
    1250                1255                1260

Ala Ala Gln Asn Glu Asp Gly Gln Ala Val Thr Asn Pro Leu Thr
    1265                1270                1275

Leu Ser Leu Ser Lys Lys
    1280

<210> SEQ ID NO 24
<211> LENGTH: 1276
<212> TYPE: PRT
<213> ORGANISM: Alicyclobacillus acidocaldarius

<400> SEQUENCE: 24

Phe Glu Asn Thr Arg Ser Val Gly Thr Glu Arg Val Leu Ala Ala Thr
1               5                   10                  15

Ala Ala Asp Ser Thr Asn Ala Pro Pro Thr Gly Ala Ser Ala Gly
            20                  25                  30

Gly Gly Thr Ala Gly Glu Thr Tyr Ser Asn Ala Val Gln Ile Val Ser
             35                  40                  45

Gly Asn Gly Phe Arg Ala Gly Asn Gly Ala Thr Val Val Leu Ala Val
 50                  55                  60

Asn Gly Leu Asn Leu Asn Pro Ser Ser Phe Lys Val Val Ser Asn
 65                  70                  75                  80

Ser Leu Asn Gly Val Ile Asp Val Thr Ser Asp Ser Val Leu Thr Gly
                 85                  90                  95

Pro Asn Ser Ile Ala Leu His Leu Pro Ala Gly Asp Asp Gly Leu Gly
                100                 105                 110

Ala Gly Thr Tyr Thr Val Thr Val Glu Ser Gly Gly Asp Ser Val Ser
             115                 120                 125

Thr Pro Ser Gly Gln Gly Leu Gln Val Met Pro Tyr Thr Thr Ala Asp
             130                 135                 140

Thr Ile Gln Trp Asp Gly Ile Tyr Thr Ser Asp Gly Ala Met Tyr Val
145                 150                 155                 160

Ser Asp Pro Asn Pro Ser Pro Gly Gln Glu Val Thr Ile Ser Leu Arg
                165                 170                 175

Ala Tyr Ser Gly Asn Leu Thr Lys Val Ile Leu Asn Cys Trp Asp Thr
             180                 185                 190

Ala Gln Asn Lys Gly Phe Gln Val Glu Met Ser Pro Gly Arg Thr Phe
             195                 200                 205

Gly Pro Tyr Gln Leu Trp Ser Ala Thr Ile Pro Ala Ser Asn Gly Gly
             210                 215                 220

Thr Ile Tyr Tyr Arg Phe Asp Ile Tyr Asp Gly Thr Ser Phe Ala Cys
225                 230                 235                 240

Leu Ser Gly Asp Gly Leu His Thr Ser Asp Ile Asn Asn Asn Phe
                245                 250                 255

Pro Leu Pro Val Gly Thr Val Thr Leu Ser Thr Leu Gln Ala Asn Pro
                260                 265                 270

Gly Asp Thr Val Thr Val Ser Asp Pro Val Gly Asp Phe Ala Gly Ser
             275                 280                 285

Gln Asp Gln Pro Asn His Thr Val Ile Arg Phe Val Asn Ser Ser Gly
             290                 295                 300

Glu Thr Ala Ala Thr Val Asn Gly Thr Asn Ala Ser Trp Asn Ser Val
305                 310                 315                 320

Gln Phe Thr Val Pro Gln Ser Leu Pro Asn Gly Leu Tyr Arg Val Glu
                325                 330                 335

Ile Asp Thr Val Ala Lys Asp Ala Asp Gly Val Val Asn Val Glu Leu
             340                 345                 350

Asp Arg Ser Ala Glu Leu Ile Val Gly Pro Leu Pro Ala Trp Met Gln
             355                 360                 365

Ala Tyr Ala His Asp Ser Phe Gln Ala Phe Tyr Arg Ser Pro Phe Gly
             370                 375                 380

Ala Val Ser Thr Gly Thr Pro Ile Thr Leu Arg Leu Arg Ala Pro Leu
385                 390                 395                 400

Ser Val Lys Ser Ala Thr Leu Arg Leu Trp Gly Ala Ala Asp Gln Ser
                405                 410                 415

Gly Glu Ile Asp Leu Pro Met Gln Lys Leu Gln Met Ser Gly Asp Glu
             420                 425                 430

Leu Ala Gln Gln Thr Gly Val Gln Asp Ile Asn Asp Tyr Thr Trp Trp
             435                 440                 445

Thr Val Thr Ile Pro Ala Ala Asp Val Thr Thr Pro Gly Thr Met Trp

```
              450                 455                 460
Tyr Gln Phe Val Thr Glu Thr Asp Thr Gly Gln Val Val Tyr Tyr Asp
465                 470                 475                 480

Asp Asn Gly Ala Gln Leu Glu Gly Pro Gly Gln Val Gly Leu Ser Ser
                485                 490                 495

Asp Gly Pro Ser Tyr Gln Ile Ser Val Tyr Glu Arg Gly Phe Gln Thr
                500                 505                 510

Pro Asp Trp Leu Lys His Ala Val Ile Tyr Glu Ile Met Pro Asp Arg
                515                 520                 525

Phe Tyr Asn Gly Asn Ile Ala Thr Glu Glu Asn Pro Asn Thr Gln Lys
                530                 535                 540

Gly Ile Tyr Val Gly Ala Asp Gly Thr Glu Ser Leu Gly Pro Ile Gln
545                 550                 555                 560

Phe His Glu Asn Trp Asp Ser Pro Tyr Asp Pro Asn Ile Pro Pro
                565                 570                 575

Leu Ser Asp Pro Lys Ile Ala Ser Leu Arg Gly Asn Gly Gln Trp Asn
                580                 585                 590

Ile Asp Phe Phe Gly Gly Asp Leu Gln Gly Ile Glu Asp Lys Leu Asp
                595                 600                 605

Tyr Leu Lys Ser Leu Gly Val Asn Thr Leu Tyr Leu Met Pro Val Phe
                610                 615                 620

Glu Ala Glu Ser Asn His Lys Tyr Asp Thr Ala Asp Tyr Phe Lys Ile
625                 630                 635                 640

Asp Pro Gly Phe Gly Thr Gln Gln Asp Trp Leu Asn Leu Val Gln Ala
                645                 650                 655

Ala His Ala Lys Gly Phe His Ile Ile Leu Asp Gly Val Phe Glu Asp
                660                 665                 670

Thr Gly Ser Asp Ser Val Tyr Phe Asn Lys Phe Gly Asn Phe His Ser
                675                 680                 685

Asn Gly Ala Trp Gln Ala Tyr Leu Lys Asn Gln Pro Ser Leu Ser Pro
                690                 695                 700

Tyr Tyr Ser Trp Tyr Val Trp Thr Gly Asn Thr Ser Asn Pro Tyr Asp
705                 710                 715                 720

Ser Trp Phe Gln Ile Asp Thr Leu Pro Leu Thr Asp Thr Ser Asn Pro
                725                 730                 735

Ala Tyr Gln Arg Phe Val Tyr Gly Ser Asp Asn Ser Val Ala Arg Val
                740                 745                 750

Trp Ile Arg Glu Gly Ala Asp Gly Trp Arg Leu Asp Ser Ala Asp Asn
                755                 760                 765

Gly Asn Phe Asn Thr Ala Trp Trp Gly Gly Phe Arg Gln Ala Val Lys
                770                 775                 780

Ser Ile Asp Pro Asn Ala Ala Ile Ile Gly Glu Ile Trp Asp Asn Ala
785                 790                 795                 800

Thr Asn Asp Asn Gly Thr Asp Trp Leu Thr Gly Ser Thr Phe Asp Ser
                805                 810                 815

Val Met Asn Tyr Gln Phe Arg Asn Ala Val Ile Asp Phe Phe Arg Gly
                820                 825                 830

Thr Tyr Asn Asp Gly Asn Val Gln His His Ala Val Asp Ala Ala Gly
                835                 840                 845

Phe Asn Gln Glu Leu Met Arg Leu Tyr Ser Glu Tyr Pro Leu Gln Ser
                850                 855                 860

Phe Tyr Ser Met Met Asn Leu Val Asp Ser Gln Asp Thr Met Arg Ile
865                 870                 875                 880
```

-continued

Leu Thr Ile Leu Glu Asn Ala Pro Gln Pro Gly Asp Leu Ser Ala Leu
            885                 890                 895

Gln Gln Asp Glu Tyr Arg Pro Ser Pro Ala Ala Glu Gln Leu Gly Ile
    900                 905                 910

Glu Arg Leu Lys Leu Val Ser Asp Phe Gln Phe Ser Phe Pro Gly Asp
        915                 920                 925

Pro Thr Ile Phe Tyr Gly Asp Glu Ala Gly Leu Thr Gly Tyr Ser Asp
    930                 935                 940

Pro Leu Asn Arg Arg Thr Tyr Pro Trp Asp Asn Gln Asn Leu Asp Leu
945                 950                 955                 960

Leu Asn His Tyr Arg Lys Leu Gly Ala Ile Arg Asn Ala Asn Pro Val
            965                 970                 975

Leu Gln Thr Gly Asp Phe Thr Pro Leu Tyr Ala Gln Gly Met Val Tyr
            980                 985                 990

Ala Phe Ala Arg Thr Ile Arg Asn Gly Arg Asp Val Phe Gly Val Pro
            995                 1000                1005

Ala Glu Asp Ala Thr Ala Ile Val Ala Ile Asn Asn Gln Asn Gln
    1010                1015                1020

Ala Ile Thr Val Thr Ile Pro Thr Asp Gly Thr Val Ala Asp Gly
    1025                1030                1035

Ser Thr Met Leu Asp Glu Leu Asn Asn Gln Trp Tyr Lys Val Gln
    1040                1045                1050

Asn Gly Gly Ile Thr Leu Thr Leu Gln Ser Tyr Gln Gly Ala Ile
    1055                1060                1065

Leu Val Thr Pro Ser Asp Ala Pro Met Ala Tyr Leu Gln Glu Glu
    1070                1075                1080

Asp Ser Gln Asn Glu Ile Ala Trp Thr Pro Val Gln Gly Ala Ile
    1085                1090                1095

Gly Tyr Arg Val Trp Arg Gln Asn Pro Asn Gly Gln Trp Val Pro
    1100                1105                1110

Phe Gly Pro Val Leu Pro Ala Thr Asp Leu Ser Val Thr Val Glu
    1115                1120                1125

Arg Asp Ala Tyr Ala Gln Thr Phe Ala Val Gln Ala Leu Phe Ser
    1130                1135                1140

Ala Ser Asp His Ala Gln Ser Pro Val Ser Ala Pro Lys Thr Val
    1145                1150                1155

Ser Leu Pro Val Asp Val Pro Ala Val Arg Leu Ser Gln Pro Ile
    1160                1165                1170

Val Ser Gly Arg Val Val Gly Asp Arg Ala Met Val Ser Ile Thr
    1175                1180                1185

Pro Val Ser Gly Ala Thr Gln Tyr Val Ile Tyr Gln Arg Gln Gly
    1190                1195                1200

Asp Gly Ser Tyr Ala Pro Val Ala Thr Val Ser Thr Ser Gly Asp
    1205                1210                1215

Ser Ala Ala Ile Gly Glu Val Pro Ala Gln Gly Pro Ala Asn Ser
    1220                1225                1230

Pro His Ala Thr Ile Arg Val Thr Val Pro Val Pro Ala Gly Phe
    1235                1240                1245

Ser Ser Val Thr Tyr Arg Val Ala Ala Gln Asn Glu Asp Gly Gln
    1250                1255                1260

Ala Val Thr Asn Pro Leu Thr Leu Ser Leu Ser Lys Lys
    1265                1270                1275

ENZYMES FOR INHIBITING GROWTH OF BIOFILMS AND DEGRADING SAME

CROSS-REFERENCE TO RELATED APPLICATIONS

This application claims priority under 35 USC §119(e) to U.S. Provisional Patent Application 61/725,257 filed Nov. 12, 2012, the entirety of which is incorporated herein by reference.

FIELD OF THE INVENTION

The present invention is directed to inhibiting growth of biofilms and degrading biofilms, such as biofilms caused by infection with *Pseudomonas aeruginosa* and/or other microorganisms. The present invention is also directed treating infections with microorganisms associated with biofilms.

BACKGROUND

A biofilm is a group of microorganisms in which cells stick to each other on a surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces and can be prevalent in natural, industrial, and hospital settings (Hall-Stoodley et al., Lear). The microbial cells growing in a biofilm are physiologically distinct from planktonic cells of the same organism, which, by contrast, are single-cells that may float or swim in a liquid medium.

Nearly every species of microorganism, not only bacteria, fungi, and archaea, have mechanisms by which they can form biofilms by adhering to surfaces and to each other. Biofilms can form on virtually any non-shedding surface in a non-sterile aqueous or humid environment.

Biofilms have been found to be involved in a wide variety of microbial infections in the body, by one estimate 80% of all infections (NIH). Infectious processes in which biofilms have been implicated include urinary tract infections, sinusitis, catheter infections, middle-ear infections, formation of dental plaque (Rogers), gingivitis (Rogers), infections on contact lenses (Imamura et al.), endocarditis, infections in cystic fibrosis, skin infections (Davis et al.), and infections of implanted devices or permanent indwelling devices such as joint prostheses, prosthetic heart valves, catheters, and intrauterine devices (Lewis, Parsek et al., Auler et al., Donlan et al.).

Biofilms confer microorganisms resistance to antimicrobial agents, whether these antimicrobial agents are antibiotics, disinfectants, or germicides (Donlan et al.). Mechanisms responsible for this resistance is thought to include one or more of the following: (i) delayed penetration of the antimicrobial agent through the biofilm matrix, (ii) altered growth rate of biofilm organisms, and (iii) other physiological changes due to the biofilm mode of growth (Donlan et al.).

Enzymes that degrade biofilm matrix polymers have been shown to inhibit biofilm formation, detach established biofilm colonies, and render biofilm microorganisms sensitive to antimicrobial agents (Kaplan).

Enzymes that have enhanced activity in preventing biofilm formation or degrading existing biofilms are needed.

SUMMARY OF THE INVENTION

The invention is directed to enzymes for inhibiting growth of biofilms and for degrading pre-formed biofilms. The enzymes comprise glycosyl hydrolases. The enzymes may be formulated in compositions with and without antimicrobial agents. The enzymes with and without the antimicrobial agents may be delivered to biofilms to degrade the biofilms and treat infections of microorganisms associated with the biofilms, delivered to surfaces to inhibit growth of biofilms thereon, and administered to animals to inhibit growth of biofilms therein. The combination of the enzymes and the antimicrobial agents provides a synergistic effect in inhibiting growth of biofilms and/or degrading biofilms.

One version of the invention comprises a composition for degrading biofilm. The composition comprises biofilm-degrading amounts of at least one enzyme and at least one antimicrobial agent. The at least one enzyme comprises an amino acid sequence selected from the group consisting of a sequence at least 80% identical to SEQ ID NO:3, a sequence at least 80% identical to SEQ ID NO:6, a sequence at least 80% identical to SEQ ID NO:9, a sequence at least 80% identical to SEQ ID NO:12, a sequence at least 80% identical to SEQ ID NO:15, a sequence at least 80% identical to SEQ ID NO: 18, a sequence at least 80% identical to SEQ ID NO:21, and a sequence at least 80% identical to SEQ ID NO:24. In some versions, the at least one enzyme comprises an amino acid sequence selected from the group consisting of a sequence at least 90% identical to SEQ ID NO:3, a sequence at least 90% identical to SEQ ID NO:6, a sequence at least 90% identical to SEQ ID NO:9, a sequence at least 90% identical to SEQ ID NO:12, a sequence at least 90% identical to SEQ ID NO:15, a sequence at least 90% identical to SEQ ID NO: 18, a sequence at least 80% identical to SEQ ID NO:21, and a sequence at least 90% identical to SEQ ID NO:24. In some versions, the at least one enzyme comprises an amino acid sequence selected from the group consisting of a sequence at least 95% identical to SEQ ID NO:3, a sequence at least 95% identical to SEQ ID NO:6, a sequence at least 95% identical to SEQ ID NO:9, a sequence at least 95% identical to SEQ ID NO:12, a sequence at least 95% identical to SEQ ID NO:15, a sequence at least 95% identical to SEQ ID NO: 18, a sequence at least 95% identical to SEQ ID NO:21, and a sequence at least 95% identical to SEQ ID NO:24, such as to SEQ ID NO:3, SEQ ID NO:6, SEQ ID NO:9, SEQ ID NO:12, SEQ ID NO:15, SEQ ID NO: 18, SEQ ID NO:21, and SEQ ID NO:24. The at least one enzyme may comprise one enzyme or any combination of enzymes described herein or known in the art. The at least one antimicrobial agent may comprise one antimicrobial agent or any combination of antimicrobial agents described herein or known in the art.

In some versions, the at least one antimicrobial agent comprises an aminoglycoside antibiotic, such as tobramycin.

In some versions, the at least one enzyme and the at least one antimicrobial agent are combined with a pharmaceutically acceptable carrier, preferably, for administration to an animal, such as a mammal or a human.

Another version of the invention comprises a method of degrading a biofilm. The method comprises contacting the biofilm with biofilm-degrading amounts of at least one enzyme and at least one antimicrobial agent. The at least one enzyme comprises an amino acid sequence selected from the group consisting of a sequence at least 80% identical to SEQ ID NO:3, a sequence at least 80% identical to SEQ ID NO:6, a sequence at least 80% identical to SEQ ID NO:9, a sequence at least 80% identical to SEQ ID NO:12, a sequence at least 80% identical to SEQ ID NO:15, a sequence at least 80% identical to SEQ ID NO: 18, a sequence at least 80% identical to SEQ ID NO:21, and a sequence at least 80% identical to SEQ ID NO:24. In some versions, the at least one enzyme comprises an amino acid sequence selected from the group consisting of a sequence at least 90% identical to SEQ ID NO:3, a sequence at least 90% identical to SEQ ID NO:6, a sequence at least 90% identical to SEQ ID NO:9, a sequence at least 90% identical to SEQ ID NO:12, a sequence at least 90% identical to SEQ ID NO:15, a sequence at least 90% identical to SEQ ID NO: 18, a sequence at least 80% identical to SEQ ID NO:21, and a sequence at least 90% identical to SEQ ID NO:24. In some versions, the at least one enzyme comprises an amino acid sequence selected from the group consisting of a sequence at least 95% identical to SEQ ID NO:3, a sequence at least 95% identical to SEQ ID NO:6, a sequence at least 95% identical to SEQ ID NO:9, a sequence at least 95% identical to SEQ ID NO:12, a sequence at least 95% identical to SEQ ID NO:15, a sequence at least 95% identical to SEQ ID NO: 18, a sequence at least 95% identical to SEQ ID NO:21, and a sequence at least 95% identical to SEQ ID NO:24, such as to SEQ ID NO:3, SEQ ID NO:6, SEQ ID NO:9, SEQ ID NO:12, SEQ ID NO:15, SEQ ID NO: 18, SEQ ID NO:21, and SEQ ID NO:24. The at least one enzyme may comprise one enzyme or any combination of enzymes described herein or known in the art. The at least one antimicrobial agent may comprise one antimicrobial agent or any combination of antimicrobial agents described herein or known in the art.

In some versions, the contacting comprises simultaneously delivering the at least one enzyme and the at least one antimicrobial agent to the biofilm.

In some versions, the contacting comprises non-simultaneously delivering the at least one enzyme and the at least one antimicrobial agent to the biofilm.

In some versions, the biofilm is an animal-associated biofilm hosted by an animal. The contacting may optionally comprise administering the at least one enzyme and the at least one antimicrobial agent to the animal. The administering may optionally comprise administering via inhalation. The animal may optimally be suffering from cystic fibrosis at the time of administration.

In some versions, the biofilm comprises a microorganism that, in a planktonic state, is sensitive to the at least one antimicrobial agent. The contacting kills or inhibits reproduction of the microorganism.

In some versions, the biofilm comprises *Pseudomonas aeruginosa*.

In some versions, the at least one antimicrobial agent comprises an aminoglycoside antibiotic, such as tobramycin.

Another version of the invention comprises a method of inhibiting formation of biofilm on a surface. The method comprises comprising contacting the surface with a biofilm-inhibiting amount of at least one enzyme. The at least one enzyme comprises an amino acid sequence selected from the group consisting of a sequence at least 80% identical to SEQ ID NO:3, a sequence at least 80% identical to SEQ ID NO:6, a sequence at least 80% identical to SEQ ID NO:9, a sequence at least 80% identical to SEQ ID NO:12, a sequence at least 80% identical to SEQ ID NO:15, a sequence at least 80% identical to SEQ ID NO: 18, a sequence at least 80% identical to SEQ ID NO:21, and a sequence at least 80% identical to SEQ ID NO:24. In some versions, the at least one enzyme comprises an amino acid sequence selected from the group consisting of a sequence at least 90% identical to SEQ ID NO:3, a sequence at least 90% identical to SEQ ID NO:6, a sequence at least 90% identical to SEQ ID NO:9, a sequence at least 90% identical to SEQ ID NO:12, a sequence at least 90% identical to SEQ ID NO:15, a sequence at least 90% identical to SEQ ID NO: 18, a sequence at least 80% identical to SEQ ID NO:21, and a sequence at least 90% identical to SEQ ID NO:24. In some versions, the at least one enzyme comprises an amino acid sequence selected from the group consisting of a sequence at least 95% identical to SEQ ID NO:3, a sequence at least 95% identical to SEQ ID NO:6, a sequence at least 95% identical to SEQ ID NO:9, a sequence at least 95% identical to SEQ ID NO:12, a sequence at least 95% identical to SEQ ID NO:15, a sequence at least 95% identical to SEQ ID NO: 18, a sequence at least 95% identical to SEQ ID NO:21, and a sequence at least 95% identical to SEQ ID NO:24, such as to SEQ ID NO:3, SEQ ID NO:6, SEQ ID NO:9, SEQ ID NO:12, SEQ ID NO:15, SEQ ID NO: 18, SEQ ID NO:21, and SEQ ID NO:24. The at least one enzyme may comprise one enzyme or any combination of enzymes described herein or known in the art. In some versions, the at least one enzyme is administered in combination with at least one antimicrobial agent. The at least one antimicrobial agent may comprise one antimicrobial agent or any combination of antimicrobial agents described herein or known in the art.

In some versions, the surface is a surface on or in an animal. The animal may be infected or suspected of being infected with a microorganism, such as a bacterium, optionally, *Pseudomonas aeruginosa*.

In some versions, the surface is a surface on an animal's lung and the contacting comprises administering the at least one enzyme via inhalation.

The objects and advantages of the invention will appear more fully from the following detailed description of the preferred embodiment of the invention made in conjunction with the accompanying drawings.

DETAILED DESCRIPTION OF THE INVENTION

Figure 1:
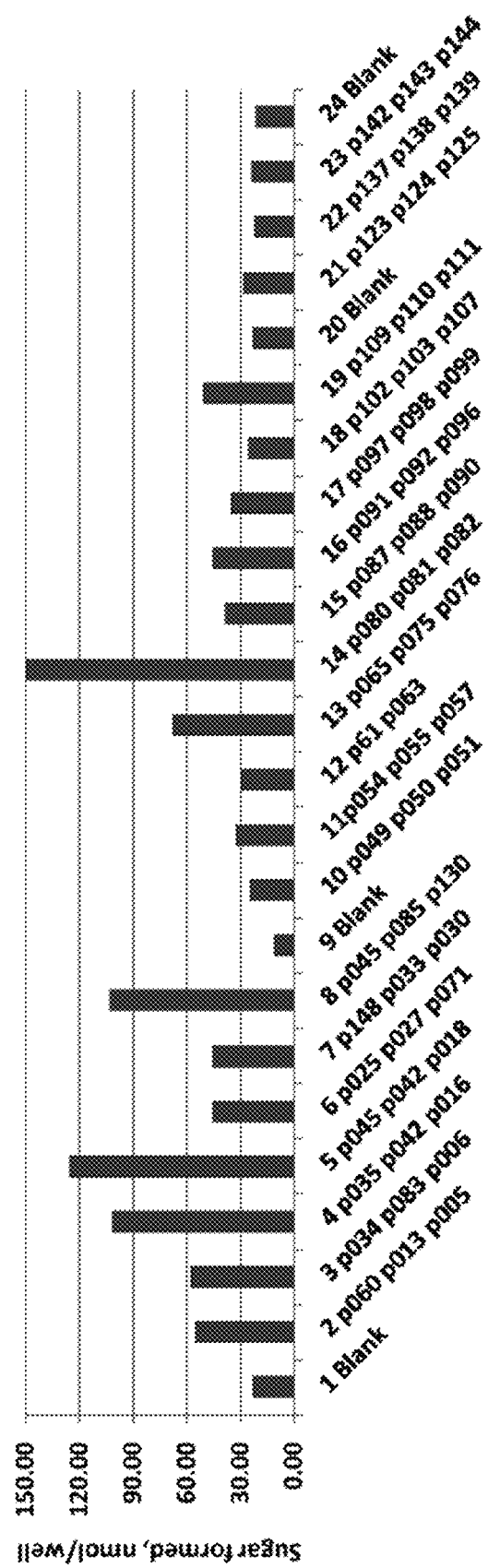
FIG. 1 is a histogram depicting sugar release from dehydrated *P. aeruginosa* biofilm treated with carbohydrate-active enzymes mixtures. Samples contained 500 µl sterile PBS plus 30 µl OF combined enzymes (10 µl of each of three (3) enzymes containing 100 µg protein) or 30 µl of sterile PBS (blank). Samples were incubated at 37° C., 500 rpm on an Eppendorf Thermomixer. Plates were centrifuged after 19 hr incubation and 0.15 ml of sample was removed for analysis by phenol-sulfuric acid method.

The enzymes of the invention have biofilm-degrading activity and comprise amino acid sequences represented by SEQ ID NO:3, SEQ ID NO:6, SEQ ID NO:9, SEQ ID NO:12, SEQ ID NO:15, SEQ ID NO: 18, SEQ ID NO:21, SEQ ID NO:24 and sequence variants thereof, i.e., variants of any of the previously listed sequences. SEQ ID NO:2, SEQ ID NO:5, SEQ ID NO:8, SEQ ID NO:11, SEQ ID NO:14, SEQ ID NO:17, SEQ ID NO: 20, and SEQ ID NO:23 are precursors of SEQ ID NO:3, SEQ ID NO:6, SEQ ID NO:9, SEQ ID NO:12, SEQ ID NO:15, SEQ ID NO: 18, SEQ ID NO:21, and SEQ ID NO:24, respectively, and are converted to the latter set of sequences by cleavage of an N-terminal portion therefrom.

The term "sequence variants" refers to enzymes that retain the biofilm-degrading activity or any other activity described herein (without regard to the degree of the activity) and have at least about 80% identity, at least about 85% identity, at least about 90% identity, at least about 95% identity, or at least about 98% or 99% identity, to the amino acid sequences provided herein. Percent identity may be determined using the algorithm of Karlin and Altschul (Proc. Natl. Acad. Sci. 87: 2264-68 (1990), modified Proc. Natl. Acad. Sci. 90: 5873-77 (1993). Such algorithm is incorporated into the BLASTx program, which may be used to obtain amino acid sequences homologous to a reference polypeptide, as is known in the art.

The term "sequence variants" may also be used to refer to proteins having amino acid sequences including conservative amino acid substitutions, unless explicitly stated otherwise. "Conservative amino acid substitution" refers to the replacement of one amino acid by an amino acid having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, phenylalanine, methionine, tryptophan), beta-branched side chains (e.g., threonine, valine, isoleucine), and aromatic side chains (e.g., tyrosine, phenylalanine, tryptophan, histidine).

The term "sequence variants" also refers to proteins that are subjected to site-directed mutagenesis wherein one or more substitutions, additions or deletions may be introduced.

The term "sequence variants" also refers to homologs. Homologs can be identified by homologous nucleic acid and polypeptide sequence analyses. Known nucleic acid and polypeptide sequences in one organism can be used to identify homologous polypeptides in another organism. For example, performing a query on a database of nucleic acid or polypeptide sequences can identify homologs thereof. Homologous sequence analysis can involve BLAST or PSI-BLAST analysis of databases using known polypeptide amino acid sequences (see, e.g., Altschul et al., 1990). Those proteins in the database that have greater than 35% sequence identity are candidates for further evaluation for suitability in the systems and methods of the invention. If desired, manual inspection of such candidates can be carried out in order to narrow the number of candidates that can be further evaluated. Manual inspection is performed by selecting those candidates that appear to have conserved domains. Determining nucleic acid sequences from discovered homologous amino acid sequences or amino acid sequences from discovered homologous nucleic acid sequences can be deduced using the genetic code.

The term "sequence variants" also refers to fragments of the sequences described herein. "Fragment" means a portion of the full length sequence. For example, a fragment of a given polypeptide is at least one amino acid fewer in length than the full length polypeptide (e.g. one or more internal or terminal amino acid deletions from either amino or carboxy-termini). Fragments therefore can be any length up to, but not including, the full length polypeptide. Suitable fragments of the polypeptides described herein include but are not limited to those having 80%, 85%, 90%, 95%, 96%, 97%, 98%, 99% or more of the length of the full length polypeptide.

The term "sequence variants" also refers to repeating units of the sequences described herein. "Repeating units" means a repetition of a given sequence in tandem. Also included are polypeptides having repeating units of fragments of the sequences described herein.

The enzymes of the invention are preferably prepared in a substantially purified form. As used herein, the term "purified" refers to material that is at least partially separated from components which normally accompany it in its native state. The purity of polypeptides may be determined using analytical techniques such as polyacrylamide gel electrophoresis or high performance liquid chromatography. A polypeptide that is the predominant species present in a preparation, such as a preparation containing the polypeptide that gives rise to essentially one band in an electrophoretic gel, is "substantially purified." The enzymes of the invention are at least about 85% pure, more preferably at least about 95% pure, and most preferably at least about 99% pure.

The enzymes of the invention can be generated by expressing polynucleotides encoding the enzymes. Suitable polynucleotides encoding the enzymes of the invention have the nucleotide sequences shown in SEQ ID NO:1, SEQ ID NO:4, SEQ ID NO:7, SEQ ID NO:10, SEQ ID NO:13, SEQ ID NO:16, SEQ ID NO:19, SEQ ID NO:22 and sequence variants thereof. The polypeptides generated by expressing such polynucleotides are cleaved to form the mature forms of the enzymes. Alternatively, fragments of the above-mentioned polynucleotides, i.e., those encoding the mature forms of the polypeptides, can be directly expressed.

The polynucleotides can be included in DNA constructs useful in preparing the polypeptides of the invention. The DNA constructs may include at least one polynucleotide encoding a polypeptide described herein operably connected to a promoter. The promoter may be natively associated with the coding sequence or may be heterologous. "Heterologous" refers to sequence portions not natively associated with a sequence. Suitable promoters are constitutive and inducible promoters. A "constitutive" promoter is a promoter that is active under most environmental and developmental conditions. Examples of constitutive promoters include but are not limited to T7 promoters, cytomegalovirus promoters such as the CMV immediate early promoter, SV40 early promoter, mouse mammary tumor virus promoter, human immunodeficiency virus promoters such as the HIV long terminal repeat promoter, maloney virus promoter, Epstein Barr virus promoter, rous sarcoma virus promoter, ALV, B-cell specific promoters, and baculovirus promoter for expression in insect cells. An "inducible" promoter is a promoter that is under environmental or developmental regulation. Examples of inducible promoters include the lac promoter, such as the lacUV5 promoter or the T7-lac promoter, copper-inducible promoters (Gebhart et al. Eukaryotic Cell 2006 5(6):935-44), and "tet-on" and "tet-off" promoters.

The term "operably connected" refers to a functional linkage between a promoter and a second nucleic acid sequence, wherein the promoter directs transcription of the nucleic acid corresponding to the second sequence. The constructs may suitably be introduced into host cells, such as *E. coli* or other suitable hosts known in the art for producing the enzymes of the invention.

Hosts capable of producing the enzymes described herein include both eukaryotic and prokaryotic hosts, such as mammalian-, bacterial-, fungal-, and insect-derived hosts. Examples of bacterial hosts include *Escherichia, Salmonella, Bacillus, Clostridium, Streptomyces, Staphyloccus, Neisseria, Lactobacillus, Shigella*, and *Mycoplasma*. *E. coli* strains, such as BL21(DE3), C600, DH5αF', HB101, JM83, JM101, JM103, JM105, JM107, JM109, JM110, MC1061, MC4100, MM294, NM522, NM554, TGI, χ1776, XL1-Blue, and Y1089+, all of which are commercially available. Other expression hosts are well known in the art.

The enzymes of the invention may be combined, delivered, administered, or otherwise used with an antimicrobial agent. The antimicrobial agent is preferably a selective antimicrobial agent, as opposed to a non-selective disinfectant such as bleach. Suitable antimicrobial agents include antibiotics, which are antimicrobial agents effective against bacteria, and antifungals, which are effective against fungi.

Suitable antibiotics include but are not limited to aminoglycosides, including amikacin, apramycin, arbekacin, astromicin, bekanamycin, capreomycin, dibekacin, dihydrostreptomycin, elsamitrucin, fosfomycin, tobramycin, gentamicin, hygromycin, isepamicin, kanamycin, kasugamycin, lividomycin, micronomicin, neamine, neomycin, netilmicin, paromomycin, ribostamycin, sisomicin, spectinomycin, streptoduocin, streptomycin, tobramycin, and verdamicin; ansamycins, including geldanamycin, herbimycin rifaximin, and streptomycin; carbacephems, including loracarbef; carbapenems, including ertapenem, doripenem, imipenem, cilastatin, and meropenem; cephalosporins, including cefadroxil, cefazolin, cefalotin, cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole; glycopeptides, including teicoplanin, vancomycin, and telavancin; lincosamides, including clindamycin and lincomycin; lipopeptides, including daptomycin; macrolides, including azithromycin, clarithromycin, dirithromycin, erythromycin, roxithromycin, troleandomycin, telithromycin, and spiramycin; monobactams, including aztreonam; nitrofurans, including furazolidone and nitrofurantoin; oxazolidonones, including linezolid, posizolid, radezolid, and torezolid; penicillins, including amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin; antibiotic polypeptides, including bacitracin, colistin, and polymyxin B; quinolones, including ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin; sulfonamides, including mafenide, sulfacetamide, sulfadiazine, silver, sulfadiazine, sulfadimethoxine, sulfamethizole, sulfamethoxazole, sulfanilamide, sulfasalazine, sulfisoxazole, trimethoprim-sulfamethoxazole (co-trimoxazole) (TMP-SMX), and sulfonamidochrysoidine; tetracyclines, including demeclocycline, doxycycline, minocycline, oxytetracycline, and tetracycline; anti-mycobacteria antibiotics, including clofazimine, dapsone, capreomycin, cycloserine, ethambutol, ethionamide, isoniazid, pyrazinamide, rifampicin (rifampin), rifabutin, rifapentine, and streptomycin; arsphenamine; chloramphenicol; fosfomycin; fusidic acid; metronidazole; mupirocin; ofloxacin; platensimycin; quinupristin/dalfopristin; thiamphenicol; tigecycline; tinidazole and trimethoprim; among others.

Suitable antifungals include but are not limited to polyene antifungals, including amphotericin B, candicidin, filipin, hamycin, natamycin, nystatin, and rimocidin; imidazoles, including bifonazole, butoconazole, clotrimazole, econazole, fenticonazole, isoconazole, ketoconazole, miconazole, omoconazole, oxiconazole, sertaconazole, sulconazole, and tioconazole; triazoles, including albaconazole, fluconazole, isavuconazole, itraconazole, posaconazole, ravuconazole, terconazole, and voriconazole; thiazoles, including abafungin; allylamines, including amorolfin, butenafine, naftifine, and terbinafine; echinocandins, including anidulafungin, caspofungin, and micafungin; and others, including benzoic acid, caprylic acid, ciclopirox, cuprimyxin, flucytosine or 5-fluorocytosine, griseofulvin, haloprogin, iodochlorohydroxyquin, proprionic acid, polygodial, salicylic acid, tolnaftate, undecylenic acid, and crystal violet; among others.

The enzymes and antimicrobial agents of the invention may be complexed with one or more counter-ions to form a salt. A host of suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a desired salt by ion exchange procedures. Suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. Other suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.*, 66: p. 1-19 (January 1977), both of which are incorporated herein by reference. In some versions of the invention, the salts are pharmaceutically suitable salts. The term "pharmaceutically suitable salt" refers to any acid or base addition salt whose counter-ions are non-toxic to the patient in pharmaceutical doses of the salts, so that the beneficial effects inherent in the free base or free acid are not vitiated by side effects ascribable to the counter-ions.

The compositions of the invention comprise pharmaceutical compositions. The pharmaceutical compositions comprise one or more active ingredients together with a pharmaceutically acceptable carrier therefor. The active ingredients may comprise one or more enzymes as described herein either with or without one or more antimicrobial agents as described herein. The pharmaceutical composition may further comprise other therapeutically active substances in addition to the above-noted ingredients. In a pharmaceutical composition of the invention, the carrier is pharmaceutically acceptable in the sense of being compatible with other ingredients in the particular composition and not deleterious to the recipient thereof. The compositions include those suitable for oral, topical, rectal, or parenteral (including subcutaneous, intramuscular, intradermal and intravenous) administration.

The pharmaceutical compositions may comprise the active ingredients in unit dosage form. The term "unit dosage" or "unit dose" is denoted to mean a predetermined amount of the active ingredients sufficient to be effective for treating each of the indicated activities. Preferred unit dosage formulations are those containing a daily dose, daily sub-dose, or an appropriate fraction thereof, of the active ingredients.

The pharmaceutical compositions may be prepared by any of the methods well known in the art of pharmacy. All methods include the step of bringing the active ingredients into association with the carrier. In general, the compositions are prepared by uniformly and intimately bringing the active ingredients into association with a liquid or solid carrier and then, if necessary, shaping the product into the desired unit dosage form.

Compositions of the present invention suitable for oral administration may be presented in a discrete solid form, e.g., as capsules, cachets, tablets, boluses, lozenges and the like, each containing a predetermined amount of the active ingredient; in powder or granular form; or in liquid form, e.g., as a collyrium, suspension, solution, syrup, elixir, emulsion, dispersion and the like. A tablet may be made by compression or molding, optionally with one or more accessory ingredients. Compressed tablets may be prepared by compressing in a suitable machine the active ingredients in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered active ingredients with any suitable carrier.

Compositions suitable for parenteral administration may comprise a sterile injectable preparation of the active ingredients in, for example, a solution which is preferably isotonic with the blood of the recipient. Useful formulations also comprise concentrated solutions or solids containing the active ingredients which upon dilution with an appropriate diluent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredients formulated into pharmaceutically-acceptable topical carriers by conventional methodologies. Common formulations include drops, collyriums, aerosol sprays, lotions, gels, ointments, plasters, shampoos, transferosomes, liposomes and the like. In topical formulations, the active ingredients are preferably utilized at concentrations of from about 0.1% to about 5.0% by weight.

Compositions suitable for rectal administration may comprise a suppository, preferably bullet-shaped, containing the active ingredients and a pharmaceutically-acceptable carrier therefor such as hard fat, hydrogenated cocoglyceride, polyethylene glycol and the like. Compositions suitable for rectal administration may alternatively comprise the active ingredient and pharmaceutically-acceptable liquid carriers therefor such as 50% aqueous ethanol or an aqueous salt solution which is physiologically compatible with the rectum or colon. In rectal formulations, the active ingredients are preferably utilized at concentrations of from about 0.1 to about 10% by weight.

Compositions suitable for inhalation may include a micronized powder or liquid formulation having a particle size in the range of from about 5 microns or less to about 500 microns, for rapid inhalation through the nasal or oral passage from a conventional inhalation squeeze or spray container. Suitable liquid nasal compositions include conventional nasal sprays, nasal drops and the like comprising solutions of the active ingredients and optional adjuvants.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like.

The amount of active ingredient required to be effective for each of the indicated activities will vary with the individual animal being treated and is ultimately at the discretion of the medical or veterinary practitioner. The factors to be considered include the species and sex of the animal, the condition being treated, the route of administration, the nature of the formulation, the animal's body weight, surface area, age and general condition, and the particular agents to be administered.

In general, the pharmaceutical compositions of this invention contain from about 0.5 to about 500 mg and, preferably, from about 5 to about 350 mg of each active ingredient, preferably in a unit dosage form, for each of the indicated activities. A suitable effective dose may be in the range of about 0.1 to about 200 mg/kg body weight per day for each active ingredient, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In some versions of the invention, the active ingredients (i.e., the enzyme with or without the antimicrobial agent) are included in the composition in biofilm-degrading amounts. The term "degrade" or grammatical variants thereof, used with regard to degrading biofilm with a particular agent or amounts therefor, refers to any degree of degradation of any portion of a biofilm, such as the releasing of sugars therefrom or other forms of degradation described in the following examples. Unless explicitly specified, "degrade" does not require complete ablation an entire pre-formed biofilm or even a reduction in the steady-state size or mass of the biofilm. For example, degradation of a biofilm may occur without a reduction in the steady-state size or mass of the biofilm if the rate of formation is equal to the rate of enzyme- or enzyme- and antimicrobial agent-dependent degradation. "Disrupting" and "degrading are used herein interchangeably.

In some versions of the invention, the active ingredients (i.e., the enzyme with or without the antimicrobial agent) are included in the composition in biofilm-inhibiting amounts. The term "inhibit" or grammatical variants thereof, used with regard to inhibiting formation of biofilm with a particular agent or amounts therefor, refers to any slowing of the rate of biofilm formation with respect to the rate of biofilm formation in the absence of the agent. Unless explicitly specified, "inhibit" does not required complete prevention of biofilm formation or growth.

The enzymes of the invention may be used to degrade a biofilm with or without the antimicrobial agents described herein. Such methods for degrading a biofilm preferably comprise contacting the biofilm with a biofilm-degrading amount of one or more enzymes either alone or in combination with a biofilm-degrading amount of one or more antimicrobial agents. Any combinations of the enzymes disclosed herein or the antimicrobial agents disclosed herein can be used.

The contacted biofilm may be an animal-associated biofilm or an animal-independent biofilm. For the purposes herein, "animal-associated biofilm" refers to biofilms growing or existing in an environment provided by the animal's body, whether on the surface of the body (as in the case of a biofilm resulting from a topical skin infection or a biofilm occurring on a catheter at the entry point into the body) or under the surface of the body (i.e., in the lungs, digestive tract, vascular system, etc., or on implanted devices in such areas of the body). "Animal-independent biofilm" refers to biofilms growing or existing in an environment other than an environment provided by the animal's body, such as on petri dishes, in water or sewage pipes, on boat hulls, etc.

The contacting may comprise delivering the enzyme and/or the antimicrobial agent to the biofilm in a suitable composition. For animal-independent biofilms, the delivering may comprise applying the enzyme and/or the antimicrobial agent in a suitable composition directly to the biofilm. For animal-associated biofilms, the delivering may comprise administering the animal the enzyme and/or the antimicrobial agent in a composition and administration format suitable for accessing the biofilm within the animal.

In versions in which the biofilm is contacted with both the enzyme and the antimicrobial agent, the enzyme and antimicrobial agent may be delivered to the biofilm either simultaneously or non-simultaneously.

Delivering the biofilm simultaneously may comprise simultaneously applying, administering, or otherwise delivering the enzyme and antimicrobial agent either in separate compositions or in the same composition to the biofilm. If simultaneously delivered in separate compositions, the commencement of the respective deliveries may be staggered, provided the respective deliveries overlap at some point. Delivery of the enzyme may begin at least about 0.25 hours, at least about 0.5 hours, or at least about 1 hour or more prior to beginning delivery of the antimicrobial agent. For example, delivery of the enzyme may begin between about 0.25 and about 10 hours, between about 0.5 and about 7 hours, or between about 1 and about 4 hours prior to beginning delivery of the antimicrobial agent. For simultaneously delivering the enzyme and the antimicrobial agent in separate compositions wherein commencement of the respective deliveries is staggered, continuous delivery formats, such as infusion, extended topical application, or continuous liquid bathing, as opposed to punctuated delivery formats, such as injection or oral administration, are used.

Delivering the biofilm non-simultaneously may comprise sequentially applying, administering, or otherwise delivering the enzyme and antimicrobial agent in separate compositions to the biofilm wherein the respective deliveries do not overlap. The antimicrobial agent may be delivered at least about 0.25 hours, at least about 0.5 hours, or at least about 1 hour or more after delivery of the enzyme is completed. For example, the antimicrobial agent may be delivered between about 0.25 and about 10 hours, between about 0.5 and about 7 hours, or between about 1 and about 4 hours after delivery of the enzyme is completed.

In order to elicit the greatest amount of degradation possible, the biofilm contacted with an enzyme and an antimicrobial agent is preferably at least in part formed by and comprises a microorganism that is sensitive in its planktonic state to the particular antimicrobial agent. Without being bound by mechanism, it is surmised that contacting the biofilm with the enzyme at least partially degrades the biofilm, thereby enhancing the susceptibility of the biofilm-associated microorganisms to the antimicrobial agent. Microorganisms that are thereby killed or inhibited from reproducing no longer contribute to formation of the biofilm. In some cases, the combined activities of the enzyme and the antimicrobial agent provide a synergistic effect in degrading the biofilm to the point of reducing its overall size or mass. See the examples below. The particular antimicrobial agents that are effective against particular microorganisms in their planktonic states are known in the art.

Because the enzymes enhance the susceptibility of the biofilm-associated microorganisms to antimicrobial agents, the antimicrobial agents can be delivered or administered at lower concentrations than those typically used against biofilm-associated microorganisms. Preferred concentrations include those greater than the concentration effective to kill or inhibit reproduction of the microorganism in the planktonic state and lower than the concentration effective to kill or inhibit reproduction of the microorganism in the biofilm-associated state.

Nearly every species of microorganism, including bacteria, fungi, and archaea, have mechanisms for forming biofilms. Therefore, the microorganisms comprised within the biofilm and rendered susceptible by contacting the biofilm with the enzyme and antimicrobial agent can comprise any type of microorganism. Exemplary types of microorganisms include bacteria and fungi. Exemplary types of bacteria include gram-positive, gram-negative, and mycoplasma-type bacteria. Exemplary types of fungi include yeasts and molds.

Specific types of bacteria that may be comprised within the biofilm and rendered susceptible by contacting the biofilm with the enzyme and, optionally, the antimicrobial agent include *Aeromonas* spp., including *Aeromonas caviae*, *Aeromonas hydrophila*, and *Aeromonas veronii*; *Actinomyces* spp., including *Actinomyces naeslundii*; *Bacillus* spp., including *Bacillus anthracis* and *Bacillus subtilis*; *Bacteroides* spp., including *Bacteroides forsythus*, *Bacteroides gingivalis*, *Bacteroides intermedius*, and *Bacteroides pneumosintes*; *Bordetella* spp., including *Bordetella pertussis*; *Borrelia* spp., including *Borrelia burgdorferi*; *Brucella* spp., including *Brucella abortus*, *Brucella canis*, *Brucella melitensis*, and *Brucella suis*; *Burkholderia* spp., including *Burkholderia cepacia*; *Campylobacter* spp., including *Campylobacter jejuni*; *Chlamydia* spp., including *Chlamydia pneumonia* and *Chlamydia trachomatis*; *Chlamydophila* spp., including *Chlamydophila psittaci*; *Citrobacter* spp.; *Clostridium* spp., including *Clostridium botulinum*, *Clostridium difficile*, *Clostridium perfringens*, and *Clostridium tetani*; *Corynebacterium* spp., including *Corynebacterium glutamicum* and *Corynebacterium diphtheriae*; *Enterobacter* spp.; Enterobacteriaceae; *Enterococcus* spp., including *Enterococcus faecalis*; *Escherichia* spp., including *Escherichia coli*; *Eubacterium* spp., including *Eubacterium brachy* and *Eubacterium timidum*; *Fusobacterium* spp., including *Fusobacterium nucleatum*; *Francisella* spp., including *Francisella* tularensis; *Gardnerella* spp.; *Haemophilus* spp., including *Haemophilus aphrophilus* and *Haemophilus influenza*; *Helicobacter* spp., including *Helicobacter pylori*; *Klebsiella* spp.; *Lactobacillus* spp.; *Leptospira* spp., including *Leptospira interrogans*; *Legionella* spp., including *Legionella pneumophila*; *Leptospira* spp., including *Leptospira interrogans*; *Listeria* spp., including *Listeria monocytogenes*; *Moraxella* spp., including *Moraxella catarrhalis*; *Mycobacterium* spp., including *Mycobacterium leprae*, *Mycobacterium tuberculosis*, and *Mycobacterium ulcerans*; *Mycoplasma* spp., including *Mycoplasma pneumoniae*; *Neisseria* spp., including *Neisseria gonorrhoeae* and *Neisseria meningitidis*; *Peptostreptococcus* spp., including *Peptostreptococcus micros*; *Porphyromonas* spp., including *Porphyromonas gingivalis*; *Proteus* spp.; *Pseudomonas* spp., including *Pseudomonas aeruginosa* and *Pseudomonas anaerobius*; *Rickettsia* spp., including *Rickettsia rickettsii*; *Salmonella* spp., including *Salmonella typhi* and *Salmonella typhimurium*; *Selenomonas* spp., including *Selenomonas sputigena*; *Serratia* spp.; *Shigella* spp., including *Shigella sonnei*; *Staphylococcus* spp., including *Staphylococcus aureus*, *Staphylococcus capitus*, *Staphylococcus epidermidis*, *Staphylococcus saprophyticus*, and coagulase-negative Staphylococci; *Streptococcus* spp., including *Streptococcus agalactiae*, *Streptococcus bovis* *Streptococcus pneumonia*, and *Streptococcus pyogenes*; *Treponema* spp., including *Treponema pallidum*; *Vibrio* spp., including *Vibrio cholerae*; *Wolinella* spp., including *Wolinella* recta; and *Yersinia* spp., including *Yersinia pestis*. See, e.g., Donlan et al.

Specific types of fungi that may be comprised within the biofilm and rendered susceptible by contacting the biofilm with the enzyme and, optionally, the antimicrobial agent include *Candida* spp., including *Candida albicans, Candida dubliniensis, Candida parapsilosis, Candida tropicalis, Candida parapsilosis*, and *Candida glabrata*; *Aspergillus* spp., including *Aspergillus clavatus, Aspergillus, fumigatus*, and *Aspergillus flavus*; *Cryptococcus* spp., including *Cryptococcus gattii* and *Cryptococcus neoformans*; *Trichosporon* spp., including *Trichosporon asahii*; *Coccidioides* spp., including *Coccidioides immitis* and *Coccidioides neoformans*; *Histoplasma* spp., including *Histoplasma capsulatum*; *Pneumocystis* spp., including *Pneumocystis carinii*; and *Stachybotrys* spp., including *Stachybotrys chartarum*. See, e.g., Fanning et al. (Fungal Biofilms. *PLoS Pathog* 8(4): e1002585).

Because the enzyme-dependent degradation of the biofilm renders antimicrobial-resistant microorganisms comprised within the biofilm sensitive to antimicrobial agents, the methods of contacting a biofilm with at least one enzyme and at least one antimicrobial agent described herein can be used to treat a microbial infection associated with the biofilm in an animal. The treating preferably comprises administering at least one enzyme and at least one antimicrobial agent to the animal as described above. The treated infection may comprise an infection with any of the microorganisms described herein, including any of the types of bacteria or fungi described herein. The animal preferably comprises a mammal and more preferably comprises a human. The animal administered the at least one enzyme and the at least one antimicrobial agent may be known or suspected of having an infection with any of the microorganisms described herein. Preferred concentrations of the at least one antimicrobial agent include those greater than the concentration effective to kill or inhibit reproduction of the microorganism in the planktonic state and lower than the concentration effective to kill or inhibit reproduction of the microorganism in the biofilm-associated state.

Animals suspected of having an infection with any of the microorganisms described herein may comprise those having a disease or condition associated with or linked to biofilms. Exemplary diseases or conditions associated with or linked to biofilms include atherosclerosis, bacterial pneumonia, bacterial vaginosis, catheter-associated infections, chronic sinusitis, chronic wounds, cystic fibrosis, gastroenteritis, gingivitis, endocarditis, implant-associated infections, inner and middle ear infections, kidney stones, leptospirosis, osteomyelitis, osteonecrosis and osteomyelitis of the jaw, periodontal disease, pneumonia, prosthetic joints and heart valves, skin infections (impetigo, erysipelas, cellulitis, etc.), urinary tract infections, chronic bacterial prostatitis, native valve endocarditis, otitis media (particularly chronic), prosthetic valve endocarditis, endophthalmitis, tuberculosis, among others. See, e.g., Donlan et al. Other animals suspected of having an infection with any of the microorganisms described herein may comprise a medical device or an implant prone to biofilm formation. Exemplary medical devices or implants prone to biofilm formation include prosthetic heart valves, catheters of all types (central venous catheters, urinary (Foley) catheters, etc.), contact lenses, intrauterine devices, intraocular lenses, prosthetic hip joints, cardiac pacemakers, prosthetic heart valves, vascular prostheses (stents, etc.), sutures, endotracheal tubes, and the like. See Donlan et al.

A preferred version of the invention comprises treating infections of *Pseudomonas aeruginosa* and/or other microorganisms associated with biofilms in the lung, as typically occurs in cystic fibrosis. The treating comprises administering one or more of the enzymes and one or more of the antimicrobial agents to an animal either known or suspected of suffering from *Pseudomonas aeruginosa* infection or suffering from cystic fibrosis. A preferred antimicrobial agent in the treatment includes any of the aminoglycoside antibiotics. A preferred aminoglycoside antibiotic includes tobramycin. A preferred method of administering the one or more enzymes and the one or more antimicrobial agents is through inhalation. The one or more enzymes and the one or more antimicrobial agents may be administered simultaneously or non-simultaneously. If administered non-simultaneously, the antimicrobial agents may be administered within about 1 to about 4 hours after administration of the enzymes.

Some versions of the invention comprise a method of inhibiting growth of biofilm on a surface. The method comprises contacting the surface with a biofilm-inhibiting amount of at least one of the enzymes described herein. In some versions, the surface may also be contacted with one of the antimicrobial agents described herein. Any combinations of the enzymes disclosed herein and, optionally, the antimicrobial agents disclosed herein can be used.

The contacted surface may be an animal-associated surface or an animal-independent surface. For the purposes herein, "animal-associated surface" refers to surfaces existing in an environment provided by the animal's body, whether on the surface of the body (such as the skin, teeth, inserted catheters, etc.) or under the surface of the body (i.e., in the lungs, digestive tract, vascular system, etc., or on implanted devices in such areas of the body). "Animal-independent surface" refers to surfaces existing in an environment other than an environment provided by the animal's body, such surfaces on petri dishes, in water or sewage pipes, on boat hulls, etc.

The contacting may comprise delivering the enzyme and/or the antimicrobial agent to the surface in a suitable composition. For animal-independent surfaces, the delivering may comprise applying the enzyme and/or the antimicrobial agent in a suitable composition directly to the surface. For animal-associated surfaces, the delivering may comprise administering the animal the enzyme and/or the antimicrobial agent in a composition and administration format suitable for accessing the surface within the animal. The conditions and formats described above for delivering the enzyme and/or the antimicrobial agent to biofilms apply to delivering the enzyme and/or the antimicrobial agent to surfaces.

For inhibiting biofilm formation on animal-associated surfaces, the enzyme and/or the antimicrobial agent is administered to an animal known or suspected of being infected with any type of microorganism described herein, known or suspected of suffering from any disease or condition associated with or linked to biofilms, or known or suspected of having a medical device or implant.

A preferred version comprises inhibiting biofilm formation in animals known or suspected of suffering from *Pseudomonas aeruginosa* infection and/or other microorganisms associated with biofilms in the lung, as typically occurs in cystic fibrosis. The inhibiting may comprise administering one or more of the enzymes described herein, preferably without but optionally in combination with one or more of the antimicrobial agents, to an animal either known or suspected of suffering from *Pseudomonas aeruginosa* infection or suffering from cystic fibrosis. A preferred antimicrobial agent in the treatment, if included, comprises an aminoglycoside antibiotic. A preferred aminoglycoside antibiotic includes tobramycin. A preferred method of administering the one or more enzymes either alone or with the one or more antimicrobial agents is through inhalation.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Background

Cystic fibrosis (CF) is an autosomal recessive genetic disease caused by a mutation in the cystic fibrosis transmembrane conductance regulator protein, a gated ion channel. CF affects paranasal sinuses as well as the lower respiratory, hepatobiliary, pancreatic and lower gastro-intestinal tracts. The current median age of survival for individuals with CF is approximately 38 years. Over 80% of CF mortalities are attributable to respiratory failure from chronic bacterial infections of the lungs, most commonly caused by *Pseudomonas aeruginosa*. Individuals with CF have impaired mucociliary clearance which results in airway mucus plugging. This creates hypoxic microenvironments, forcing invasive microbial species to adapt by forming biofilm, which is highly tolerant to most forms of antibiotic treatment.

There are currently two types of drug treatments directed at respiratory infections for cystic fibrosis. The first drug treatment uses recombinant human DNase (Dornase Alfa or Pulmozyme®—a registered trademark of Genentech, Inc.) to cleave neutrophil-derived DNA in sputum, which reduces viscosity and facilitates clearance from the lung; this does nothing to combat the underlying infection causing the accumulation of DNA-containing sputum. The second drug treatment uses antibiotics such as tobramycin, a frontline drug to kill the *Pseudomonas aeruginosa* residing in the lung. Even in combination, these two drugs are unable to clear chronic *P. aeruginosa* infections. A critical barrier to progress in combating these chronic *Pseudomonas* infections that affect CF patients is the biofilm produced by the cells makes them resistant to clearing by either the body's natural defenses or by antibiotic treatment. Current therapies only address the symptoms of *P. aeruginosa* infection and are ineffective as evidenced by the long, drawn-out morbidity and end-stage mortality of CF. Moreover, *P. aeruginosa* infections are also associated with chronic obstructive pulmonary disease and nosocomial infections such as pneumonia from invasive treatments.

The following examples show the efficacy of certain enzyme or enzyme and antibiotic combinations for degrading *P. aeruginosa* biofilms and killing the *P. aeruginosa* associated therewith for treatment of *P. aeruginosa* infection as found in CF.

Example 1

Evaluation of Carbohydrate-Active Enzymes for Hydrolysis of *Pseudomonas Aeruginosa* Biofilm Glycosyl hydrolases can be exo-acting, endo-acting, or possess both types of activity. For hydrolysis of biofilms, it was reasoned that strictly exo-acting enzymes would have little or no potential for digesting biofilm, while endo-acting enzymes would have high potential. A library of approximately 200 enzymes was screened for endo-acting glycosyl hydrolases enzymes using insoluble chromogenic substrate (AZCL®-brand azurin-insoluble, crossed-linked chromogenic carbon substrates; Megazyme, Wicklow, Ireland). From the entire library of glycosyl hydrolases, fifty-nine (59) enzymes showed strong activity on at least one insoluble substrate at neutral pH and 37° C. A significant number of other enzymes showed strong activity at acid or alkaline pH and 37° C., but little or no activity at neutral pH. The enzymes with little or no activity at neutral pH were eliminated from further consideration.

The collection of 59 enzymes was evaluated for biofilm digestion using sets of three different enzymes per well on the same 24-well plate containing *Pseudomonas aeruginosa* grown and dried on the walls of the plate. The entire collection of 59 enzymes included one (1) amylase, one (1) xyloglucanase, two (2) beta-glucanases, four (4) xylanases, six (6) mannanases, and thirty-five (35) cellulases. To insure the maximum likelihood of success, the sets of three enzymes were designed to provide a mixture of activities on different substrates. Plates were incubated overnight at 37° C., centrifuged, and the soluble carbohydrates measured using the micro version of the Modified Somogyi Method for reducing sugars (Nelson). To 50 μl aliquots of the clarified samples, 200 μl of Reagent D (1.0 ml of Reagent B (150.0 g/l of $CuSO_4 \cdot 5H_2O$ containing 20 drops of concentrated $H_2SO_4$/1) combined with 25.0 ml of Reagent A (25.0 g/l $Na_2CO_3$, 25.0 g/l $KNaC_4H_4O_6 \cdot 4H_2O$, and 200 g/l g $Na_2SO_4$)) was added. The samples were vortexed briefly and then incubated at 95° C. for 20 min. After incubation, the tubes were vortexed, incubated at room temperature for 5 min, and 600 μl of Reagent E (10.0 g/l of $(NH_4)_6Mo_7O_{24} \cdot 4H_2O$, 1.20 g/l $Na_2HAsO_4 \cdot 7H_2O$, and 8.4 ml/l of concentrated $H_2SO_4$) was added to each sample. The samples were vortexed and incubated at room temperature for 15 min, then centrifuged for 2 min at 13,000 rpm to clarify. Aliquots, 200 μl each, were transferred to a 96-well microtiter plate and the absorbance determined at 590 nm. Micromoles of sugars formed were determined using a glucose standard curve, and unit activity was calculated as micromoles of reducing sugar per minute per milligram of protein.

Figure 2:
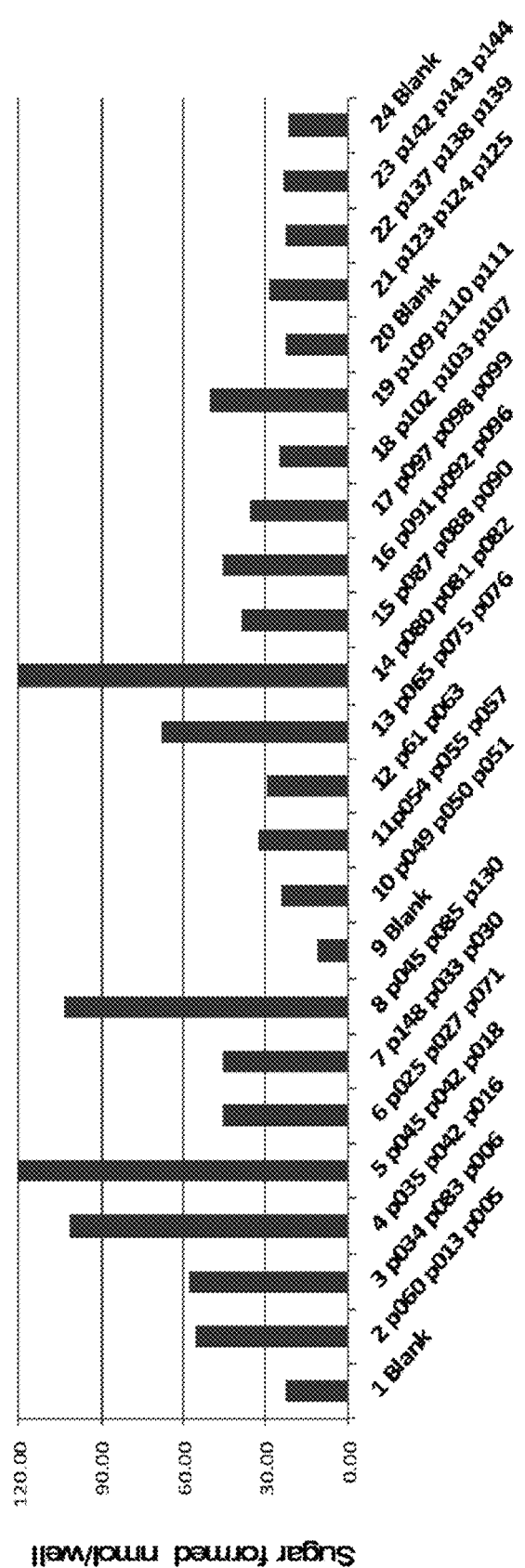
FIG. 2 is a histogram depicting sugar release from dehydrated *P. aeruginosa* biofilm treated with carbohydrate-active enzymes mixtures. Sample wells contained 500 µl of sterile PBS plus either 30 µl of combined enzymes (10 µl of each of three (3) enzymes containing 100 µg protein) or 30 µl of sterile PBS (blank). Samples were incubated and then analyzed as described in FIG. 1.

The results of replicated experiments, shown in FIGS. 1 and 2, show a surprising number of carbohydrate-active enzymes that solubilized sugars from the dehydrated *Pseudomonas aeruginosa* biofilm. These results suggested that individual enzymes alone may be sufficient to provide measurable solubilization of the biofilm.

Figure 3:
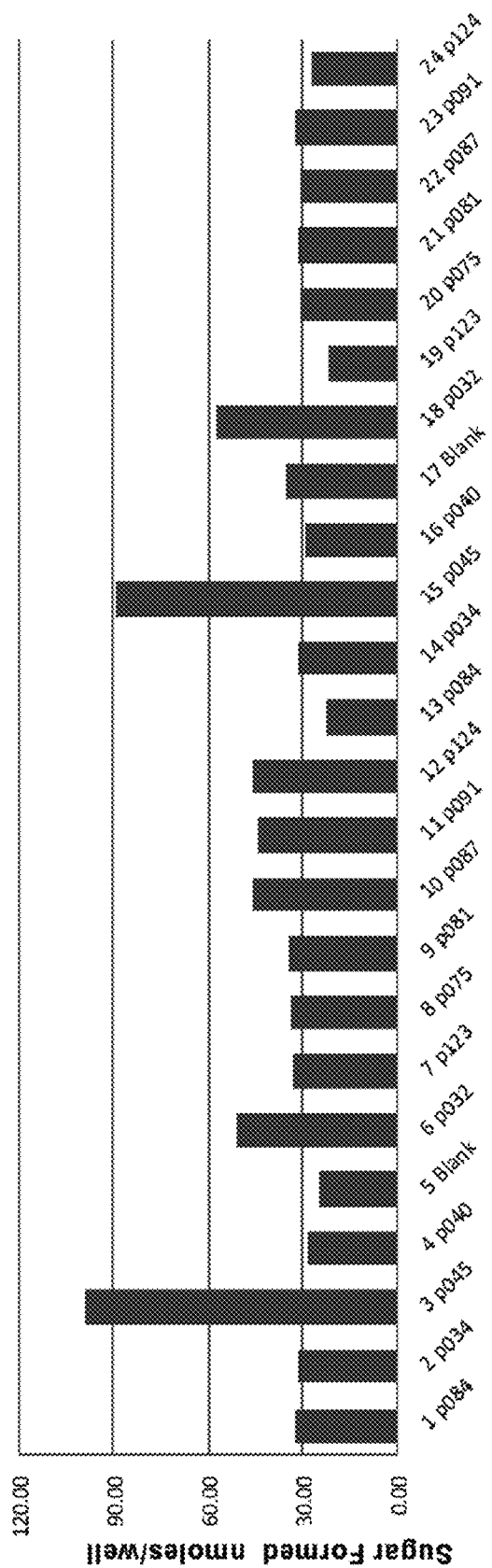
FIG. 3 is a histogram depicting sugar release from dehydrated *P. aeruginosa* biofilm treated with individual carbohydrate-active enzymes. Sample wells contained 500 µl of sterile PBS plus either 10 µl of enzyme or sterile PBS (blank). Samples were incubated and then analyzed as described in FIG. 1.
Figure 4:
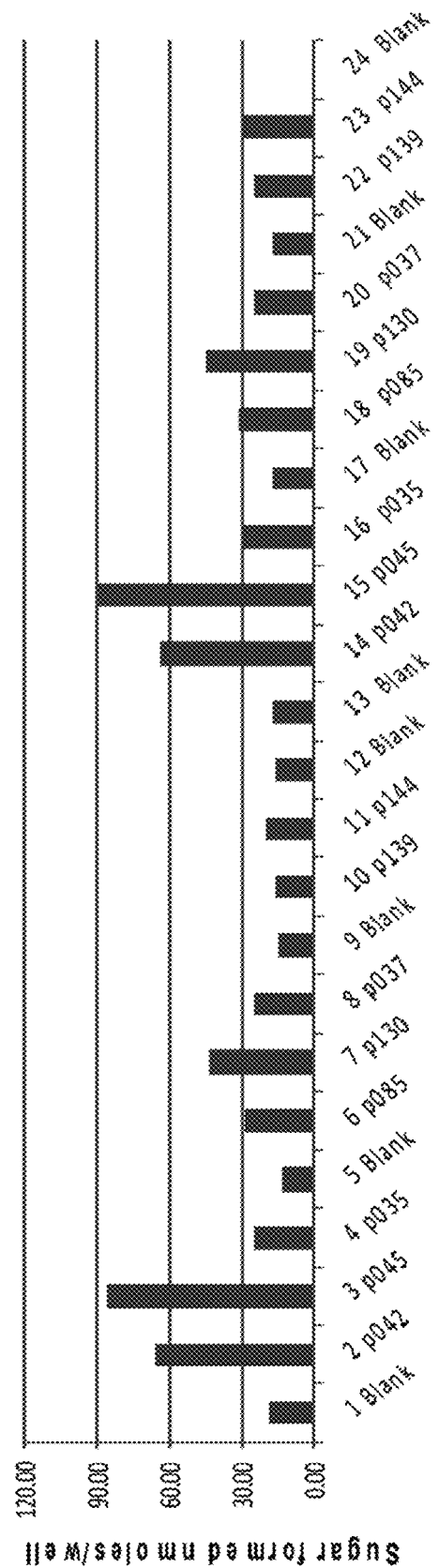
FIG. 4 is a histogram depicting sugar release from dehydrated *P. aeruginosa* biofilm treated with individual carbohydrate-active enzymes. Sample wells contained 500 µl of sterile PBS plus either 10 µl of enzyme or sterile PBS (blank). Samples were incubated and then analyzed as described in FIG. 1.

To test this hypothesis, each of the candidate enzymes was tested individually for its ability to solubilize the *Pseudomonas aeruginosa* biofilm. The results (depicted in FIGS. 3 and 4) show that three of the enzymes, P130, P042, and P045, gave significantly greater digestion of the biofilm than the other fifteen enzymes.

Figure 5:
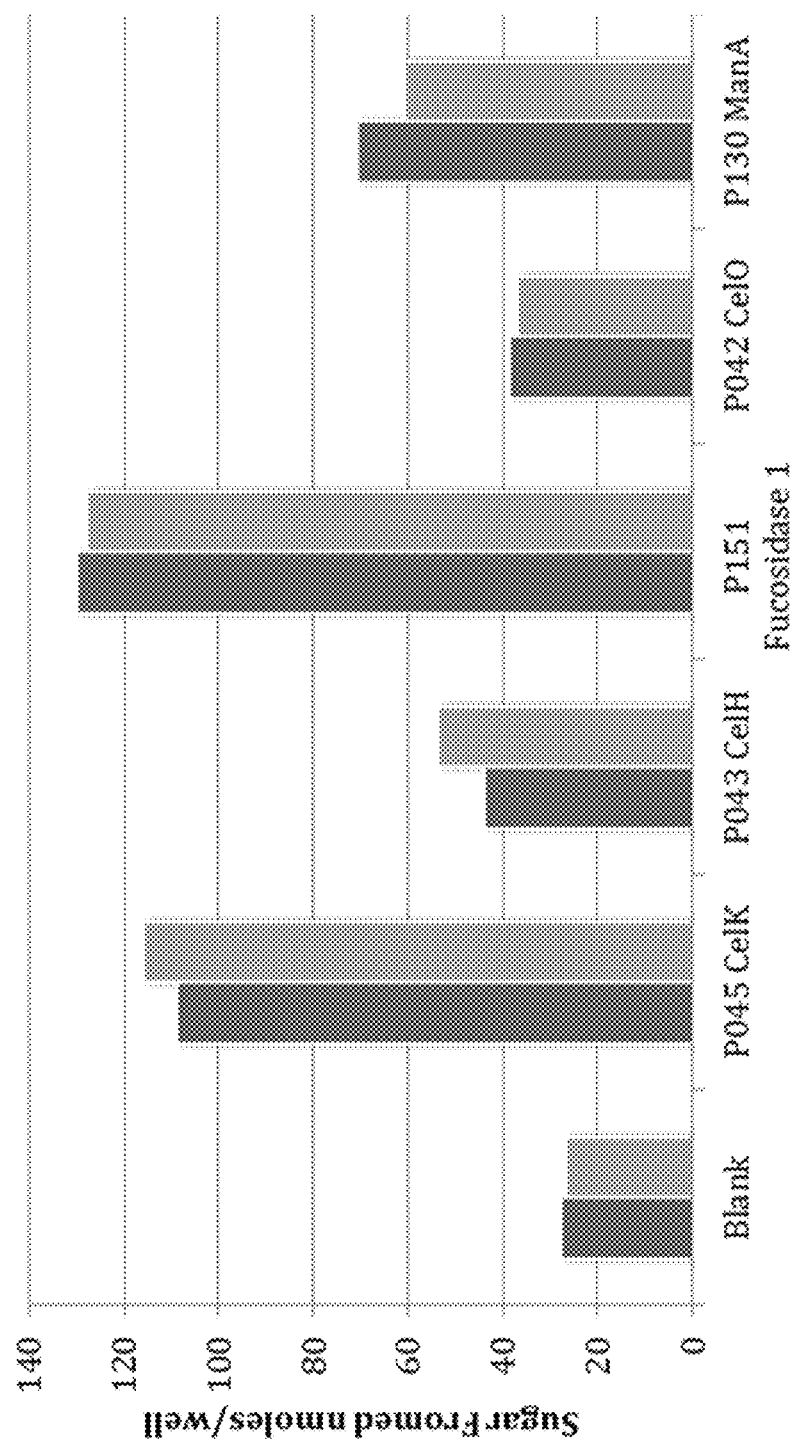
FIG. 5 is a histogram depicting sugar release from dehydrated *P. aeruginosa* biofilm treated with individual carbohydrate-active enzymes. Sample wells contained 500 μl of sterile PBS plus either 10 μl of enzyme or sterile PBS (blank). Samples were incubated and then analyzed as described in FIG. 1. Duplicate runs are shown. P045 CelK is the *Clostridium thermocellum* CelK enzyme (gene Cthe_0412) represented by SEQ ID NO:9. P043 CelH is the *Clostridium thermocellum* CelH enzyme (gene Cthe_1472) represented by SEQ ID NO:12. P151 Fucosidase 1 is the *Gibberella zeae* PH-1 hypothetical protein FG11254.1 (alpha-fucosidase) represented by SEQ ID NO:21. P042 CelOis the *Clostridium thermocellum* CelO enzyme (gene Cthe_2147) represented by SEQ ID NO: 6. P130 ManA is the *Clostridium thermocellum* ManA enzyme (gene Cthe_0032) represented by SEQ ID NO:3.

On the basis of protein sequences and previously measured activities, enzymes P042 and P045 are classified as cellulases and P130 as a beta-mannanase. P130 is the *Clostridium thermocellum* ManA enzyme (gene Cthe_0032) represented by SEQ ID NO:3; p042 is the *Clostridium thermocellum* CelO enzyme (gene Cthe_2147) represented by SEQ ID NO: 6, and p045 is the *Clostridium thermocellum* CelK enzyme (gene Cthe_0412) represented by SEQ ID NO:9. As shown in FIG. 5, positive results were also obtained with the *Clostridium thermocellum* CelH enzyme (gene Cthe_1472) represented by SEQ ID NO:12 ("P043 CelH" in FIG. 5) and the *Gibberella zeae* PH-1 hypothetical protein FG11254.1 (alpha-fucosidase) represented by SEQ ID NO:21 ("P151 Fucosidase 1" in FIG. 5).

To evaluate if all cellulases and mannanases give positive results, two additional cellulases and four additional mannanases were combined and compared to the best performers. The results indicated that only the previously identified enzymes produced significant solubilization of the biofilm. These results show that the enzyme activity needed for degrading the biofilm is not a non-specific cellulase or mannanase activity. In addition to these enzymes, alginate lyase (Sigma A1603), Protease S (Sigma 6361) and egg yolk lysozyme (Sigma L4919) were evaluated for efficacy in solubilizing the *Pseudomonas aeruginosa* biofilm. None of these three enzymes showed significant hydrolysis of the material (data not shown).

To determine the efficacy of biofilm removal, a number of methods were evaluated to measure the total amount of biofilm present in each well of the 24-well plate. Direct measurement in the plate was most desirable; however, the plates were unable to withstand the combination of strong acid and high temperature used for the assay. Sonication of individual wells containing phosphate buffered saline (PBS), followed by measurement of the carbohydrate solubilized yielded the most reproducible results. The results for the carbohydrate released by sonication was set at 100% and used to calculate the percentage solubilization achieved by the individual carbohydrate-active enzymes. An enzyme blank was used to remove any interfering substances present; the two cellulases (P042 and P045) solubilized approximately 50% of the biofilm carbohydrate while the mannanase (P130) solubilized approximately 20%. Based on the above data, the three enzymes selected for further evaluation were P042, P045, and P130.

Example 2

Inhibition of *Pseudomonas aeruginosa* Biofilm Formation

The carbohydrate-active enzymes were examined in a model of biofilm formation on an abiotic (plastic surface). The ability of the carbohydrate-active enzymes to "inhibit" biofilm formation of *P. aeruginosa* was assessed. The enzymes were added at the same time the biofilm assay was initiated to determine whether the enzymes could block *P. aeruginosa* biofilm formation. In this biofilm inhibition assay, enzymes were added to the bacteria in fresh growth medium (M63MgArg medium) inoculated with 1/100 dilution of an overnight (o/n) LB grown culture of *P. aeruginosa* PA14. Enzymes were added at 5 µl/per well, for a final concentration of ~0.02 mg/ml. After 6-8 hrs, the biofilms were detected by staining with the dye crystal violet, and quantitated at 550 nm as a measure of the biofilm formed.

Figure 6:
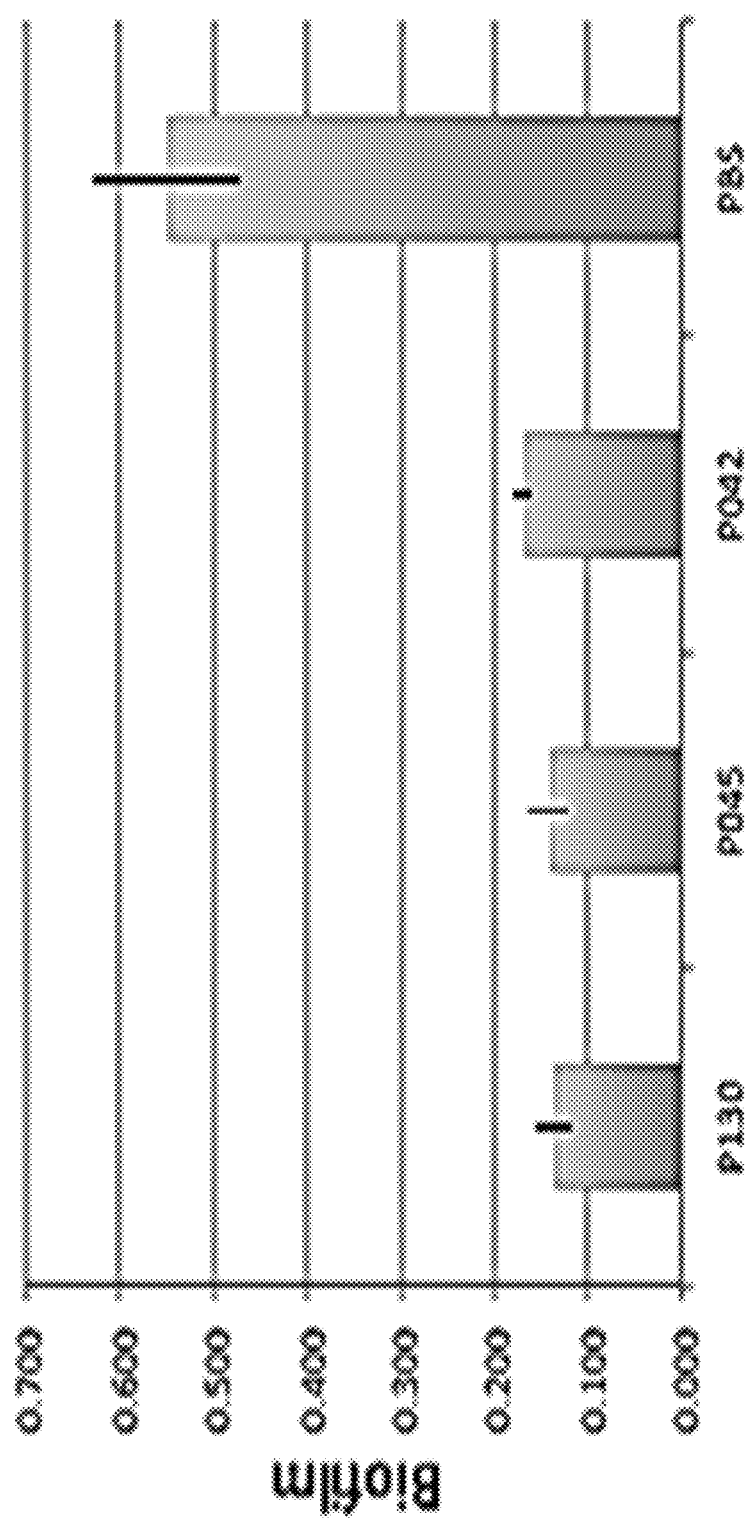
FIG. 6 is a histogram depicting biofilm inhibition via the present method. In this biofilm inhibition assay, enzymes were added to bacteria in fresh growth medium (M63MgArg medium) inoculated with 1/100 dilution of an overnight LB grown culture of *P. aeruginosa* PA14. Enzymes were added at 5 μl/per well, for a final concentration of ~0.02 mg/ml. After 6-8 hrs, the biofilms were detected by staining with the dye crystal violet, and quantified at 550 nm as a measure of the biofilm formed. P130 is the *Clostridium thermocellum* ManA enzyme (gene Cthe_0032) represented by SEQ ID NO:3. P045 is the *Clostridium thermocellum* CelK enzyme (gene Cthe_0412) represented by SEQ ID NO:9. P042 is the *Clostridium thermocellum* CelO enzyme (gene Cthe_2147) represented by SEQ ID NO: 6.
Figure 7:
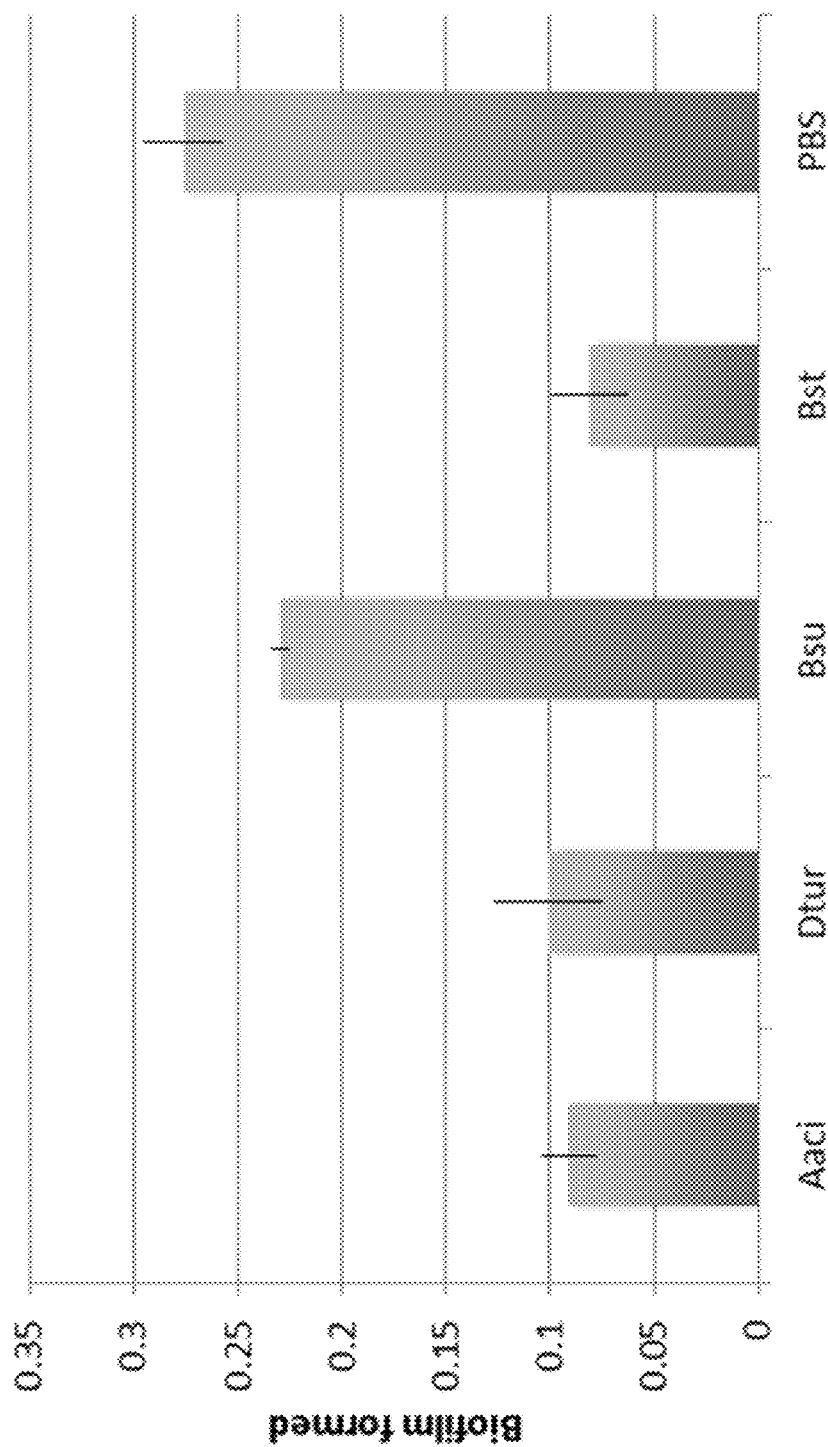
FIG. 7 is a histogram depicting biofilm inhibition via the present method using the assay described above for FIG. 6 but with a different set of enzymes. Aaci is the *Alicyclobacillus acidocaldarius* alpha-amylase represented by SEQ ID NO:24. Dtur is the *Dictyoglomus turgidum* AmyA enzyme (gene Dtur_0675) represented by SEQ ID NO:15. Bsu is the mature, processed form of the AmyE (AmyA) alpha-amylase from *Bacillus subtilis* (strain 168) represented by Uni-Prot Accession Number P00691. Bst is the *Bacillus stearothermophilus* AmyS enzyme (UniProt P06279) represented by SEQ ID NO: 18.

As shown in FIG. 6, biofilm formation was effectively inhibited on this abiotic surface by each of the P130, P045, and P042 carbohydrate-active enzymes compared to the PBS buffer control. Four amylases were also evaluated using the same assay format. As shown in FIG. 7, the *Alicyclobacillus acidocaldarius* alpha-amylase represented by SEQ ID NO:24 ("Aaci" in FIG. 7), the *Dictyoglomus turgidum* AmyA enzyme (gene Dtur_0675) represented by SEQ ID NO:15 ("Dtur" in FIG. 7), and the *Bacillus stearothermophilus* AmyS enzyme (UniProt P06279) represented by SEQ ID NO: 18 ("Bst" in FIG. 7) were shown to be effective in inhibiting the formation of biofilm. These results add weight to the observation that certain carbohydrate-active enzymes can degrade some portion of the *P. aeruginosa* exopolysaccharide. There is considerable evidence that *P. aeruginosa* biofilm can adhere to a number of different surfaces via its exopolysaccharide (Colvin et al.) and that interfering with this structure inhibits its ability to attach (Digiandomenico et al.). Thus, this result is highly relevant for preventing catheter-based biofilms from forming, and further indicates the utility of these enzymes for industrial applications. These results also indicate that *P. aeruginosa* does not produce apparent proteases or other inhibitors of the carbohydrate-active enzymes that prevent their activity during the time course of the experiment.

Example 3

Figure 8:
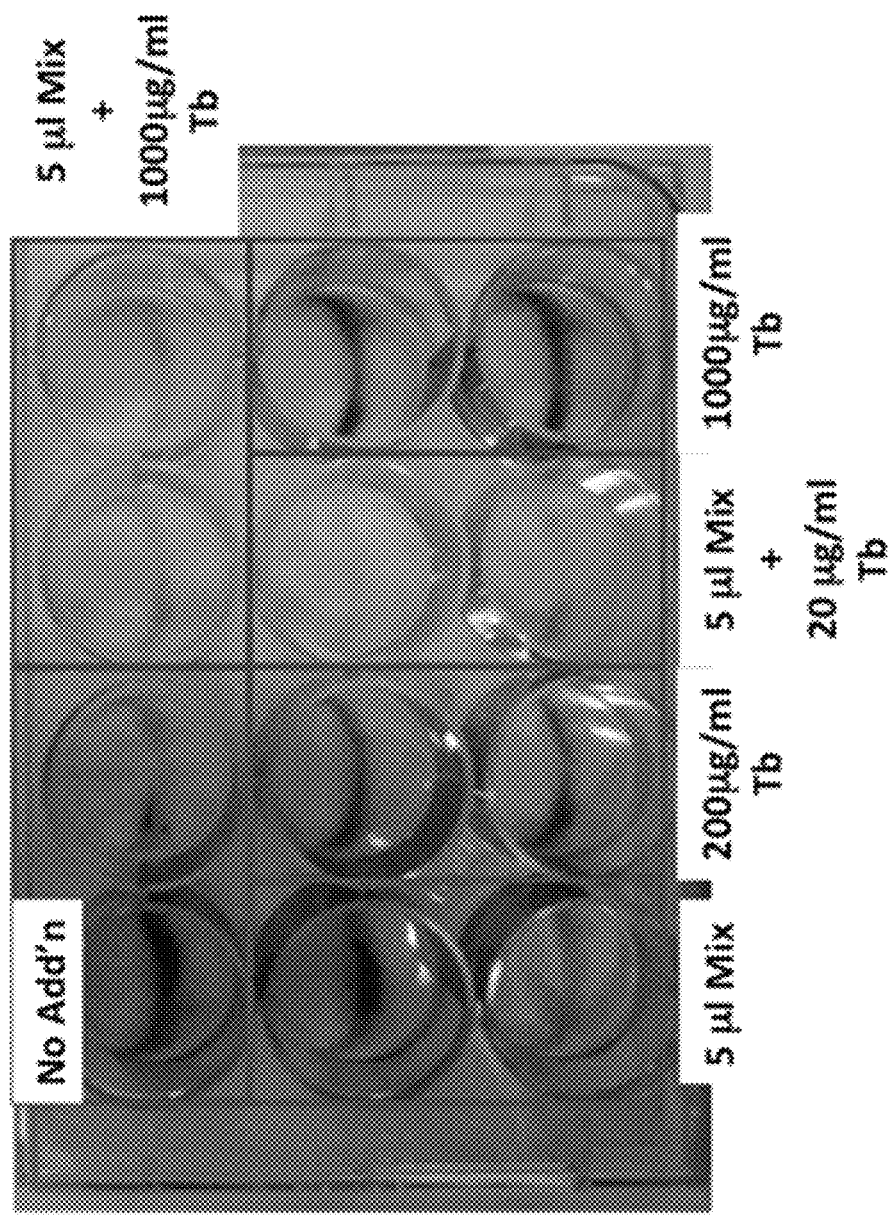
FIG. 8 is a photograph depicting the results of a biofilm disruption assay. Biofilms were grown overnight at 37° C. in a 24-well plastic dish tilted on edge to form a line of biofilm at the air-liquid interface, using M63MgArg medium inoculated with 1/100 dilution of an overnight LB grown culture of *P. aeruginosa* PA14. After overnight growth, the wells of the plate were washed 1× with 500 μl PBS, then 500 μl PBS with the indicated additions of enzymes and/or tobramycin. "Mix" indicates a mixture of the P130, P045, and P042 enzymes, each at a final concentration of ~20 μg/ml. The plates were then incubated overnight at 37° C. with gentle shaking on a platform shaker. The biofilms were detected by staining with crystal violet dye and then photographed.

Demonstration of Increased Susceptibility of *Pseudomonas aeruginosa* Cells to Antibiotics after Enzyme Treatment The ability of the carbohydrate-active enzymes to disrupt a preformed biofilm was assessed. This testing accurately reflects the state of a pre-existing *P. aeruginosa* infection in a cystic fibrosis (CF) patient, i.e., a subject that has already been colonized by the microbe. In this biofilm disruption assay, biofilms were grown overnight at 37° C. in a 24-well plastic dish tilted on edge to form a line of biofilm at the air-liquid interface, using M63MgArg medium inoculated with 1/100 dilution of an overnight LB grown culture of *P. aeruginosa* PA14. After overnight growth, the wells of the plate were washed 1× with 500 µl PBS, then 500 µl PBS with the indicated additions of enzymes and/or tobramycin. "Mix" indicates a mixture of the P130, P045, and P042 enzymes, each at a final concentration of ~20 µg/ml. The plates were then incubated overnight at 37° C. with gentle shaking on a platform shaker. The biofilms were detected by staining with crystal violet dye, then photographed. Note that the maximal attainable concentration of tobramycin in the CF lung is ~1000 µg/ml and that normal dosing is 300 mg via nebulizer over approximately 15 minutes twice daily. As shown in FIG. 8, while the enzymes alone are not effective at "disrupting" these biofilms, in combination with even quite low levels of tobramycin (Tb, 20 µg/ml, or 50-fold below the maximum attainable in vivo concentration), the biofilms are effectively dispersed.

As shown here, the combination of the carbohydrate-active enzymes mix plus 20 µg/ml Tb is effective at disrupting these biofilms. This is significant because, using prior methods, once a patient is colonized with *P. aeruginosa*, the infection is never fully eradicated (Bjarnsholt et al.). It is also significant in demonstrating the first therapeutic disruption of *P. aeruginosa* biofilm at a dosage of antibiotic that is only effective with planktonic cells.

To begin to assess these carbohydrate-active enzymes in a model more closely approximating the CF lung, the live cell, *P. aeruginosa*—airway epithelial cell co-culture model developed by the O'Toole and Stanton labs at Dartmouth (Anderson et al., Moreau-Marquis and Bomberger et al.) was used. This model recapitulates key features of the CF biofilm, including high-level antibiotic tolerance (Anderson et al., Moreau-Marquis and Bomberger et al., Moreau-Marquis and Stanton et al.). As a first step, the cytotoxicity of the carbohydrate-active enzymes versus CF-derived airway cells was assessed (e.g., the CFBE parental cell line). These data indicate that the carbohydrate-active enzymes are not cytotoxic over this 8 hr window.

Figure 9:
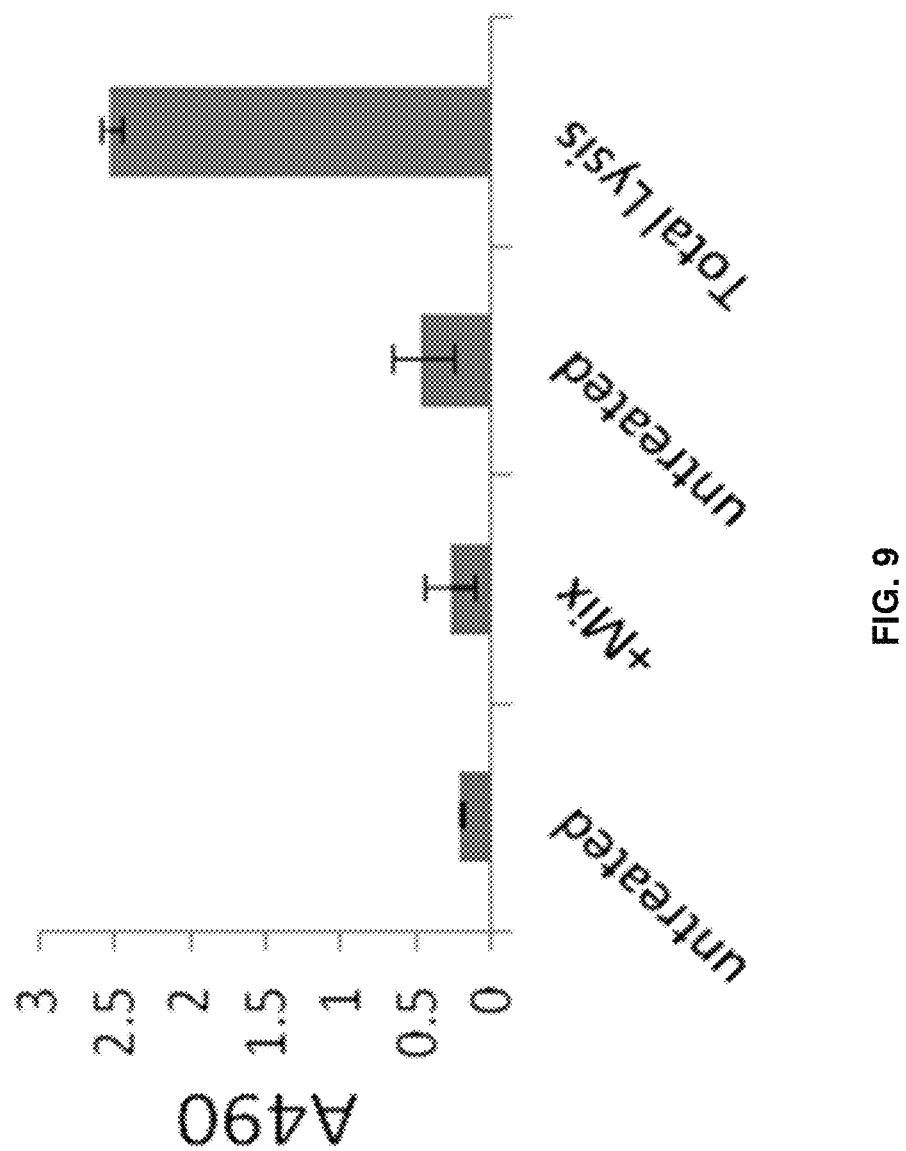
FIG. 9 is a histogram depicting cytotoxicity of CF-derived airway cells (CFBE4lo-) cells as measured by lactose dehydrogenase (LDH) assay after 8 hrs of treatment with a mix of the P130, P045, and P042 carbohydrate-active enzymes ("Mix") and compared to an untreated control ("untreated"). "Total lysis" is the positive control treated with a nonionic surfactant (Triton X-100®), which is expected to yield the maximal LDH activity. These data indicate that the carbohydrate-active enzymes are not cytotoxic over this 8 hr window.

As shown in FIG. 9, incubation of a mix of the P130, P042, and P045 carbohydrate-active enzymes for 8 hrs (Mix) had no apparent cytotoxic effects compared to the untreated controls ("untreated"). Thus, these enzyme mixtures and any of the other enzymes described herein can be tested versus biofilms grown on airway cells in future (ongoing) studies.

CONCLUSIONS

The enzymes and enzyme/antibiotic combinations exemplified in the present examples show efficacy in inhibiting *P. aeruginosa* biofilm formation, degrading pre-formed *P. aeruginosa* biofilms, and killing *P. aeruginosa* associated with the biofilms. Efficacy against infection with—and biofilms generated from—other microorganisms can be shown with the enzymes disclosed herein with and without the antimicrobial agents disclosed herein.

REFERENCES

Anderson G G, Moreau-Marquis S, Stanton B A, O'Toole G A (2008) In vitro analysis of tobramycin-treated

*Pseudomonas aeruginosa* biofilms on cystic fibrosis-derived airway epithelial cells. *Infection and Immunity* 76:1423-1433.

Auler M E, Morreira D, Rodrigues F F, Abr Ao M S, Margarido P F, Matsumoto F E, Silva E G, Silva B C, Schneider R P, Paula C R. Biofilm formation on intrauterine devices in patients with recurrent vulvovaginal candidiasis. Med. Mycol. 2010; 48(1):211-6.

Bjarnsholt T, Jensen P O, Fiandaca M J, Pedersen J, Hansen C R, et al. (2009) *Pseudomonas aeruginosa* biofilms in the respiratory tract of cystic fibrosis patients. *Pediatric Pulmonology* 44:547-558.

Colvin K M, Irie Y, Tart C S, Urbano R, Whitney J C, et al. (August 2012) The Pel and Psl polysaccharides provide *Pseudomonas aeruginosa* structural redundancy within the biofilm matrix. *Environ Microbiol* 14(8):1913-28.

Davis S C, Ricotti C, Cazzaniga A, Welsh E, Eaglstein W H, Mertz P M. Microscopic and physiologic evidence for biofilm-associated wound colonization in vivo. Wound Repair Regen. 2008; 16(1):23-9.

Digiandomenico A, Warrener P, Hamilton M, Guillard S, Ravn P, et al. (July 2012) Identification of broadly protective human antibodies to *Pseudomonas aeruginosa* exopolysaccharide Psl by phenotypic screening. *J Exp Med* 209(7): 1273-1287.

Donlan R M, Costerton J W. Biofilms: survival mechanisms of clinically relevant microorganisms. Clin Microbiol Rev. 2002; 15(2):167-93.

Hall-Stoodley L, Costerton J W, Stoodley P. Bacterial biofilms: from the natural environment to infectious diseases. *Nat Rev Microbiol.* 2004; 2(2):95-108.

Imamura Y, Chandra J, Mukherjee P K, Lattif A A, Szczotka-Flynn L B, Pearlman E, Lass J H, O'Donnell K, Ghannoum M A. *Fusarium* and *Candida albicans* biofilms on soft contact lenses: model development, influence of lens type, and susceptibility to lens care solutions. *Antimicrob Agents Chemother.* 2008; 52(1):171-82.

Johansen C, Falholt P, Gram L. Enzymatic removal and disinfection of bacterial biofilms. Appl Environ Microbiol. 1997; 63(9):3724-8.

Kaplan J B. Therapeutic potential of biofilm-dispersing enzymes. Int J Artif Organs. 2009; 32(9):545-54.

Lear, G; Lewis, G D (editor) (2012). *Microbial Biofilms: Current Research and Applications*. Caister Academic Press.

Lewis K. Riddle of biofilm resistance. *Antimicrob Agents Chemother.* 2001; 45(4):999-1007.

Moreau-Marquis S, Bomberger J M, Anderson G G, Swiatecka-Urban A, Ye S, et al. (2008) The DeltaF508-CFTR mutation results in increased biofilm formation by *Pseudomonas aeruginosa* by increasing iron availability. *Am J Physiol Lung Cell Mol Physiol* 295(1):L25-37.

Moreau-Marquis S, Stanton B A, O'Toole G A (2008) *Pseudomonas aeruginosa* biofilm formation in the cystic fibrosis airway. *Pulm Pharmacol Ther* 21(4):595-9.

Nelson N (1944) A Photometric Adaptation of the Somogyi Method for the Determination of Glucose. *J Biol Chem* 153:375-380.

Parsek M R, Singh P K. Bacterial biofilms: an emerging link to disease pathogenesis. *Annu Rev Microbiol.* 2003; 57:677-701.

Research on microbial biofilms (PA-03-047). NIH, National Heart, Lung, and Blood Institute. 2002-12-20.

Rogers. 2008 *Molecular Oral Microbiology*. Caister Academic Press. pp. 65-108.

What is claimed is:

1. A composition for reducing biofilm or inhibiting biofilm formation, said composition comprising biofilm-degrading amounts of a first purified enzyme having β-mannanase activity consisting essentially of an amino acid sequence at least 95% identical to SEQ ID NO:3, a second purified enzyme having cellulase activity consisting essentially of an amino acid sequence at least 95% identical to SEQ ID NO:6, and a third purified enzyme having cellulase activity consisting essentially of an amino acid sequence at least 95% identical to SEQ ID NO:9, and at least one antimicrobial agent.

2. The composition of claim 1 wherein the at least one antimicrobial agent comprises an aminoglycoside antibiotic.

3. The composition of claim 1 wherein the at least one antimicrobial agent comprises tobramycin.

4. The composition of claim 1 further comprising a pharmaceutically acceptable carrier.

* * * * *